United States Patent
Lengacher et al.

(10) Patent No.: US 12,310,967 B2
(45) Date of Patent: May 27, 2025

(54) COMPOSITIONS AND METHODS OF TREATMENT FOR NEUROLOGICAL DISORDERS COMPRISING MOTOR NEURON DISEASES

(71) Applicant: Gliapharm SA, Geneva (CH)

(72) Inventors: Sylvain Lengacher, Geneva (CH); Charles Finsterwald, Geneva (CH); Pierre Magistretti, Geneva (CH)

(73) Assignee: GLIAPHARM SA, Geneva (CH)

( * ) Notice: Subject to any disclaimer, the term of this patent is extended or adjusted under 35 U.S.C. 154(b) by 0 days.

(21) Appl. No.: 17/409,836

(22) Filed: Aug. 24, 2021

(65) Prior Publication Data

US 2022/0040189 A1 Feb. 10, 2022

Related U.S. Application Data

(63) Continuation-in-part of application No. 16/955,227, filed as application No. PCT/IB2018/060442 on Dec. 20, 2018, now abandoned.

(60) Provisional application No. 62/608,625, filed on Dec. 21, 2017.

(51) Int. Cl.
| | |
|---|---|
| *A61K 31/517* | (2006.01) |
| *A61K 31/519* | (2006.01) |
| *A61K 31/5377* | (2006.01) |
| *A61K 31/5513* | (2006.01) |
| *A61P 25/28* | (2006.01) |

(52) U.S. Cl.
CPC .......... *A61K 31/519* (2013.01); *A61K 31/517* (2013.01); *A61K 31/5377* (2013.01); *A61K 31/5513* (2013.01); *A61P 25/28* (2018.01)

(58) Field of Classification Search
CPC ................ A61K 31/517; A61K 31/519; A61K 31/5377; A61P 25/28
See application file for complete search history.

(56) References Cited

U.S. PATENT DOCUMENTS

| | | |
|---|---|---|
| 2,739,968 A | 3/1956 | Sperber |
| 3,340,279 A | 9/1967 | Paul |
| 3,381,009 A | 4/1968 | Giuseppe |
| 4,525,361 A | 6/1985 | Morimoto |
| 4,572,912 A | 2/1986 | Yoshioka |
| 4,731,447 A | 3/1988 | Schumacher |
| 4,842,775 A | 6/1989 | Okada |
| 5,859,037 A | 1/1999 | Whitcomb |
| 5,885,976 A | 3/1999 | Sandyk |
| 5,916,925 A | 6/1999 | Higuchi |
| 6,011,049 A | 1/2000 | Whitcomb |
| 6,228,869 B1 | 5/2001 | Levin |
| 6,511,800 B1 | 1/2003 | Singh |
| 7,541,371 B2 | 6/2009 | Arakawa |
| 8,293,800 B2 | 10/2012 | Meier |
| 8,741,853 B2 | 6/2014 | Steliou |
| 2003/0013692 A1 | 1/2003 | Gullans |
| 2004/0077525 A1 | 4/2004 | Chapman |
| 2004/0224995 A1 | 11/2004 | Simpkins |
| 2004/0259888 A1* | 12/2004 | Bischoff ................. A61P 43/00 514/227.8 |
| 2005/0059656 A1 | 3/2005 | Kristal |
| 2006/0177381 A1 | 8/2006 | Brooks-Korn |
| 2007/0142437 A1 | 6/2007 | Brown |
| 2008/0058327 A1 | 3/2008 | Mitchell |
| 2008/0145423 A1 | 6/2008 | Khan |
| 2009/0163545 A1 | 6/2009 | Goldfarb |
| 2011/0230350 A1 | 9/2011 | Frackenpohl |
| 2011/0245230 A1 | 10/2011 | Mitchell |
| 2013/0189343 A1 | 7/2013 | Krumme |
| 2014/0349996 A1 | 11/2014 | Mitchell |
| 2015/0143553 A1 | 5/2015 | Zarnescu |
| 2016/0030426 A1* | 2/2016 | Tester .................. C07D 239/48 544/323 |
| 2016/0045508 A1 | 2/2016 | Vazquez |
| 2020/0325148 A1 | 10/2020 | Lengacher |
| 2020/0339591 A1 | 10/2020 | Lengacher |
| 2022/0040186 A1 | 2/2022 | Lengacher |
| 2022/0040197 A1 | 2/2022 | Lengacher |

FOREIGN PATENT DOCUMENTS

| | | |
|---|---|---|
| CN | 103040779 | 4/2013 |
| CN | 104725398 A * | 6/2015 |
| DE | 1443813 | 11/1968 |
| EP | 0629400 | 12/1994 |
| EP | 1583541 | 10/2005 |
| EP | 1891946 | 2/2008 |
| EP | 2876107 | 5/2015 |
| FR | 7524 M | 12/1969 |
| FR | 2578742 | 9/1986 |
| FR | 2841141 | 12/2003 |
| GB | 577843 | 6/1946 |

(Continued)

OTHER PUBLICATIONS

Machine translation of CN104725398A, Jun. 2015, p. 1-8. (Year: 2015).*
Haim et al., JAK/STAT3 pathway is a common inducer of astrocyte reactivity in Alzheimer's and Huntington's diseases, Feb. 2015, Journal of Neuroscience, vol. 35, No. 6, p. 2817-2829. (Year: 2015).*
Camandol et al, Brain metabolism in health, aging and neurodegeneration, 2017, EMBO Journal, vol. 36, No. 11, 1474-1492. (Year : 2017).*
Yokoyama et al., Effects of RS-2232, a Potential Antidepressant, on the levels of monoamines, precursor amino acids and their related metabolites in mouse brain, 1987, Japan J. Pharmacol., vol. 44, p. 413-420 (Year: 1987).*

(Continued)

*Primary Examiner* — Kamal A Saeed
*Assistant Examiner* — Karen Cheng
(74) *Attorney, Agent, or Firm* — SALIWANCHIK, LLOYD & EISENSCHENK

(57) ABSTRACT

This invention, in at least some embodiments, relates to an inventive molecule, compositions comprising same, and methods of use thereof for treatment of a neurological disorder.

7 Claims, 24 Drawing Sheets

(56) References Cited

FOREIGN PATENT DOCUMENTS

| | | |
|---|---|---|
| GB | 1417578 | 12/1975 |
| JP | 2000273040 | 10/2000 |
| JP | 2001261560 | 9/2001 |
| KR | 20150047161 | 5/2015 |
| WO | 9519171 | 7/1995 |
| WO | 9519173 | 7/1995 |
| WO | 9636595 | 11/1996 |
| WO | 9816514 | 4/1998 |
| WO | 9831356 | 7/1998 |
| WO | 9918076 | 4/1999 |
| WO | 9947508 | 9/1999 |
| WO | 0035437 | 6/2000 |
| WO | 2000051605 | 9/2000 |
| WO | 0117982 | 3/2001 |
| WO | 03018589 A1 | 3/2003 |
| WO | 2004032882 | 4/2004 |
| WO | 2004045592 | 6/2004 |
| WO | 2006084184 | 8/2006 |
| WO | 2007107442 | 9/2007 |
| WO | 2007108569 | 9/2007 |
| WO | 2008023357 | 2/2008 |
| WO | 2009043593 | 4/2009 |
| WO | 2009123580 | 10/2009 |
| WO | 2011011722 A1 | 1/2011 |
| WO | 2013033037 | 3/2013 |
| WO | 2013092269 | 6/2013 |
| WO | 2014035355 | 3/2014 |
| WO | 2014099837 | 6/2014 |
| WO | 2015195684 | 12/2015 |
| WO | 2016112177 | 7/2016 |
| WO | WO2018023029 A1 * | 2/2018 |
| WO | 2019123375 | 6/2019 |
| WO | 2019123378 | 6/2019 |

OTHER PUBLICATIONS

Ostadkarampour et al., Monoamine Oxidase Inhibitors: A Review of Their Anti-Inflammatory Therapeutic Potential and Mechanisms of Action, 2021, Frontiers in Pharmacology, vol. 12, p. 1-17 (Year: 2021).*

"4-Diazomethylpyridine as a Derivatization Reagent and Its Application to the Determination of Prostaglandin E2 by LC-MS/MS", Zeng et al., Chromatographia (2012), 75(15-16), 875-881.

"Electron-withdrawing substituted benzenesulfonamides against the predominant community-associated methicillin-resistant *Staphylococcus aureus* strain USA300" Phetsang et al., Monatshefte fuer Chemie (2013), 144(4), 461-471.

"Identification and preliminary structure-activity relationship studies of novel pyridyl sulfonamides as potential Chagas disease therapeutic agents" Peres et al., Bioorganic & Medicinal Chemistry Letters (2018), 28(11), 2018-2022.

"Lactate-starved neurons in ALS" Martinez, Disease Models & Mechanisms 5, 711-712 (2012).

"Novel compounds lowering the cellular isoform of the human prion protein in cultured human cells" Silber et al., Bioorganic & Medicinal Chemistry (2014), 22(6), 1960-1972.

"Oligodendroglia metabolically support axons and contribute to neurodegeneration" Lee et al., Nature. Jul. 26, 2012; 487(7408): 443-448.

"Peripheral administration of lactate produces antidepressant-like effects" Carrad et al., Molecular Psychiatry (2016) 00, 1-8.

"Screening of HIV-1 replication inhibitors by using pseudotyped virus system" Cao et al., Yaoxue Xuebao (2008), 43 (3), 253-258.

"Simple and Versatile Catalytic System for N-Alkylation of Sulfonamides with Various Alcohols" Zhu et a., Organic Letters (2010), 12(6), 1336-1339.

"Solid phase synthesis of sulfonamides using a carbamate linker" Raju et al., Tetrahedron Letters (1997), 38(19), 3373-3376.

"Synthesis of N,N'-bis(phenylsulfonyl)-1,2-bis(4-pyridyl)ethylenediamines" Brana et al., Liebigs Annalen der Chemie (1990), (7), 641-5.

"YU238259 Is a Novel Inhibitor of Homology-Dependent DNA Repair That Exhibits Synthetic Lethality and Radiosensitization in Repair-Deficient Tumors" Stachelek et al., Molecular Cancer Research (2015), 13(10), 1389-1397.

"Astrocytes: New Targets for the Treatment of Neurodegenerative Diseases" Charles Finsterwald, Pierre J. Magistretti and Sylvain Lengacher, Current Pharmaceutical Design, 2015, 21, 3570-3581.

Pubchem Substance SID 106499093 Publication data: 20110222.
Pubchem Substance SID 106500615 Publication data: 20110222.
Pubchem Substance SID: 106499194 Publication data: 20110222.
Pubchem Substance SID: 106502067 Publication data: 20110222.

Office Action (Non-Final Rejection) dated Aug. 14, 2023 for U.S. Appl. No. 17/409,834 (pp. 1-27).

Office Action (Final Rejection) dated Dec. 27, 2023 for U.S. Appl. No. 17/409,834 (pp. 1-16).

* cited by examiner

| GP ID | Family | Other name | Structure |
|---|---|---|---|
| GP-0171 | Family N | GP-61 series, GP-612; T0517-8250 | 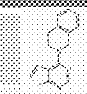 |
| GP-0260 | Family R | GP-62 series; T5580243 | 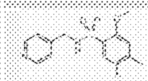 |
| GP-0196 | Family P | GP-62 series; P025-0159 | 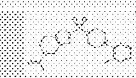 |
| GP-0365 | | GP-61 series; Z606-8287 | 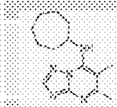 |
| GP-0368 | | GP-61 series; Z606-9398 | 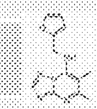 |
| GP-0366 | | GP-61 series; Z606-8351 | 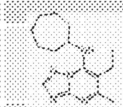 |
| GP-0241 | | GP-62 series; T5400234 | 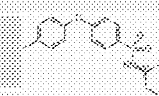 |
| GP-0157 | | GP-61 series, GP-61.1, T5712071 | 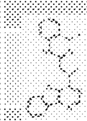 |
| GP-0242 | | GP-62 series, GP-62.1, T5894329 | 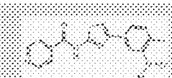 |

Figure 18

COMPOSITIONS AND METHODS OF TREATMENT FOR NEUROLOGICAL DISORDERS COMPRISING MOTOR NEURON DISEASES

FIELD OF THE INVENTION

The present invention, in at least some aspects, relates to compositions and methods of treatment for neurological disorders, and in particular to compositions containing an inventive molecule as described herein and methods of treatment using same.

BACKGROUND OF THE INVENTION

Amyotrophic lateral sclerosis (ALS) is a rare neurological disease that belongs to a wider group of neurological diseases called motor neuron diseases (MND). It mainly affects the nerve cells (neurons) responsible for controlling voluntary muscle movement. The disease is progressive. Currently, there is no cure for ALS and no effective treatment to halt, or reverse, the progression of the disease. The two existing drugs for ALS, Riluzole and Ederavone, were shown to prolong patients' lifetime by a few months only.

ALS belongs to a wider group of disorders known as motor neuron diseases, which are caused by gradual deterioration (degeneration) and death of motor neurons. Motor neurons are nerve cells that extend from the brain to the spinal cord and to muscles throughout the body. These motor neurons initiate and provide vital communication links between the brain and the voluntary muscles.

Messages from motor neurons in the brain (called upper motor neurons) are transmitted to motor neurons in the spinal cord and to motor nuclei of brain (called lower motor neurons) and from the spinal cord and motor nuclei of brain to a particular muscle or muscles.

In ALS, both the upper motor neurons and the lower motor neurons degenerate or die, and stop sending messages to the muscles. Unable to function, the muscles gradually weaken, start to twitch (called fasciculations), and waste away (atrophy). Eventually, the brain loses its ability to initiate and control voluntary movements.

BRIEF SUMMARY OF THE INVENTION

The background art fails to provide therapies that successfully treat ALS (amyotrophic lateral sclerosis). The present invention, in at least some embodiments, provides compositions comprising inventive molecules as described herein and methods of treatment with same. By "inventive molecule" it is meant a molecule which, as described herein, has been shown to have at least one effect in vitro and/or in vivo, that indicates that it would be useful in the compositions and methods of treatment described herein.

Preferably the treatment comprises an increase of energy metabolism in the nervous system.

Optionally treating comprises one or more of curing, managing, reversing, attenuating, alleviating, minimizing, suppressing, managing, or halting the deleterious effects of the above-described diseases.

Treatment as Prevention of Disease and/or Symptom Onset

According to at least some embodiments, treating also includes at least reducing the rate of onset of symptoms and/or etiology of the disease, for example optionally as determined by measurement of one or more diagnostic markers. Such diagnostic markers would be selected according to the particular neurological disorder.

With regard to the inventive molecules as described herein, without wishing to be limited by a single hypothesis, it is possible that for each disease described herein, prevention or delay of full onset or even symptomatic presentation of these diseases in subjects without symptoms of the disease, or with only minor initial symptoms would be possible by detecting the disease in the subject before full onset or symptomatic presentation, and then administering the inventive molecules as described herein to the subject according to a suitable dosing regimen.

Optionally, managing comprises reducing the severity of the disease, reducing the frequency of episodes of the disease, reducing the duration of such episodes, or reducing the severity of such episodes or a combination thereof.

Individuals at risk of developing a disease can be identified based on various approaches either before disease development or at very early stages in which disease markers can be identified. The identification of individuals at risk as well as diagnosis of early disease can rely on various approaches including genomics, proteomics, metabolomics, lipidomics, glycomics, secretomics, serologic approaches and also optionally tests involving impairment of information processing (see doi:10.1016/j.psychres.2006.09.014). Family history can also provide information either in combination with one of the previously described approaches or as a standalone approach. Furthermore, over the past decade microbiome composition is becoming recognized as an important factor in health and disease. The advent of new technologies for interrogating complex microbial communities and in the analysis of microbiome and metagenome will provide another approach for identification of individuals at risk of developing a disease.

BRIEF DESCRIPTION OF THE FIGURES

FIG. 18 shows the correspondence between GP Identification number, chemical families, other name including commercial numbers and chemical structures.

DETAILED DESCRIPTION OF THE INVENTION

Figure 1:
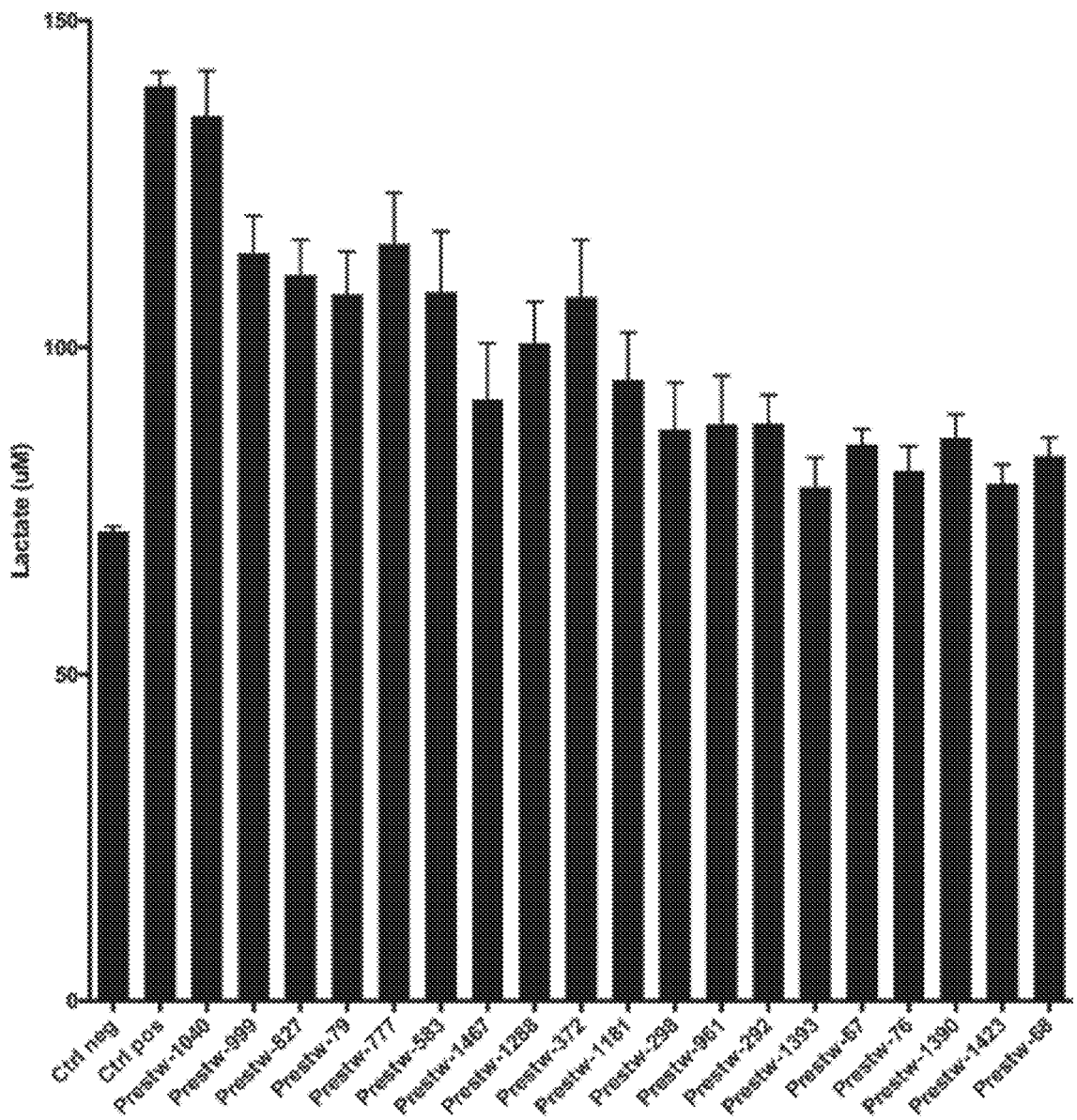
FIG. 1 shows the extracellular levels of lactate in astrocytes after treatment with inventive molecules from the Prestwick library.

The present invention, in at least some embodiments, relates to molecules, compositions and methods of treatment comprising same for treatment of a neurological disease, wherein the composition comprises an inventive molecule as described herein. The neurological disease is specifically ALS (Amyotrophic lateral sclerosis) and its subtypes. ALS subtypes include bulbar-onset ALS and limb-onset ALS. In addition to ALS and its subtypes, optionally the inventive molecules could be used for treatment of other types of MND including primary lateral sclerosis (PLS), progressive bulbar palsy and progressive muscular atrophy, as described herein.

According to at least some embodiments, there is provided a molecule selected from the group consisting of Families A, C, E, F(7), F(6), G, I, M, PQRV and Y;
wherein Family G comprises:

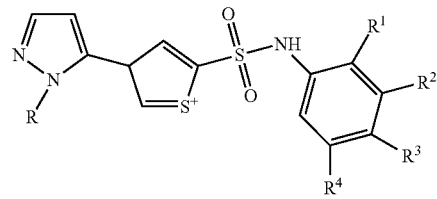

wherein for Family G, R is H, ethyl or methyl; each of R1-R4 is independently H, halogen; alkyl; or alkoxy;
wherein Family A comprises:

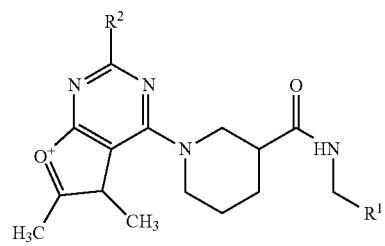

wherein R1 is H or benzyl unsubstituted or substituted with nitrogen, R2 is H or alkyl, with the proviso that if R2 is H, R1 is not

and with the further proviso that the structure is not that of catalog ID numbers F228-0365, F228-0351, F228-0856 or F228-0541 of Appendix I;

wherein Family C comprises:

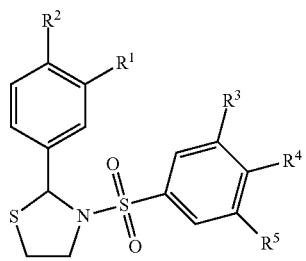

wherein R1 and R2 are each H or methoxy; each of R3, R4 and R5 are independently alkyl, preferably ethyl, or H; preferably only one of R3-R5 is alkyl, preferably ethyl; more preferably R4 is alkyl, most preferably ethyl;

with the proviso that the structure is not that of catalog ID numbers T5464782, F1462-0491, T5463709 or 4052-4279 of Appendix I;

wherein Family E comprises:

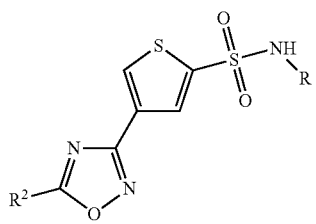

wherein R is pentyl, benzyl, alkyl benzyl or R1; R2 is alkyl, cyclopentyl or cyclobutane; wherein R1 is

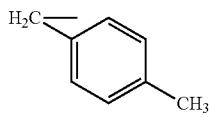 or 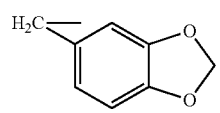

with the proviso that the structure is not that of catalog ID numbers L287-1577, or L287-1758 of Appendix I;

wherein Family F(7) comprises:

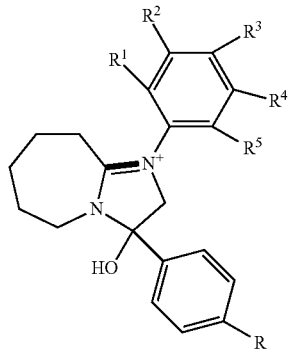

wherein R is alkyl, halogen, or alkoxy;
each of R1-R5 is independently H, alkyl, or alkoxy;
with the proviso that the structure is not that of catalog ID numbers K404-0672, K404-0183, K404-0796, F0524-0511, F0524-0507, F0522-0533, F0524-0488, K404-0400, T0507-8442, K404-0906, K404-0842, K404-0852, K404-0914, K404-0915, K404-0828, K404-0863 or K404-0277 of Appendix I;

wherein Family F(6) comprises:

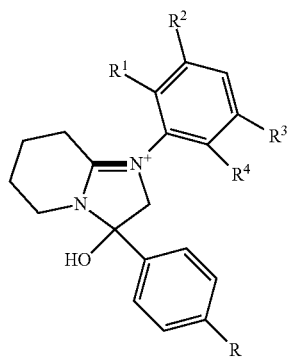

wherein for Family F(6) R is H, halogen; alkyl or alkoxy;
R1, R2, R3 and R4 are each independently H, alkyl, or alkoxy, with the proviso that if R1 is alkoxy, R is not alkyl and is preferably halogen or alkoxy;

with the proviso that the structure is not that of catalog ID numbers K404-0672, K404-0183, K404-0796, F0524-0511, F0524-0507, F0522-0533, F0524-0488, K404-0400, T0507-8442, K404-0906, K404-0842, K404-0852, K404-0914, K404-0915, K404-0828, K404-0863 or K404-0277 of Appendix I;

wherein Family I comprises:

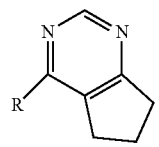

wherein for Family I, R is

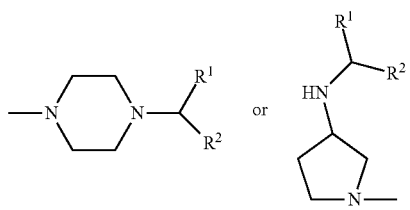

wherein for Family I, R1 is cyclopentadiene or benzene, unsubstituted or substituted with S, O or N; R2 is H or a carbonyl;

wherein for Family I, R1 is selected from the group consisting of (alternative atoms at each position are indicated in brackets)

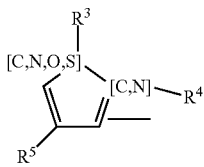

wherein each of R3, R4 and R5 is independently H, alkyl (preferably methyl);
and

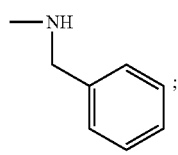

with the proviso that the structure is not that of catalog ID numbers T636-2007, T636-1250, T636-2391, T636-0054, T636-0027, T636-1243, T636-2360, T636-0085, T636-0181, D278-0514, T636-1715, T636-2144, T636-1601, or T636-0973 of Appendix I;

wherein Family M comprises:

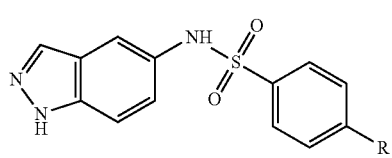

wherein R is H or alkyl; if alkyl, R is methyl or ethyl, unsubstituted or substituted with halogen (preferably F or Cl, more preferably F; preferably up to three halogens), more preferably ethyl; with the proviso that the structure is not that of catalog ID number T5436375 of Appendix I;

wherein Family PQRV comprises (brackets indicate that the atom at that position can be C or N):

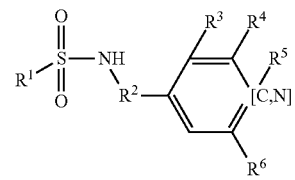

wherein R1 is benzyl,

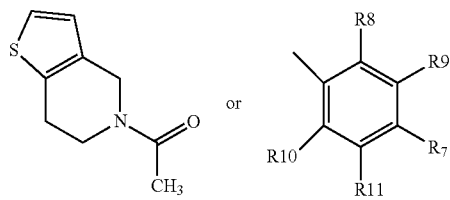

wherein R2 is alkyl, forms a heterocyclic hexyl moiety with the nitrogen to which it is attached, or is absent;
wherein each of R3, R4, R5 and R6 are halogen, H, alkyl, benzyl or alkyl benzyl (unsubstituted or substituted with nitrogen), cyclopentadiene or alky cyclopentadiene (substituted or unsubstituted with S or N) or carbamoyl (optionally alkyated with cyclopropane); R4 and R5 together can be cyclopentadiene, substituted with S and/or N, or unsubstituted, and optionally alkylated;
wherein each of R7-R11 is independently halogen, alkyl, or methoxy, and can be the same or different; or is pyrrolidine, optionally formyl pyrrolidine, in which case preferably R7 is pyrrolidine;
with the proviso that the structure is not that of catalog ID numbers P025-0462, P025-0080, P025-0168, T5581430, F0376-0203, or T5246417 of Appendix I;
with the proviso that if R1 is:

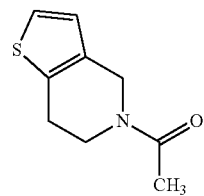

R2 forms a heterocyclic hexyl moiety with the nitrogen to which it is attached;
with the proviso that if R1 is

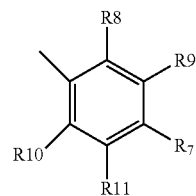

R7 is pyrrolidine, and [C,N] is C, then R4 is not cyclopentadiene or alky cyclopentadiene substituted with both S and N;

with the proviso that if R1 is

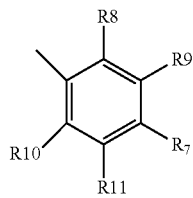

[C,N] is N and R3-R6 are H, then none of R7-R11 is methyl, methoxy or halogen;
with the proviso that if R1 is

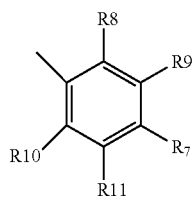

any of R7-R11 is chlorine, and [C,N] is N, then R5 isn't carbamoyl;
with the proviso that if R1 is

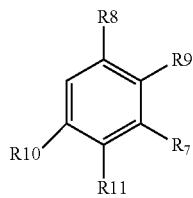

[C,N] is C, any of R7-R11 is halogen or methoxy, and R4 and R5 together form cyclopentadiene, substituted with S and/or N, then the cyclopentadiene moiety is not alkylated nor does it feature a benzyl group;
wherein Family Y comprises:

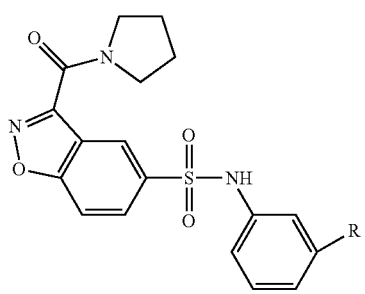

wherein R is alkyl, S or halogen, preferably S or halogen; if halogen, preferably F; if S, preferably methylthio or ethylthio, most preferably methylthio; with the proviso that the structure is not that of catalog ID numbers L995-0405 or L995-0386 of Appendix I.
Optionally for the above molecule, for Family G, R is methyl or ethyl; for R1-R4, if halogen, one or more of R1-R4 is F or Cl; if alkyl, one or more is ethyl or methyl; if alkoxy, one or more ethoxy or methoxy;

wherein for Family A, R1 is nitrogen substituted benzyl or H, and R2 is H;
wherein for Family C, R1 and R2 are each methoxy; each of R3-R5, if alkyl, is ethyl;
wherein for Family E, R is pentyl or R1; if R2 is alkyl, R2 is methyl or ethyl;
  wherein for Family F(6) if R is halogen, R is F or Cl; if R is alkyl, R is methyl or ethyl; if R is alkoxy, R is methoxy or ethoxy;
  if any of R1-R5 is alkyl, then it is methyl; if any of R1-R5 is alkoxy, then it is methoxy or ethoxy; with the proviso that if R1 is alkoxy, R is not alkyl and is preferably halogen or alkoxy;
  wherein for Family F(7), if R is alkyl, R is ethyl or methyl; if R is halogen, R is Cl or F; if R is alkoxy, R is methoxy or ethoxy; if any of R1-R5 is alkyl, then it is methyl; if any of R1-R5 is alkoxy, then it is methoxy or ethoxy;
wherein for Family M, if R is alkyl, R is methyl or ethyl, unsubstituted or substituted with halogen;
wherein for Family Y, if R is alkyl, R is ethyl or methyl; if R is S, R is methylthio or ethylthio; if R is halogen, R is F;
Optionally for the above molecule: wherein for Family G, each of R1-R4, if alkyl, is methyl; if alkoxy, is methoxy;
  wherein for Family C, only one of R3-R5 is ethyl and the remaining are H;
  wherein for Family M, if R is alkyl, R is ethyl;
  wherein for Family Y, R is S or halogen;
Optionally for the above molecule: wherein for Family G, at least two of R1-R4 are halogen, at least two are alkyl, one is alkoxy and one is alkyl, one is alkyl and one is H, one is halogen and one is H, or one is alkoxy and one is H;
  wherein for Family C, R4 is ethyl, and R3 and R5 are H;
  wherein for Family M, if R is ethyl, R is substituted with F or Cl, more preferably F; preferably up to three halogens;
  wherein for Family Y, if R is S, R is methylthio.
Optionally for the above molecule: for Family G, the molecule is selected from the group consisting of GI-G6 of Appendix I (molecules having catalog numbers L924-1031; L924-1088; L924-0830; L924-0760; L924-0884; or L924-0988);
  wherein for Family A, the molecule is selected from the group consisting of A1-A3 of Appendix I (molecules having catalog numbers F228-0422, F228-0350 or F228-0534);
  wherein for Family C, the molecule is selected from the group consisting of C1-C3 of Appendix I (molecules having catalog numbers T5463586, 4052-4304 or T5463658);
  wherein for Family E, the molecule is selected from the group consisting of E1-E4 of Appendix I (molecules having catalog numbers L287-0468, L287-1641, L287-1221 and L287-0220);
  wherein for Family F(6), the molecule is selected from the group consisting of F4-F6, F8, F9, F13 of Appendix I (molecules having catalog numbers K404-0800, K404-0673, F0524-0338, K404-0685, K404-0697, and K404-0394);
  wherein for Family F(7), the molecule is selected from the group consisting of F1-F3, F7, F10-F12 of Appendix I (molecules having catalog numbers K404-0834, K404-0838, K404-0885, K404-0910, K404-0855, K404-0860, and F0524-0611);
  wherein for Family I, the molecule is selected from the group consisting of I1-I5 and I7 of Appendix I (molecules having catalog numbers T636-1937, T636-1114, T636-2387, T636-0134, T636-1210 and T636-2425);

wherein for Family M, the molecule is selected from the group consisting of M1 and M2 of Appendix I (molecules having catalog numbers T5599014 and T5653029);

wherein for Family PQRV, the molecule is selected from the group consisting of P1, Q1-Q3, R1, V1 and V2 of Appendix I (molecules having catalog numbers P025-0159, T5644989, T5599698, T5618591, T5580243, T6937001 and T5511047); and wherein for Family Y, the molecule is selected from the group consisting of Y1 and Y2 of Appendix I (molecules having catalog numbers L995-0125 and L995-0058).

In one embodiment of the present invention Family A is a compound represented by a structural formula selected from:

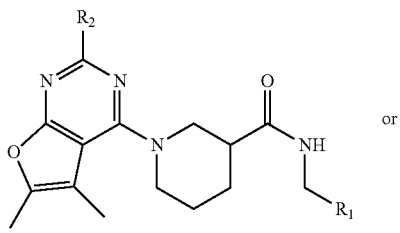

or

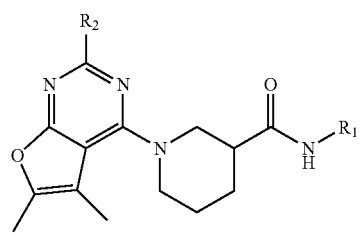

wherein:

$R_1$ is —H or optionally substituted alkyl, aryl, aralkyl or heteroaryl; in one embodiment $R_1$ is —H or optionally substituted alkyl, aryl, aralkyl or nitrogen containing heteroaryl; in one embodiment $R_1$ is —H or optionally substituted alkyl, phenyl, benzyl or nitrogen containing heteroaryl; in one embodiment $R_1$ is —H or optionally substituted alkyl, phenyl, benzyl or pyridyl; and $R_2$ is —H or optionally substituted alkyl; in one embodiment $R_2$ is —H or alkyl; in one embodiment $R_2$ is —H.

In one embodiment $R_1$ is —H, C1-6 alkyl, phenyl, pyridyl, pyrazinyl, pyrimidinyl or pyridazinyl; and R2 is —H or C1-6 alkyl. In another embodiment $R_1$ is —H, phenyl or pyridyl and $R_2$ is —H.

In one embodiment for the compounds of Family A and the methods of the present invention if R2 is —H, $R_1$ is not pyridyl. In another embodiment for the compounds of Family A and the methods of the present invention the structure is not that of catalog ID numbers F228-0365, F228-0351, F228-0856 or F228-0541 of Appendix I.

In one embodiment Family C is a compound represented by the following structural formula:

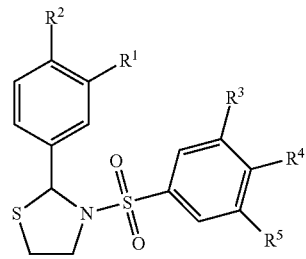

wherein:

$R^1$ and $R^2$ are each independently —H or optionally substituted —Oalkyl; in one embodiment $R^1$ and $R^2$ are each independently —H or —OCH$_3$; and each of $R^3$, $R^4$ and $R^5$ are independently —H optionally substituted alkyl; in one embodiment each of $R^3$, $R^4$ and $R^5$ are independently —H, methyl or ethyl; in one embodiment only one of $R^3$, $R^4$ and $R^5$ is alkyl; in one embodiment R4 is alkyl; in one embodiment $R^4$ is methyl;

In one embodiment for the compounds of Family C and the methods of the present invention the structure is not that of catalog ID number T5464782, F1462-0491, T5463709, or 4052-4279 of Appendix I.

In one embodiment Family E is a compound represented by the following structural formula:

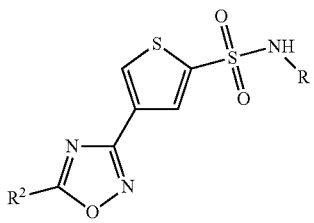

wherein:

R is optionally substituted alkyl, cycloalkyl, aryl or aralkyl; R is optionally substituted cycloalkyl, aryl or aralkyl; in one embodiment R is optionally substituted cyclopentyl, phenyl, benzyl or —CH3- benzodioxolyl; in one embodiment R is

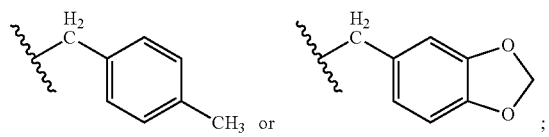

and

R2 is optionally substituted alkyl or cycloalkyl; in one embodiment R2 is alkyl, cyclopentyl or cyclobutyl.

In one embodiment for the compounds of Family E and the methods of the present invention the structure is not that of catalog ID number L287-1577, or L287-1758 of Appendix I.

In one embodiment Family F(7) is a compound represented by the following structural formula:

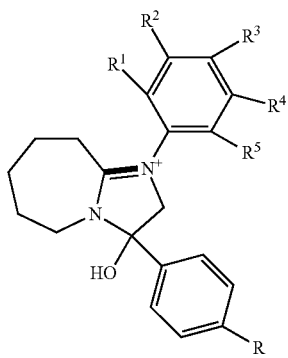

wherein:
R is —H, halogen, —NO$_2$ or optionally substituted alkyl, or alkoxy; in one embodiment R is —H, halogen, —NO$_2$, alkyl, or alkoxy; in one embodiment R is —H, halogen, alkyl, or alkoxy; and each of R$^1$-R$^5$ is independently —H or optionally substituted alkyl or alkoxy; in one embodiment each of R$^1$-R$^5$ is independently —H, alkyl or alkoxy.

In one embodiment for the compounds of Family F(6) and the methods of the present invention the structure is not that of catalog ID numbers K404-0672, K404-0183, K404-0796, F0524-0511, F0424-0507, F0522-0533, F0524-0488, K404-0400, T0507-8442, K404-0906, K404-0842, K404-0852, K404-0914, K404-0915, K404-0828, K404-0863 or K404-0277 of Appendix I;

In one embodiment Family F(6) is a compound represented by the following structural formula:

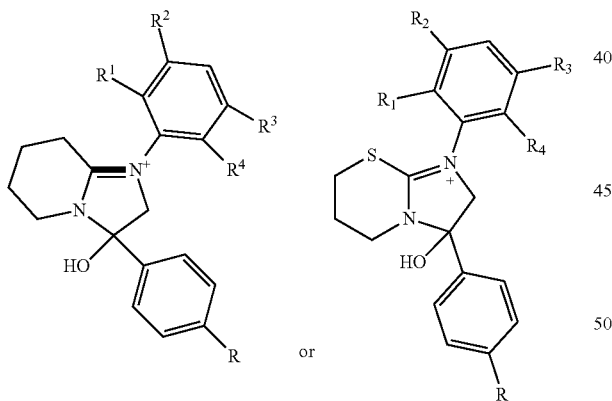

wherein for Family F(6):
R is —H, halogen or optionally substituted alkyl or alkoxy; in one embodiment R is —H, halogen, alkyl or alkoxy; and R$^1$, R$^2$, R$^3$ and R$^4$ are each independently —H or optionally substituted alkyl, or alkoxy; in one embodiment R$^1$, R$^2$, R$^3$ and R$^4$ are each independently —H alkyl, or alkoxy.

In one embodiment if R$^1$ is alkoxy, R is not alkyl. In one embodiment if R$^1$ is alkoxy, R is halogen or alkoxy.

In one embodiment for the compounds of Family F(6) and the methods of the present invention the structure is not that of catalog ID numbers K404-0672, K404-0183, K404-0796, F0524-0511, F0424-0507, F0522-0533, F0524-0488, K404-0400, T0507-8442, K404-0906, K404-0842, K404-0852, K404-0914, K404-0915, K404-0828, K404-0863 or K404-0277 of Appendix I;

In one embodiment Family G is a compound represented by the following structural formula:

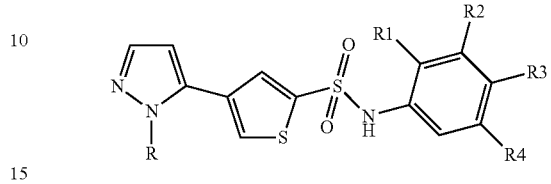

wherein for Family G:
R is —H, methyl or ethyl; and
each of R$^1$-R$^4$ is independently —H, halogen, alkyl or alkoxy.

In one embodiment Family I is a compound represented by the following structural formula:

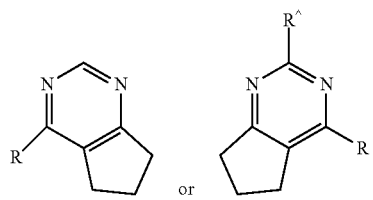

wherein for Family I:
R is —N(R$^\$$)$_2$, wherein R$^\$$ is —H or optionally substituted alkyl, heterocycloalkyl or aryl, or two R$^\$$ join together to form an optionally substituted nitrogen containing heterocyclic ring; in one embodiment R is —N(R$^\$$)$_2$, wherein R$^\$$ is —H or alkyl or heterocycloalkyl or aryl each optionally and independently substituted with one or more R4, or two R$^\$$ join together to form a nitrogen containing heterocyclic ring selected from the group of piperidinyl, piperazinyl, pyrrolidinyl, imidazolidinyl, pyrazolidinyl, azepanyl or diazepanyl each optionally and independently substituted with one or more R$^\#$; in one embodiment R is —N(R$^\$$)$_2$, wherein R$^\$$ is —H, alkyl, pyrrolidinyl, piperidinyl or phenyl each optionally and independently substituted with one or more R$^\#$, or two R$^\$$ join together to form a nitrogen containing heterocyclic ring selected from the group of piperidinyl, piperazinyl, pyrrolidinyl, imidazolidinyl, pyrazolidinyl, azepanyl or diazepanyl each optionally and independently substituted with one or more R$^\#$;

R$^\#$ is optionally substituted alkyl, —Oalkyl, heterocycloalkyl, —Oheterocycloalkyl, aryl, —C(O)aryl, —C(O)aralkyl, heteroaryl, heteroaralkyl, —C(O)heteroaryl, or —N(R$^\&$)$_2$;

R$^\&$ is —H or optionally substituted alkyl, —Oalkyl, aryl, heteroaryl, —Oheterocycloalkyl, —S(O)$_2$aryl, —C(O)aryl, —C(O)aralkyl, —C(O)heteroaryl, —C(O)NHaralkyl; and R$^\wedge$ is —H, alkyl, aryl or heteroaryl.

In one embodiment R$^\#$ and R$^\&$ are each optionally and independently substituted with one or more alkyl, haloalkyl, aryl, heteroaryl, halo, —Oalkyl, —CN, In one embodiment for the compounds of Family I and the methods of the present invention the structure is not that of catalog ID numbers T636-2007, T636-1250, T636-2391, T636-0054, T636-0027, T636-1243, T636-2360, T636-0085, T636-0181, D278-0514, T636-1715, T636-2144, T636-1601, or T636-0973 of Appendix I;

In one embodiment Family Y is a compound represent by the following structural formula:

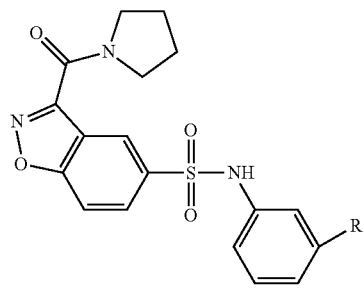

Wherein:
R is —H, halogen, —SR$^x$ or optionally substituted alkyl; in one embodiment R is halogen, —SCH$_3$, or —SCH$_2$CH$_3$; and R$^x$ is optionally substituted alkyl; in one embodiment R$^x$ is alkyl.

In one embodiment for the compounds of Family Y and the methods of the present invention the structure is not that of catalog ID numbers L995-0405 or L995-0386 of Appendix I.

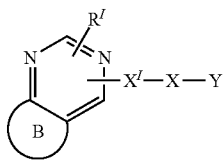

Formula I

In one embodiment the compounds of the present invention for use in the methods of the present invention are represented by Formula I wherein:
R' is —H or optionally substituted alkyl or cycloalkyl;
B is optionally substituted cycloalkyl, heterocycloalkyl, aryl or heteroaryl;
X' is optionally substituted heterocycloalkyl, —NR*— or —S—; in one embodiment X' is optionally substituted nitrogen containing heterocycloalkyl, —NR*— or —S—;
X is absent or an optionally substituted C1-C10 alkylenyl wherein optionally one or more carbon atoms are each independently replaced by —O—, —S—, —C(O)—, —NR*—, —S(O)$_2$— or optionally substituted heterocycloalkyl; in one embodiment X is an optionally substituted C1-C10 alkylenyl wherein optionally one or more carbon atoms are each independently replaced by —O—, —S—, —C(O)—, —NR*—, —S(O)$_2$— or optionally substituted heterocycloalkyl; in one embodiment X is an optionally substituted C1-C10 alkylenyl wherein one or more carbon atoms are each independently replaced by —O—, —S—, —C(O)—, —NR*—, —S(O)$_2$— or optionally substituted heterocycloalkyl;
Y is absent or optionally substituted cycloalkyl, aryl or heteroaryl; in one embodiment Y is optionally substituted cycloalkyl, aryl or heteroaryl; in one embodiment Y is optionally substituted aryl or heteroaryl; and each R* is independently —H or optionally substituted C1-C6 alkyl;

optionally X is absent and X' and Y combine to form an optionally substituted bicyclic fused ring.

In one embodiment, in the compounds and methods of the present invention X and Y cannot both be absent.

In one embodiment, in the compounds and methods of the present invention:
R' is —H or optionally substituted C1-C6 alkyl or cycloalkyl;
B is optionally substituted cyclopentyl, cyclohexyl, cycloheptanyl, phenyl, naphthyl, pyridyl, pyrimidinyl, pyrazinyl, pyridazinyl, furanyl, thiophenyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzothiophenyl, benzofuranyl, bemzimidazolyl, benzodioxolyl, benzoxazolyl, benzoisoxazolyl, piperidinyl, piperazinyl, pyrrolidinyl, imidazolidinyl, pyrazolidinyl, morpholinyl, tetrahydrofuranyl, tetrahydrothiophenyl, tetrahydroquinolinyl, tetrahydroisoquinolinyl, azepanyl, diazepanyl, azepinyl or diazepinyl;
X' is optionally substituted piperidinyl, piperazinyl, morpholinyl, pyrrolidinyl, imidazolidinyl, pyrazolidinyl, azepanyl, diazepanyl, azepinyl, diazepinyl, —NR*— or —S—;
X is absent or an optionally substituted C1-C10 alkylenyl wherein optionally one or more carbon atoms are each independently replaced by —O—, —C(O)—, —NR*—, —S(O)$_2$—, or optionally substituted piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl; in one embodiment X is an optionally substituted C1-C10 alkylenyl wherein optionally one or more carbon atoms are each independently replaced by —O—, —C(O)—, —NR*—, —S(O)$_2$—, or optionally substituted piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl; in one embodiment X is an optionally substituted C1-C10 alkylenyl wherein one or more carbon atoms are each independently replaced by —O—, —C(O)—, —NR*—, —S(O)$_2$—, or optionally substituted piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl;
Y is absent or optionally substituted cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl; in one embodiment Y is an optionally substituted cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl; and each R* is independently —H or optionally substituted C1-C6 alkyl;

optionally X is absent and X' and Y combine to form an optionally substituted bicyclic fused ring.

In one embodiment, in the compounds of the present invention either X or Y has to be present.

In one embodiment, in the compounds and methods of the present invention:

R' is —H or optionally substituted C1-C6 alkyl; in one embodiment R' is —H or C1-C6 alkyl;

B is optionally substituted cyclopentyl, phenyl, furanyl, thiophenyl, pyrrolyl, imidazolyl, pyrazolyl isooxazolyl or benzofuranyl;

X' is optionally substituted piperidinyl, piperazinyl, morpholinyl, pyrrolidinyl, imidazolidinyl, pyrazolidinyl, azepanyl, diazepanyl, azepinyl, diazepinyl, —NR*— or —S—;

X is absent or an optionally substituted C1-C6 alkylenyl wherein optionally one or more carbon atoms are each independently replaced by —O—, —C(O)—, —NR*—, —S(O)$_2$— or optionally substituted piperidinyl, piperazinyl, morpholinyl, pyrrolidinyl, imidazolidinyl or pyrazolidinyl; in one embodiment X is an optionally substituted C1-C6 alkylenyl wherein optionally one or more carbon atoms are each independently replaced by —O—, —C(O)—, —NR*—, —S(O)$_2$— or optionally substituted piperidinyl, piperazinyl, morpholinyl, pyrrolidinyl, imidazolidinyl or pyrazolidinyl; in one embodiment X is an optionally substituted C1-C6 alkylenyl wherein one or more carbon atoms are each independently replaced by —O—, —C(O)—, —NR*—, —S(O)$_2$— or optionally substituted piperidinyl, piperazinyl, morpholinyl, pyrrolidinyl, imidazolidinyl or pyrazolidinyl;

Y is absent or optionally substituted cyclopentyl, cyclohexyl, cycloheptanyl, phenyl, pyridyl, thiophenyl, furanyl, pyrrolyl, imidazolyl, pyrazolyl, quinolinyl, isoquinolinyl, bemzimidazolyl, benxothiophenyl, benzofuranyl or benzodioxolyl; in one embodiment Y is optionally substituted cyclopentyl, cyclohexyl, cycloheptanyl, phenyl, pyridyl, thiophenyl, furanyl, pyrrolyl, imidazolyl, pyrazolyl, quinolinyl, isoquinolinyl, bemzimidazolyl, benxothiophenyl, benzofuranyl or benzodioxolyl; and each R* is independently —H or optionally substituted C1-C6 alkyl; in one embodiment each R* is independently —H or C1-C6 alkyl;

optionally X is absent and X' and Y combine to form tetrahydroquinolinyl, tetrahydroisoquinolinyl, tetrahydrothienopyridinyl, benzoazapanyl or benzodiazepanyl.

In one embodiment, in the compounds and methods of the present invention either X or Y has to be present.

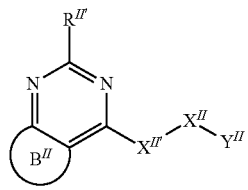

Formula II

In one embodiment the compounds of the present invention for use in the methods of the present invention are represented by Formula II wherein:

$R^{II'}$ is —H or optionally substituted alkyl or cycloalkyl;

$B^{II}$ is optionally substituted cycloalkyl, heterocycloalkyl, aryl or heteroaryl;

$X^{II'}$ is optionally substituted heterocycloalkyl or —NR*— or —S—; in one embodiment X' is optionally substituted nitrogen containing heterocycloalkyl, —NR*— or —S—;

$X^{II}$ is absent or an optionally substituted C1-C10 alkylenyl wherein optionally one or more carbon atoms are each independently replaced by —O—, —S—, —C(O)—, —NR*—, —S(O)$_2$— or optionally substituted heterocycloalkyl; in one embodiment $X^{II}$ is an optionally substituted C1-C10 alkylenyl wherein optionally one or more carbon atoms are each independently replaced by —O—, —S—, —C(O)—, —NR*—, —S(O)$_2$— or optionally substituted heterocycloalkyl; in one embodiment $X^{II}$ is an optionally substituted C1-C10 alkylenyl wherein one or more carbon atoms are each independently replaced by —O—, —S—, —C(O)—, —NR*—, —S(O)$_2$— or optionally substituted heterocycloalkyl;

Y is absent or optionally substituted cycloalkyl, aryl or heteroaryl; in one embodiment Y is optionally substituted cycloalkyl, aryl or heteroaryl; in one embodiment Y is optionally substituted aryl or heteroaryl; and each R* is independently —H or optionally substituted C1-C6 alkyl;

optionally X is absent and X' and Y combine to form an optionally substituted bicyclic fused ring.

In one embodiment, in the compounds and methods of the present invention X and Y cannot both be absent.

In one embodiment, in the compounds and methods of the present invention:

$R^{II'}$ is —H or optionally substituted C1-C6 alkyl or cycloalkyl;

$B^{II}$ is optionally substituted cyclopentyl, cyclohexyl, cycloheptanyl, phenyl, naphthyl, pyridyl, pyrimidinyl, pyrazinyl, pyridazinyl, furanyl, thiophenyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzothiophenyl, benzofuranyl, bemzimidazolyl, benzodioxolyl, benzoxazolyl, benzoisoxazolyl, piperidinyl, piperazinyl, pyrrolidinyl, imidazolidinyl, pyrazolidinyl, morpholinyl, tetrahydrofuranyl, tetrahydrothiophenyl, tetrahydroquinolinyl, tetrahydroisoquinolinyl, azepanyl, diazepanyl, azepinyl or diazepinyl;

$X^{II'}$ is —NR*—, —S—, or optionally substituted piperidinyl, piperazinyl, morpholinyl, pyrrolidinyl, imidazolidinyl, pyrazolidinyl, azepanyl, diazepanyl, azepinyl or diazepinyl;

$X^{II}$ is absent or an optionally substituted C1-C10 alkylenyl wherein optionally one or more carbon atoms are each independently replaced by —O—, —C(O)—, —NR*—, —S(O)$_2$—, or optionally substituted piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl; in one embodiment $X^{II}$ is an optionally substituted C1-C10 alkylenyl wherein optionally one or more carbon atoms are each independently replaced by —O—, —C(O)—, —NR*—, —S(O)$_2$—, or optionally substituted piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl; in one embodiment $X^{II}$ is an optionally substituted C1-C10 alkylenyl wherein one or more carbon atoms are each independently replaced by —O—, —C(O)—, —NR*—, —S(O)$_2$—, or optionally substituted piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl;

$Y^{II}$ is absent or optionally substituted cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl; in one embodiment $Y^{II}$ is optionally substituted cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl; and each R* is independently —H or optionally substituted C1-C6 alkyl; in one embodiment each R* is independently —H or C1-C6 alkyl;

optionally wherein $X^{II}$ is absent $X^{II'}$ and $Y^{II}$ combine to form tetrahydroquniolinyl, tetrahydroisoquniolinyl, tetrahydrothienopyridinyl, benzoazapanyl, or benzodiazepanyl.

In one embodiment, in the compounds and methods of the present invention:

$R^{II'}$ is —H or optionally substituted C1-C6 alkyl or cycloalkyl; in one embodiment $R^{II'}$ is —H or C1-C6 alkyl or cycloalkyl;

$B^{II}$ is cyclopentyl, cyclohexyl, cycloheptanyl, phenyl, naphthyl, pyridyl, pyrimidinyl, pyrazinyl, pyridazinyl, furanyl, thiophenyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzothiophenyl, benzofuranyl, bemzimidazolyl, benzodioxolyl, benzoxazolyl, benzoisoxazolyl, piperidinyl, piperazinyl, pyrrolidinyl, imidazolidinyl, pyrazolidinyl, morpholinyl, tetrahydrofuranyl, tetrahydrothiophenyl, tetrahydroquinolinyl, tetrahydroisoquinolinyl, azepanyl, diazepanyl, azepinyl or diazepinyl each optionally and independently substituted with one or more $R^{BII}$;

$X^{II'}$ is —NR*—, —S—, piperidinyl, piperazinyl, morpholinyl, pyrrolidinyl, imidazolidinyl, pyrazolidinyl, azepanyl, diazepanyl, azepinyl or diazepinyl each optionally and independently substituted with one or more $R^{XII'}$;

$X^{II}$ is absent or an C1-C10 alkylenyl wherein optionally one or more carbon atoms are each independently replaced by —O—, —C(O)—, —NR*—, —S(O)$_2$—, piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl and wherein the alkylenyl or heterocycloalkyl is optionally and independently substituted with one or more $R^{XII}$; in one embodiment $X^{II}$ is an optionally substituted C1-C10 alkylenyl wherein optionally one or more carbon atoms are each independently replaced by —O—, —C(O)—, —NR*—, —S(O)$_2$—, or piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl and wherein the alkylenyl or heterocycloalkyl is optionally and independently substituted with one or more $R^{XII}$; in one embodiment $X^{II}$ is an optionally substituted C1-C10 alkylenyl wherein one or more carbon atoms are each independently replaced by —O—, —C(O)—, —NR*—, —S(O)$_2$—, or piperidinyl, piperazinyl, morpholinyl, pyrrolidinyl, imidazolidinyl, pyrazolidinyl, tetrahydroquinolinyl, tetrahydroisoquinolinyl, azepanyl, diazepanyl, azepinyl or diazepinyl and wherein the alkylenyl or heterocycloalkyl is optionally and independently substituted with one or more $R^{XII}$;

$Y^{II}$ is absent or cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl each optionally and independently substituted with one or more $R^{YII}$; in ne embodiment $Y^{II}$ is cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl each optionally and independently substituted with one or more $R^{YII}$;

each R* is independently —H or optionally substituted C1-C6 alkyl; in one embodiment each R* is independently —H or C1-C6 alkyl;

optionally wherein $X^{II}$ is absent $X^{II'}$ and $Y^{II}$ combine to form tetrahydroquniolinyl, tetrahydroisoquniolinyl, tetrahydrothienopyridinyl, benzoazapanyl, or benzodiazepanyl;

each $R^{BII}$ is independently C1-C6 alkyl, C1-C6 haloalkyl, halo, —CN, or aryl;

each $R^{XII'}$ is independently C1-C6 alkyl, C1-C6 haloalkyl, halo or —CN;

each $R^{XII}$ is independently C1-C6 alkyl, C1-C6 haloalkyl, halo, —CN, cycloalkyl, or —NR*$_2$; and each $R^{YII}$ is independently C1-C6 alkyl, C1-C6 haloalkyl, —O(C1-C6 alkyl), —C(O)(C1-C6 alkyl), halo, —CN, —C1-C6 alkyl-NR*$_2$, heterocycloalkyl or heteocycloalkylalkyl.

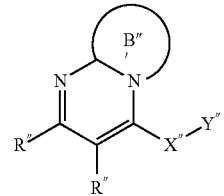

Formula III

In one embodiment the compounds of the present invention for use in the methods of the present invention are represented by Formula III wherein:

each R" is independently —H or optionally substituted C1-C6 alkyl, cycloalkyl or heterocycloalkyl;

B" is optionally substituted heterocycloalkyl or heteroaryl;

X" is absent or optionally substituted C1-C10 alkylenyl wherein one or more carbon atoms are optionally replaced by —O—, —S—, —NR*—, —C(O)—, —S(O)$_2$— or optionally substituted heterocycloalkyl; in one embodiment X" is absent optionally substituted C1-C10 alkylenyl wherein one or more carbon atoms are replaced by —O—, —S—, —NR*—, —C(O)—, —S(O)$_2$— or optionally substituted heterocycloalkyl; in one embodiment X" is optionally substituted C1-C10 alkylenyl wherein one or more carbon atoms are optionally replaced by —O—, —S—, —NR*—, —C(O)—, —S(O)$_2$— or optionally substituted heterocycloalkyl; in one embodiment X" is optionally substituted C1-C10 alkylenyl wherein one or more carbon atoms are replaced by —O—, —S—, —NR*—, —C(O)—, —S(O)$_2$— or optionally substituted heterocycloalkyl;

Y" is absent or optionally substituted cycloalkyl, aryl or heteroaryl; in one embodiment Y" is optionally substituted cycloalkyl, aryl or heteroaryl; in one embodiment Y" is optionally substituted aryl or heteroaryl; and each R* is independently —H or optionally substituted C1-C6 alkyl;

optionally wherein X" and Y" combine to form an optionally substituted bicyclic fused ring.

In one embodiment, in the compounds and methods of the present invention:

each R" is independently —H or optionally substituted C1-C6 alkyl or cycloalkyl;

B" is optionally substituted heteroaryl; in one embodiment B" is optionally substituted pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, indolyl, isoindolyl, indazolyl, azaindolyl, quinolinyl, isoquinolinyl, azaacenaphthylenyl, benzothiophenyl, benzofuranyl, benzimidazolyl, benzoxazolyl, benzoisoxazolyl, benzothiazolyl, benzoisothiazolyl, indolinyl, tetrahydroquinolinyl, tetrahydroisoquinolinyl, benzodioxolyl, piperidinyl, piperazinyl, morpholinyl, pyrrolidinyl, imidazolidinyl, pyrazolidinyl, azepanyl, diazepanyl, azepinyl, diazepinyl, thiazinyl, oxazinyl, tetrahydrothiazolyl, tetrahydroxazolyl; in one embodiment B" is optionally substituted pyridyl, pyrimidinyl, pyrazinyl, pyridazinyl, pyrrolyl, imidazolyl, pyrazolyl or triazolyl; in one embodiment B" is optionally substituted triazolyl; in one embodiment B" is triazolyl;

X" is absent or optionally substituted C1-C10 alkylenyl wherein one or more carbon atoms are independently replaced by —NR*—, —C(O)—, or optionally substituted piperidinyl, piperazinyl, morpholinyl, pyrrolidinyl, imidazolidinyl, pyrazolidinyl, azepanyl, diazepanyl, azepinyl or diazepinyl; in one embodiment X" is optionally substituted C1-C10 alkylenyl wherein one or more carbon atoms are independently replaced by —NR*—, —C(O)—, or optionally substituted piperidinyl, piperazinyl, morpholinyl, pyrrolidinyl, imidazolidinyl, pyrazolidinyl, azepanyl, diazepanyl, azepinyl or diazepinyl;

Y" is absent or optionally substituted cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl; in one embodiment Y" is optionally substituted cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl; and each R* is independently —H or optionally substituted C1-C6 alkyl.

In one embodiment, in the compounds and methods of the present invention:

each R" is independently —H or optionally substituted C1-C6 alkyl; in one embodiment each R" is independently —H or C1-C6 alkyl;

B" is optionally substituted triazolyl;

X" is optionally substituted C1-C5 alkylenyl wherein one or more carbon atoms is replaced by —NR*—;

Y" is optionally substituted cyclopentyl, cyclohexyl, cycloheptanyl phenyl, pyridyl, thiophenyl, furanyl or pyrazolyl; and each R* is independently —H or optionally substituted C1-C6 alkyl.

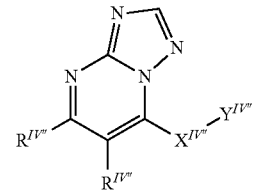

Formula IV

In one embodiment the compounds of the present invention for use in the methods of the present invention are represented by Formula IV wherein:

each $R^{IV"}$ is independently —H or optionally substituted C1-C6 alkyl, cycloalkyl or heterocycloalkyl;

$X^{IV"}$ absent or optionally substituted C1-C10 alkylenyl wherein one or more carbon atoms are optionally replaced by —O—, —S—, —NR*—, —C(O)—, —S(O)$_2$— or optionally substituted heterocycloalkyl; in one embodiment $X^{IV"}$ is absent or optionally substituted C1-C10 alkylenyl wherein one or more carbon atoms are replaced by —O—, —S—, —NR*—, —C(O)—, —S(O)$_2$— or optionally substituted heterocycloalkyl; in one embodiment $X^{IV"}$ optionally substituted C1-C10 alkylenyl wherein one or more carbon atoms are optionally replaced by —O—, —S—, —NR*—, —C(O)—, —S(O)$_2$— or optionally substituted heterocycloalkyl; in one embodiment $X^{IV"}$ is optionally substituted C1-C10 alkylenyl wherein one or more carbon atoms are replaced by —O—, —S—, —NR*—, —C(O)—, —S(O)$_2$— or optionally substituted heterocycloalkyl;

$Y^{IV"}$ is absent or optionally substituted cycloalkyl, aryl or heteroaryl; in one embodiment Y" is optionally substituted cycloalkyl, aryl or heteroaryl; in one embodiment $Y^{IV"}$ is optionally substituted aryl or heteroaryl; and each R* is independently —H or optionally substituted C1-C6 alkyl;
optionally wherein $X^{IV"}$ and $Y^{IV"}$ combine to form an optionally substituted bicyclic fused ring.

In one embodiment, in the compounds and methods of the present invention:
- each $R^{IV"}$ is independently —H or optionally substituted C1-C6 alkyl or cycloalkyl;
- $X^{IV"}$ is absent or optionally substituted C1-C10 alkylenyl wherein one or more carbon atoms are independently replaced by —NR*—, —C(O)—, or optionally substituted piperidinyl, piperazinyl, morpholinyl, pyrrolidinyl, imidazolidinyl, pyrazolidinyl, azepanyl, diazepanyl, azepinyl or diazepinyl; in one embodiment $X^{IV"}$ is optionally substituted C1-C10 alkylenyl wherein one or more carbon atoms are independently replaced by —NR*—, —C(O)—, or optionally substituted piperidinyl, piperazinyl, morpholinyl, pyrrolidinyl, imidazolidinyl, pyrazolidinyl, azepanyl, diazepanyl, azepinyl or diazepinyl;
- $Y^{IV"}$ is absent optionally substituted cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl; in one embodiment $Y^{IV"}$ is optionally substituted cyclopentyl, cyclohexyl, cycloheptanyl, phenyl, naphthyl, pyridyl, pyrimidinyl, pyridazinyl, pyrazinyl, thiophenyl, furanyl, pyrrolyl, imidazolyl, pyrazolyl, triazolyl, oxazolyl, isoxazolyl, thiazolyl, isothiazolyl, indolyl, isoindolyl, indolinyl, indazolyl, azaindolyl, quinolinyl, isoquinolinyl, benzoxazolyl, benzoisoxazolyl, bemzimidazolyl, benxothiophenyl, benzofuranyl or benzodioxolyl; and
- each R* is independently —H or optionally substituted C1-C6 alkyl.

In one embodiment, in the compounds and methods of the present invention:
- each $R^{IV"}$ is independently —H or optionally substituted C1-C6 alkyl;
- $X^{IV"}$ is optionally substituted C1-C5 alkylene wherein one or more carbon atoms is replaced by —NR*—;
- $Y^{IV"}$ is optionally substituted cyclopentyl, cyclohexyl, cycloheptanyl, phenyl, pyridyl, thiophenyl, furanyl or pyrazolyl; and
- each R* is independently —H or optionally substituted C1-C6 alkyl;

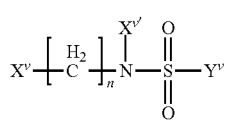

Formula V

In one embodiment the compounds of the present invention for use in the methods of the present invention are represented by Formula V wherein:
- $X^{V'}$ is —H or optionally substituted alkyl, or together with the nitrogen to which it is attached and $X^V$ forms an optionally substituted heterocyloalkyl ring;
- $X^V$ is optionally substituted aryl, heteroaryl, cycloalkyl or heterocycloalkyl;
- $Y^V$ is optionally substituted aryl or heteroaryl; and
- n is 0, 1, 2, 3, 4, 5, or 6.

In one embodiment, in the compounds and methods of the present invention:
- $X^{V'}$ is —H or optionally substituted alkyl, or together with the nitrogen to which it is attached and $X^V$ forms an optionally substituted piperidinyl, piperazinyl, morpholinyl, pyrrolidinyl, imidazolidinyl, pyrazolidinyl, azepanyl, diazepanyl, azepinyl, diazepinyl, thiazinyl, oxazinyl, indolinyl, benzodioxolyl, tetrahydroquinolinyl, tetrahydroisoquinolinyl, tetrahydrothiazolyl or tetrahydroxazolyl;
- $X^V$ is optionally substituted cyclopropyl, cyclobutyl, cyclopentyl, cyclohexyl, cycloheptanyl, phenyl, naphthyl, acenaphthylenyl pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, indolyl, isoindolyl, indolinyl, indazolyl, azaindolyl, quinolinyl, isoquinolinyl, azaacenaphthylenyl, furanyl, thiophenyl, benzodioxolyl, benzothiophenyl, benzofuranyl, benzimidazolyl, benzoxazolyl, benzoisoxazolyl, benzothiazolyl, benzoxazolyl, piperidinyl, piperazinyl, morpholinyl, pyrrolidinyl, imidazolidinyl, pyrazolidinyl, azepanyl, diazepanyl, azepinyl, diazepinyl, thiazinyl, oxazinyl, tetrahydroquinolinyl, tetrahydroisoquinolinyl, tetrahydrofuranyl, tetrahydrothiophenyl, tetrahydrothiazolyl or tetrahydroxazolyl;
- $Y^V$ is optionally substituted phenyl, naphthyl, acenaphthylenyl pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, indolyl, isoindolyl, indolinyl, indazolyl, azaindolyl, quinolinyl, isoquinolinyl, azaacenaphthylenyl, furanyl, thiophenyl, benzodioxolyl, benzothiophenyl, benzofuranyl, benzimidazolyl, benzoxazolyl, benzoisoxazolyl, benzothiazolyl or benzoxazolyl; and
- n is 0, 1, 2, 3, 4, 5, or 6.

In one embodiment, in the compounds and methods of the present invention:
- $X^{V'}$ is —H or together with the nitrogen to which it is attached and $X^V$ forms an optionally substituted tetrahydrathiazolyl, piperazinyl pyrrolidinyl or indolinyl;
- $X^V$ is optionally substituted phenyl, pyridyl, pyrimidinyl, pyrazinyl, piperidinyl, pyrrolyl, imidazolyl, thiophenyl, furanyl, thiazolyl, isothiazolyl, oxazolyl, isoxazolyl, tetrahydrothiazolyl, tetrahydrofuranyl, tetrahydrothiophenyl, benzothiazolyl, benzofuranyl, indolinyl, indolyl, indazolyl, benzimidazolyl, benzimidazolonyl, dihydrobenzimidazolonyl, benzodioxolanyl, piperidinyl, piperazinyl, pyrrolidinyl, imidazolidinyl, pyrazolidinyl, tetrahydroquinolinyl, tetrahydroisoquinolinyl, tetrahydrofuranyl, tetrahydrothiophenyl, tetrahydrothiazolyl or tetrahydroxazolyl;
- $Y^V$ is optionally substituted phenyl, naphthyl, pyridyl, pyrimidinyl, pyridazinyl, pyrazinyl, thiophenyl, furanyl, pyrrolyl, imidazolyl, pyrazolyl, triazolyl, naphthalenyl, quinolinyl, isoquinolinyl, tetrahydroquinolinyl, tetrahydraisoquinolinyl, indolinyl, indolyl, benzimidazolyl, benzofuranyl, benzothiophenyl, benzoisoxazolyl, benzothiazolyl, tetrahydrothienopyridinyl, acenaphthylenyl, benzoindolyl or benzoindolonyl;
- each R* is independently —H or optionally substituted C1-C6 alkyl; and n is 0, 1, 2, 3, 4, 5, or 6.

Formula VI

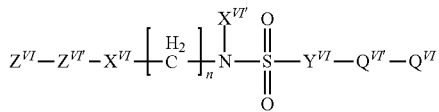

In one embodiment the compounds of the present invention for use in the methods of the present invention are represented by Formula VI wherein:
- $X^{VI'}$ is —H or optionally substituted alkyl, or together with the nitrogen to which it is attached and $X^{VI}$ forms an optionally substituted heterocyloalkyl ring;
- $X^{VI}$ is optionally substituted aryl, heteroaryl, cycloalkyl or heterocycloalkyl;
- $Y^{VI}$ is optionally substituted aryl or heteroaryl;
- $Z^{VI}$ is absent or an optionally substituted C1-C10 alkylenyl or alkenylenyl wherein one or more carbon atoms are independently replaced by —NR*— or —C(O)—
- $Z^{VI}$ is absent or an optionally substituted aryl, heteroaryl, cycloalkyl or heterocycloalkyl;
- $Q^{VI'}$ is absent or an optionally substituted C1-C10 alkylenyl or alkenylenyl wherein one or more carbon atoms are independently replaced by —NR*— or —C(O)—;
- $Q^{VI}$ is absent or an optionally substituted aryl, heteroaryl, cycloalkyl or heterocycloalkyl;
- each R* is independently —H or optionally substituted C1-C6 alkyl; and
- n is 0, 1, 2, 3, 4, 5, or 6;
- wherein only one of $Z^{VI}$ or $Q^{VI}$ can be absent.

In one embodiment, in the compounds and methods of the present invention:
- $X^{VI'}$ is —H or optionally substituted alkyl, or together with the nitrogen to which it is attached and $X^{V}$ forms an optionally substituted piperidinyl, piperazinyl, morpholinyl, pyrrolidinyl, imidazolidinyl, pyrazolidinyl, azepanyl, diazepanyl, azepinyl, diazepinyl, thiazinyl, oxazinyl, indolinyl, tetrahydroquinolinyl, tetrahydroisoquinolinyl, tetrahydrothiazolyl or tetrahydroxazolyl;
- $X^{VI}$ is optionally substituted cyclopropyl, cyclobutyl, cyclopentyl, cyclohexyl, cycloheptanyl, phenyl, naphthyl, acenaphthylenyl pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, indolyl, isoindolyl, indolinyl, indazolyl, azaindolyl, quinolinyl, isoquinolinyl, azaacenaphthylenyl, furanyl, thiophenyl, benzodioxolyl, benzothiophenyl, benzofuranyl, benzimidazolyl, benzoxazolyl, benzoisoxazolyl, benzothiazolyl, benzoxazolyl, piperidinyl, piperazinyl, morpholinyl, pyrrolidinyl, imidazolidinyl, pyrazolidinyl, azepanyl, diazepanyl, azepinyl, diazepinyl, thiazinyl, oxazinyl, tetrahydroquinolinyl, tetrahydroisoquinolinyl, tetrahydrofuranyl, tetrahydrothiophenyl, tetrahydrothiazolyl or tetrahydroxazolyl;
- $Y^{VI}$ is optionally substituted phenyl, naphthyl, acenaphthylenyl pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, indolyl, isoindolyl, indolinyl, indazolyl, azaindolyl, quinolinyl, isoquinolinyl, azaacenaphthylenyl, furanyl, thiophenyl, benzodioxolyl, benzothiophenyl, benzofuranyl, benzimidazolyl, benzoxazolyl, benzoisoxazolyl, benzothiazolyl or benzoxazolyl;
- $Z^{VI'}$ is absent or an optionally substituted C1-C10 alkylenyl or alkenylenyl wherein one or more carbon atoms are independently replaced by —NR*— or —C(O)—;
- $Z^{VI}$ is absent or an optionally substituted cyclopropyl, cyclobutyl, cyclopentyl, cyclohexyl, cycloheptanyl, phenyl, naphthyl, acenaphthylenyl, pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, indolyl, isoindolyl, indolinyl, indazolyl, azaindolyl, quinolinyl, isoquinolinyl, azaacenaphthylenyl, furanyl, thiophenyl, benzodioxolyl, benzothiophenyl, benzofuranyl, benzimidazolyl, benzoxazolyl, benzoisoxazolyl, benzothiazolyl, benzoxazolyl, piperidinyl, piperazinyl, morpholinyl, pyrrolidinyl, imidazolidinyl, pyrazolidinyl, azepanyl, diazepanyl, azepinyl, diazepinyl, thiazinyl, oxazinyl, tetrahydroquinolinyl, tetrahydroisoquinolinyl, tetrahydrofuranyl, tetrahydrothiophenyl, tetrahydrothiazolyl or tetrahydroxazolyl;
- $Q^{VI'}$ is absent or an optionally substituted C1-C10 alkylenyl or alkenylenyl wherein one or more carbon atoms are independently replaced by —NR*— or —C(O)—;
- $Q^{VI}$ is absent or an optionally substituted cyclopropyl, cyclobutyl, cyclopentyl, cyclohexyl, cycloheptanyl, phenyl, naphthyl, acenaphthylenyl, pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, indolyl, isoindolyl, indolinyl, indazolyl, azaindolyl, quinolinyl, isoquinolinyl, azaacenaphthylenyl, furanyl, thiophenyl, benzodioxolyl, benzothiophenyl, benzofuranyl, benzimidazolyl, benzoxazolyl, benzoisoxazolyl, benzothiazolyl, benzoxazolyl, piperidinyl, piperazinyl, morpholinyl, pyrrolidinyl, imidazolidinyl, pyrazolidinyl, azepanyl, diazepanyl, azepinyl, diazepinyl, thiazinyl, oxazinyl, tetrahydroquinolinyl, tetrahydroisoquinolinyl, tetrahydrofuranyl, tetrahydrothiophenyl, tetrahydrothiazolyl or tetrahydroxazolyl;
- each R* is independently —H or optionally substituted C1-C6 alkyl; and
- n is 0, 1, 2, 3, 4, 5, or 6;
- wherein only one of $Z^{VI}$ or $Q^{VI}$ can be absent.

In one embodiment, in the compounds and methods of the present invention:
- $X^{VI'}$ is —H or optionally substituted alkyl, or together with the nitrogen to which it is attached and $X^{V}$ forms an optionally substituted tetrahydrathiazolyl, piperazinyl pyrrolidinyl or indolinyl;
- $X^{VI}$ is optionally substituted phenyl, pyridyl, pyrimidinyl, pyrazinyl, piperidinyl, pyrrolyl, imidazolyl, thiophenyl, furanyl, thiazolyl, isothiazolyl, oxazolyl, isoxazolyl, tetrahydrothiazolyl, tetrahydrofuranyl, tetrahydrothiophenyl, benzothiazolyl, benzofuranyl, indolinyl, indolyl, indazolyl, benzimidazolyl, benzimidazolonyl, dihydrobenzimidazolonyl, benzodioxolanyl, piperidinyl, piperazinyl, pyrrolidinyl, imidazolidinyl, pyrazolidinyl, tetrahydroquinolinyl, tetrahydroisoquinolinyl, tetrahydrofuranyl, tetrahydrothiophenyl, tetrahydrothiazolyl or tetrahydroxazolyl;
- $Y^{VI}$ is optionally substituted phenyl, naphthyl, pyridyl, pyrimidinyl, pyridazinyl, pyrazinyl, thiophenyl, furanyl, pyrrolyl, imidazolyl, pyrazolyl, triazolyl, naphthalenyl, quinolinyl, isoquinolinyl, tetrahydroquinolinyl, tetrahydraisoquinolinyl, indolinyl, indolyl, benzimidazolyl, benzofuranyl, benzothiophenyl, benzoisoxazolyl, benzothiazolyl, tetrahydrothienopyridinyl, acenaphthylenyl, benzoindolyl or benzoindolonyl;

$Z^{VI'}$ is absent or an optionally substituted C1-C10 alkylenyl or alkenylenyl wherein one or more carbon atoms are independently replaced by —NR*— or —C(O)—

$Z^{VI}$ is absent or an optionally substituted cyclopropyl, cyclobutyl, cyclopentyl, cyclohexyl, cycloheptanyl, phenyl, pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, benzodioxolyl, benzothiophenyl, benzofuranyl, benzimidazolyl, benzoxazolyl, benzoisoxazolyl, benzothiazolyl, benzoxazolyl, piperidinyl, piperazinyl, morpholinyl, pyrrolidinyl, imidazolidinyl, pyrazolidinyl, thiazinyl, thiazinyldioxidyl, oxazinyl, tetrahydrofuranyl or tetrahydrothiophenyl;

$Q^{VI'}$ is absent or an optionally substituted C1-C10 alkylenyl or alkenylenyl wherein one or more carbon atoms are independently replaced by —NR*— or —C(O)—;

$Q^{VI}$ is absent or an optionally substituted cyclopropyl, cyclobutyl, cyclopentyl, cyclohexyl, cycloheptanyl, phenyl, pyridyl, pyrimidinyl, pyrazinyl, pyridazinyl, pyrrolyl, imidazolyl, pyrazolyl, triazolyl, oxazolyl, oxadiazolyl, thiadiazolyl, isoxazolyl, thiazolyl, isothiazolyl, furanyl, thiophenyl, piperidinyl, piperazinyl, morpholinyl, pyrrolidinyl, pyrrolidinonyl, imidazolidinyl, pyrazolidinyl, thiazinyl, thiazinyldioxidyl, oxazinyl, tetrahydroquinolinyl, tetrahydroisoquinolinyl, tetrahydrofuranyl, tetrahydrothiophenyl, tetrahydrothiazolyl or tetrahydroxazolyl;

each R* is independently —H or optionally substituted C1-C6 alkyl; and n is 0, 1, 2, 3, 4, 5, or 6;

wherein only one of $Z^{VI}$ or $Q^{VI}$ can be absent.

In one embodiment, in the compounds and methods of the present invention:

$X^{VI'}$ is —H or together with the nitrogen to which it is attached and $X^{VI}$ forms an optionally substituted tetrahydrathiazolyl, piperazinyl, pyrrolidinyl or indolinyl;

$X^{VI}$ is phenyl, pyridyl, pyrimidinyl, pyrazinyl, piperidinyl, pyrrolyl, imidazolyl, thiophenyl, furanyl, thiazolyl, isothiazolyl, oxazolyl, isoxazolyl, tetrahydrothiazolyl, tetrahydrofuranyl, tetrahydrothiophenyl, benzothiazolyl, benzofuranyl, indolinyl, indolyl, indazolyl, benzimidazolyl, benzimidazolonyl, dihydrobenzimidazolonyl, benzodioxolanyl, piperidinyl, piperazinyl, pyrrolidinyl, imidazolidinyl, pyrazolidinyl, tetrahydroquinolinyl, tetrahydroisoquinolinyl, tetrahydrofuranyl, tetrahydrothiophenyl, tetrahydrothiazolyl or tetrahydroxazolyl each independently optionally substituted with one or more $R^{XVI}$;

$Y^{VI}$ is phenyl, naphthyl, pyridyl, pyrimidinyl, pyridazinyl, pyrazinyl, thiophenyl, furanyl, pyrrolyl, imidazolyl, pyrazolyl, triazolyl, naphthalenyl, quinolinyl, isoquinolinyl, tetrahydroquinolinyl, tetrahydraisoquinolinyl, indolinyl, indolyl, benzimidazolyl, benzofuranyl, benzothiophenyl, benzoisoxazolyl, benzothiazolyl, tetrahydrothienopyridinyl, acenaphthylenyl, benzoindolyl or benzoindolonyl each independently optionally substituted with one or more $R^{YVI}$;

$Z^{VI'}$ is absent or an optionally substituted C1-C6 alkylenyl or alkenylenyl wherein one or more carbon atoms are independently replaced by —NR*— or —C(O)—;

$Z^{VI}$ is absent or cyclopropyl, phenyl, thiazolyl, pyridinyl, thiazinyl, thiazinyldioxidyl or benzothiazolyl each independently optionally substituted with one or more $R^{ZVI}$;

$Q^{VI'}$ is absent or an optionally substituted C1-C10 alkylenyl or alkenylenyl wherein one or more carbon atoms are independently replaced by —NR*— or —C(O)—;

$Q^{VI}$ is absent or an optionally substituted cyclopropyl, cyclobutyl, cyclopentyl, phenyl, oxadiazolyl, pyridyl, pyrazolyl, pyrrolidinyl, thiophenyl, furanyl, pyrrolidinonyl, thiazinyl, thiazinyldioxidyl, tetrahydrofuranyl each independently optionally substituted with one or more $R^{QVI}$;

each R* is independently —H or optionally substituted C1-C6 alkyl;

each $R^{XVI}$ is independently C1-C6 alkyl, C1-C6 alkenyl, C1-C6 haloalkyl, —O(C1-C6 alkyl), —O(C1-C6 haloalkyl), —S(C1-C6 alkyl), —S(C1-C6 haloalkyl), —SO$_2$(C1-C6 alkyl), —SO$_2$(C1-C6 haloalkyl), —SO$_2$NR*$_2$, —C(O)(C1-C6 alkyl), —C(O)(C1-C6 haloalkyl), cycloalkyl, aryl, heterocycloalkyl, aryl, —N(R*)C(O)R* —C(O)N(R*)$_2$, —NO$_2$, =O, halo or —CN; in one embodiment each $R^{XVI}$ is independently C1-C6 alkyl, C1-C6 alkenyl, C1-C6 haloalkyl, —O(C1-C6 alkyl), —O(C1-C6 haloalkyl), —S(C1-C6 alkyl), —S(C1-C6 haloalkyl), —SO$_2$(C1-C6 alkyl), —SO$_2$(C1-C6 haloalkyl), —SO$_2$NR*$_2$, —C(O)(C1-C6 alkyl), —C(O)(C1-C6 haloalkyl), cycloalkyl, —N(R*)C(O)R* —C(O)N(R*)$_2$, —NO$_2$, =O, halo or —CN; in one embodiment each $R^{XVI}$ is independently C1-C6 alkyl, C1-C6 alkenyl, C1-C6 haloalkyl, —O(C1-C6 alkyl), —S(C1-C6 alkyl), —SO$_2$(C1-C6 alkyl), —SO$_2$NR*$_2$, —C(O)(C1-C6 alkyl), cycloalkyl, —NO$_2$, =O, halo or —CN;

each $R^{YVI}$ is independently C1-C6 alkyl, C1-C6 alkenyl, C1-C6 haloalkyl, —O(C1-C6 alkyl), —O(C1-C6 haloalkyl), —S(C1-C6 alkyl), —S(C1-C6 haloalkyl), —SO$_2$(C1-C6 alkyl), —SO$_2$(C1-C6 haloalkyl), —SO$_2$NR*$_2$, —C(O)(C1-C6 alkyl), —C(O)(C1-C6 haloalkyl), cycloalkyl, aryl, heterocycloalkyl, aryl, —N(R*)C(O)R* —C(O)N(R*)$_2$, —NO$_2$, =O, halo or —CN; in one embodiment each $R^{XVI}$ is independently C1-C6 alkyl, C1-C6 alkenyl, C1-C6 haloalkyl, —O(C1-C6 alkyl), —O(C1-C6 haloalkyl), —S(C1-C6 alkyl), —S(C1-C6 haloalkyl), —SO$_2$(C1-C6 alkyl), —SO$_2$(C1-C6 haloalkyl), —SO$_2$NR*$_2$, —C(O)(C1-C6 alkyl), —C(O)(C1-C6 haloalkyl), cycloalkyl, —N(R*)C(O)R* —C(O)N(R*)$_2$, —NO$_2$, =O, halo or —CN; in one embodiment each $R^{XVI}$ is independently C1-C6 alkyl, C1-C6 alkenyl, C1-C6 haloalkyl, —O(C1-C6 alkyl), —S(C1-C6 alkyl), —SO$_2$(C1-C6 alkyl), —SO$_2$NR*$_2$, —C(O)(C1-C6 alkyl), cycloalkyl, —NO$_2$, =O, halo or —CN;

each $R^{ZVI}$ is independently C1-C6 alkyl, C1-C6 alkenyl, C1-C6 haloalkyl, —O(C1-C6 alkyl), —O(C1-C6 haloalkyl), —S(C1-C6 alkyl), —S(C1-C6 haloalkyl), —SO$_2$(C1-C6 alkyl), —SO$_2$(C1-C6 haloalkyl), —SO$_2$NR*$_2$, —C(O)(C1-C6 alkyl), —C(O)(C1-C6 haloalkyl), cycloalkyl, aryl, heterocycloalkyl, aryl, —N(R*)C(O)R* —C(O)N(R*)$_2$, —NO$_2$, =O, halo or —CN; in one embodiment each $R^{ZVI}$ is independently C1-C6 alkyl, C1-C6 alkenyl, C1-C6 haloalkyl, —O(C1-C6 alkyl), —O(C1-C6 haloalkyl), —S(C1-C6 alkyl), —S(C1-C6 haloalkyl), —SO$_2$(C1-C6 alkyl), —SO$_2$(C1-C6 haloalkyl), —SO$_2$NR*$_2$, —C(O)(C1-C6 alkyl), —C(O)(C1-C6 haloalkyl), cycloalkyl, —N(R*)C(O)R* —C(O)N(R*)$_2$, —NO$_2$, =O, halo or —CN; in one embodiment each $R^{XVI}$ is independently C1-C6 alkyl, C1-C6 alkenyl, C1-C6 haloalkyl, —O(C1-C6 alkyl), —S(C1-C6 alkyl), —SO$_2$(C1-C6 alkyl), —SO$_2$NR*$_2$, —C(O)(C1-C6 alkyl), cycloalkyl, —NO$_2$, =O, halo or —CN;

each R$^{QVI}$ is independently C1-C6 alkyl, C1-C6 alkenyl, C1-C6 haloalkyl, —O(C1-C6 alkyl), —O(C1-C6 haloalkyl), —S(C1-C6 alkyl), —S(C1-C6 haloalkyl), —SO$_2$(C1—C6 alkyl), —SO$_2$(C1-C6 haloalkyl), —SO$_2$NR*$_2$, —C(O)(C1-C6 alkyl), —C(O)(C1-C6 haloalkyl), cycloalkyl, aryl, heterocycloalkyl, aryl, —N(R*)C(O)R* —C(O)N(R*)$_2$, —NO$_2$, =O, halo or —CN; in one embodiment each R$^{QVI}$ is independently C1-C6 alkyl, C1-C6 alkenyl, C1-C6 haloalkyl, —O(C1-C6 alkyl), —O(C1-C6 haloalkyl), —S(C1-C6 alkyl), —S(C1-C6 haloalkyl), —SO$_2$(C1-C6 alkyl), —SO$_2$(C1-C6 haloalkyl), —SO$_2$NR*$_2$, —C(O)(C1-C6 alkyl), —C(O)(C1-C6 haloalkyl), cycloalkyl, —N(R*)C(O)R* —C(O)N(R*)$_2$, —NO$_2$, =O, halo or —CN; in one embodiment each R$^{XVI}$ is independently C1-C6 alkyl, C1-C6 alkenyl, C1-C6 haloalkyl, —O(C1-C6 alkyl), —S(C1-C6 alkyl), —SO$_2$(C1-C6 alkyl), —SO$_2$NR*$_2$, —C(O)(C1-C6 alkyl), cycloalkyl, —NO$_2$, =O, halo or —CN;

n is 0, 1, 2, 3, 4, 5, or 6;

wherein only one of Z$^{VI}$ or Q$^{VI}$ can be absent.

In one of the above embodiment, the structure is not any one or more of catalog ID numbers F228-0365, F228-0351, F228-0856, F228-0541, T5464782, F1462-0491, T5463709, 4052-4279, L287-1577, L287-1758, K404-0672, K404-0183, K404-0796, F0524-0511, F0524-0507, F0522-0533, F0524-0488, K404-0400, T0507-8442, K404-0906, K404-0842, K404-0852, K404-0914, K404-0915, K404-0828, K404-0863, K404-0277, T636-2007, T636-1250, T636-2391, T636-0054, T636-0027, T636-1243, T636-2360, T636-0085, T636-0181, D278-0514, T636-1715, T636-2144, T636-1601, T636-0973, T5436375, P025-0462, P025-0080, P025-0168, T5581430, F0376-0203, or T5246417 of Appendix I.

According to at least some embodiments, there is provided a pharmaceutical composition comprising the molecule as described above.

The above molecule or pharmaceutical composition may optionally be used as a medicament.

The above molecule or pharmaceutical composition may be used for treatment of a neurological disease, wherein the neurological disease includes ALS (Amyotrophic lateral sclerosis), a subtype thereof or a related disease. ALS subtypes include bulbar-onset ALS and limb-onset ALS. In addition to ALS and its subtypes, optionally the inventive molecules could be used for treatment of other types of MND including primary lateral sclerosis (PLS), progressive bulbar palsy and progressive muscular atrophy. Optionally the subtype includes bulbar-onset ALS or limb-onset ALS.

Optionally the related disease includes one of primary lateral sclerosis (PLS), progressive bulbar palsy or progressive muscular atrophy Optionally there is provided a method for treating a mammal in need of treatment thereof, comprising administering to the mammal an inventive molecule or a pharmaceutical composition as described above, for treatment of a neurological disease, wherein said neurological disease includes ALS (Amyotrophic lateral sclerosis) and its subtypes. ALS subtypes include bulbar-onset ALS and limb-onset ALS. In addition to ALS and its subtypes, optionally the inventive molecules could be used for treatment of other types of MND including primary lateral sclerosis (PLS), progressive bulbar palsy and progressive muscular atrophy.

According to at least some embodiments, there is provided an inventive molecule or a pharmaceutical composition comprising same, for treatment or prevention of a neurological disease, wherein said neurological disease includes ALS (Amyotrophic lateral sclerosis), a subtype thereof or a related disease in a subject in need thereof, wherein said molecule is selected from the group consisting of: Families A, C, E, F(7), F(6), G, I, M, PQRV, Y and Formulas I-VI as described herein.

According to at least some embodiments, there is provided an inventive molecule or a pharmaceutical composition comprising same, for treatment of a neurological disease, wherein said neurological disease includes ALS (Amyotrophic lateral sclerosis), a subtype thereof or a related disease, wherein said molecule is selected from the group consisting of:

an inventive molecule selected from the group consisting of Families A, C, E, F(7), F(6), G, I, M, PQRV, Y and Formulas I-VI as described herein;

wherein a molecule of Family A has the structure:

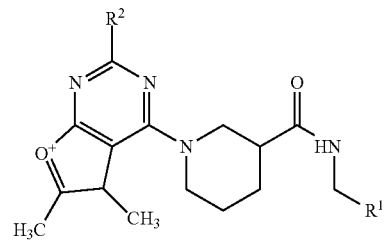

wherein R1 is H or benzyl unsubstituted or substituted with nitrogen, R2 is H or alkyl, preferably H, with the proviso that if R2 is H, R1 is not

and with the further proviso that the structure is not that of catalog ID numbers F228-0365, F228-0351, F228-0856 or F228-0541 of Appendix I;

wherein a molecule of Family C has the structure:

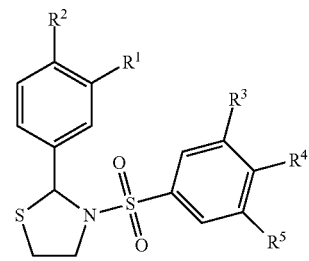

wherein R1 and R2 are each H or methoxy, preferably methoxy; each of R3, R4 and R5 are independently alkyl, preferably ethyl, or H; preferably only one of R3-R5 is alkyl, preferably ethyl, and the remainder are H; more preferably R4 is alkyl, most preferably ethyl, and R3 and R5 are H;

with the proviso that the structure is not that of catalog ID numbers T5464782, F1462-0491, T5463709 or 4052-4279 of Appendix I;

wherein a molecule of Family E has the structure:

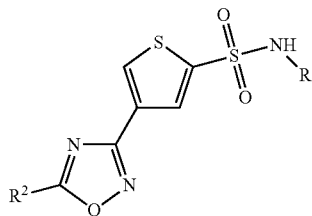

wherein R is pentyl, benzyl, alkyl benzyl or R1, preferably pentyl or R1; R2 is alkyl, cyclopentyl or cyclobutane; if R2 is alkyl, is preferably methyl or ethyl; wherein R1 is

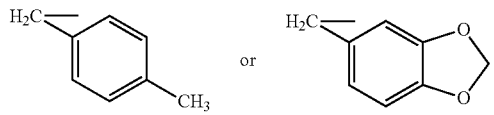

with the proviso that the structure is not that of catalog ID numbers L287-1577, or L287-1758 of Appendix I;
wherein a Family I has the structure:

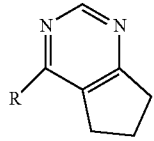

wherein for Family I, R is

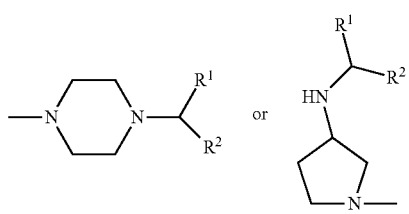

wherein for Family I, R1 is cyclopentadiene or benzene, unsubstituted or substituted with S, O or N; R2 is H or a carbonyl;
wherein for Family I, R1 is selected from the group consisting of (alternative atoms at each position are indicated in brackets)

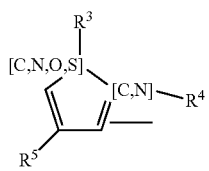

wherein each of R3, R4 and R5 is independently H, alkyl (preferably methyl);
and

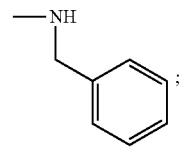

with the proviso that the structure is not that of catalog ID numbers T636-2007, T636-1250, T636-2391, T636-0054, T636-0027, T636-1243, T636-2360, T636-0085, T636-0181, D278-0514, T636-1715, T636-2144, T636-1601, or T636-0973 of Appendix I;
wherein a molecule of Family F(6) has the structure:

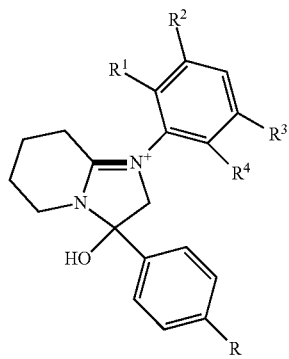

wherein for Family F(6) R is H, halogen, preferably F or Cl; alkyl, preferably methyl or ethyl; alkoxy, preferably methoxy or ethoxy;
R1, R2, R3 and R4 are each independently H, alkyl, preferably methyl or ethyl; alkoxy, preferably methoxy or ethoxy; with the proviso that if R1 is alkoxy, R is not alkyl and is preferably halogen or alkoxy;
with the proviso that the structure is not that of catalog ID numbers K404-0672, K404-0183, K404-0796, F0524-0511, F0524-0507, F0522-0533, F0524-0488, K404-0400, T0507-8442, K404-0906, K404-0842, K404-0852, K404-0914, K404-0915, K404-0828, K404-0863 or K404-0277 of Appendix I;
wherein a molecule of Family F(7) has the structure:

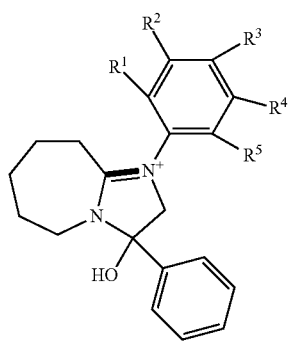

wherein R is alkyl, preferably ethyl or methyl, halogen, preferably Cl or F, H; alkoxy, preferably methoxy or ethoxy;

Each of R1-R5 is independently H, alkyl, preferably methyl; alkoxy, preferably methoxy or ethoxy;
with the proviso that the structure is not that of catalog ID numbers K404-0672, K404-0183, K404-0796, F0524-0511, F0524-0507, F0522-0533, F0524-0488, K404-0400, T0507-8442, K404-0906, K404-0842, K404-0852, K404-0914, K404-0915, K404-0828, K404-0863 or K404-0277 of Appendix I;
wherein a molecule of Family M has the structure.

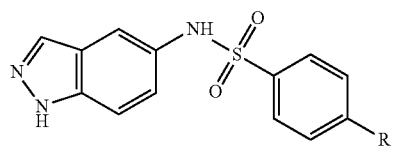

wherein R is H or alkyl; if alkyl, R is methyl or ethyl, unsubstituted or substituted with halogen (preferably F or Cl, more preferably F; preferably up to three halogens), more preferably ethyl;
with the proviso that the structure is not that of catalog ID number T5436375 of Appendix I;
wherein the Family PQRV has the structure (brackets indicate that the atom at that position can be C or N):

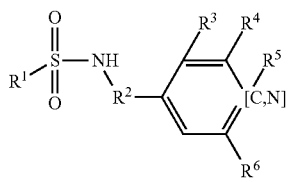

wherein R1 is benzyl,

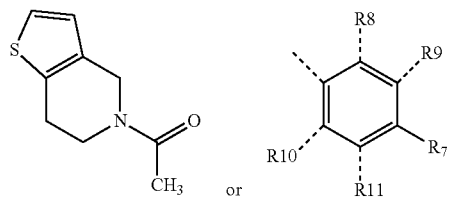

wherein R2 is alkyl, forms a heterocyclic hexyl moiety with the nitrogen to which it is attached, or is absent;
wherein each of R3, R4, R5 and R6 are halogen, H, alkyl, benzyl or alkyl benzyl (unsubstituted or substituted with nitrogen), cyclopentadiene or alky cyclopentadiene (substituted or unsubstituted with S or N) or carbamoyl (optionally alkyated with cyclopropane); R4 and R5 together can be cyclopentadiene, substituted with S and/or N, or unsubstituted, and optionally alkylated;
wherein each of R7-RT 1 is independently halogen, alkyl, or methoxy, and can be the same or different; or is pyrrolidine, optionally formyl pyrrolidine, in which case preferably R7 is pyrrolidine;
with the proviso that the structure is not that of catalog ID numbers P025-0462, P025-0080, P025-0168, T5581430, F0376-0203, or T5246417 of Appendix I;
wherein a molecule of Family Y has the structure:

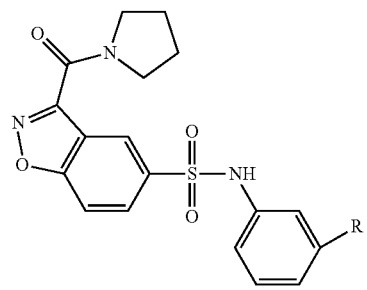

wherein R is alkyl, S or halogen, preferably S or halogen; if halogen, preferably F; if S, preferably methylthio or ethylthio, most preferably methylthio;
with the proviso that the structure is not that of catalog ID number L995-0405 or L995-0386 of Appendix I;
an inventive molecule selected from the group consisting of a molecule given in Appendix I, wherein said molecule is selected from the group consisting of catalogID numbers: T0502-5560; T0508-5190, T202-1455, T202-0973, K851-0113, T5630309, T5672380, T5967389, T5884038, T5231424, T0517-8250, T0511-9200 and T5627721;
a molecule as shown in Table 1 herein; and
a molecule given in Appendix II, wherein said molecule is selected from the group consisting of catalogID numbers: T6010789, T5993799, T5813085, T6947848, T0517-4117, T5729557, T5705522, Z606-8352, L115-0403, T5712071, T5790476, T5788339, G433-0293, T5719257, T5798761, T5821723, T5787526, T5827594, K405-2595, T5274959, M950-1515, T5450239, G508-0015, T5707230, T5710343, 887-0183, T5453923, T0505-4087, T5673322, T5800607, G869-0071, F2794-0128, T0500-6629, T5832764, M508-0370, T0515-1783, T5393500, T5672380, M381-0730, Z606-8287, G855-0143, Z076-0028, T5311200, E944-0182, L302-0069, T5770640, G869-0064, T5753165, G855-0183, T5329723, T533260, L932-0267, L302-0181, T5444083, T6125251, T5694329, T0517-2783, T5788545, T5586091, T5967389, T5783794, T5494352, T5477696, P621-1364, Y031-0361, T5318833, Z606-8351, T5606387, T0516-6894, T5691896, Z606-8298, F5285-0069, T993-1787, Z606-5341, F3394-1364, Y030-2832, T5400234, T5389517, Z603-8037, T0513-0213, and T636-2387;
or a molecule that is related to a molecular structure in Appendices I or II, and has a suitable metabolic activity in at least one assay as described herein.

The molecule, or pharmaceutical composition comprising same, as described above, optionally wherein for family PQRV, wherein R2 is alkyl, forms a heterocyclic hexyl moiety with the nitrogen to which it is attached, or is absent;
wherein each of R3, R4, R5 and R6 are halogen, H, alkyl, benzyl or alkyl benzyl (unsubstituted or substituted with nitrogen), cyclopentadiene or alky cyclopentadiene (substituted or unsubstituted with S or N) or carbamoyl (optionally alkyated with cyclopropane); R4 and R5 together can be cyclopentadiene, substituted with S and/or N, or unsubstituted, and optionally alkylated;
wherein each of R7-R11 is independently halogen, alkyl, or methoxy, and can be the same or different; or is pyrrolidine, optionally formyl pyrrolidine, in which case preferably R7 is pyrrolidine;

with the proviso that the structure is not that of catalog ID numbers P025-0462, P025-0080, P025-0168, T5581430, F0376-0203, or T5246417 of Appendix I;

with the proviso that if R1 is:

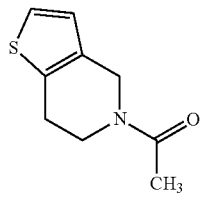

R2 forms a heterocyclic hexyl moiety with the nitrogen to which it is attached;

with the proviso that if R1 is

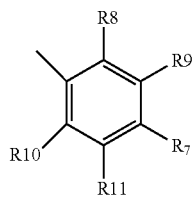

R7 is pyrrolidine, and [C,N] is C, then R4 is not cyclopentadiene or alky cyclopentadiene substituted with both S and N;

with the proviso that if R1 is

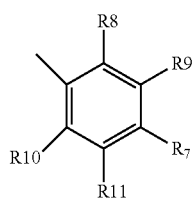

[C,N] is N and R3-R6 are H, then none of R7-R11 is methyl, methoxy or halogen;

with the proviso that if R1 is

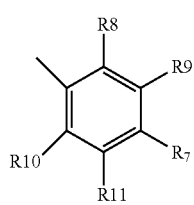

any of R7-R11 is chlorine, and [C,N] is N, then R5 isn't carbamoyl;

with the proviso that if R1 is

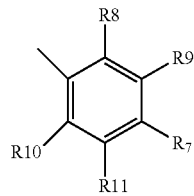

[C,N] is C, any of R7-R11 is halogen or methoxy, and R4 and R5 together form cyclopentadiene, substituted with S and/or N, then the cyclopentadiene moiety is not alkylated nor does it feature a benzyl group;

wherein for Family I, R6 is absent.

The molecule, or pharmaceutical composition comprising same, as described above, optionally, for Family G, R is methyl or ethyl; for RT-R4, if halogen, one or more of R1-R4 is F or Cl; if alkyl, one or more is ethyl or methyl; if alkoxy, one or more ethoxy or methoxy;

wherein for Family A, R1 is nitrogen substituted benzyl or H, and R2 is H;

wherein for Family C, R1 and R2 are each methoxy; each of R3-R5, if alkyl, is ethyl;

wherein for Family E, R is pentyl or R1; if R2 is alkyl, R2 is methyl or ethyl;

wherein for Family F(6) if R is halogen, R is F or Cl; if R is alkyl, R is methyl or ethyl; if R is alkoxy, R is methoxy or ethoxy;

if any of R1-R5 is alkyl, then it is methyl; if any of R1-R5 is alkoxy, then it is methoxy or ethoxy; with the proviso that if R1 is alkoxy, R is not alkyl and is preferably halogen or alkoxy;

wherein for Family F(7), if R is alkyl, R is ethyl or methyl; if R is halogen, R is Cl or F; if R is alkoxy, R is methoxy or ethoxy; if any of R1-R5 is alkyl, then it is methyl; if any of R1-R5 is alkoxy, then it is methoxy or ethoxy;

wherein for Family M, if R is alkyl, R is methyl or ethyl, unsubstituted or substituted with halogen;

wherein for Family Y, if R is alkyl, R is ethyl or methyl; if R is S, R is methylthio or ethylthio; if R is halogen, R is F;

The molecule, or pharmaceutical composition comprising same, as described above, optionally, for Family G, each of R1-R4, if alkyl, is methyl; if alkoxy, is methoxy;

wherein for Family C, only one of R3-R5 is ethyl and the remaining are H;

wherein for Family M, if R is alkyl, R is ethyl;

wherein for Family Y, R is S or halogen;

The molecule, or pharmaceutical composition comprising same, as described above, optionally, for Family G, at least two of R1-R4 are halogen, at least two are alkyl, one is alkoxy and one is alkyl, one is alkyl and one is H, one is halogen and one is H, or one is alkoxy and one is H;

wherein for Family C, R4 is ethyl, and R3 and R5 are H;

wherein for Family M, if R is ethyl, R is substituted with F or Cl, more preferably F; preferably up to three halogens;

wherein for Family Y, if R is S, R is methylthio.

The molecule, or pharmaceutical composition comprising same, as described above, optionally, for Family G, the molecule is selected from the group consisting of GT-G6 of Appendix I (molecules having catalog numbers L924-1031; L924-1088; L924-0830; L924-0760; L924-0884; or L924-0988);

wherein for Family A, the molecule is selected from the group consisting of A1-A3 of Appendix I (molecules having catalog numbers F228-0422, F228-0350 or F228-0534);

wherein for Family C, the molecule is selected from the group consisting of C1-C3 of Appendix I (molecules having catalog numbers T5463586, 4052-4304 or T5463658);

wherein for Family E, the molecule is selected from the group consisting of E1-E4 of Appendix I (molecules having catalog numbers L287-0468, L287-1641, L287-1221 and L287-0220);

wherein for Family F(6), the molecule is selected from the group consisting of F4-F6, F8, F9, F13 of Appendix I (molecules having catalog numbers K404-0800, K404-0673, F0524-0338, K404-0685, K404-0697, and K404-0394);

wherein for Family F(7), the molecule is selected from the group consisting of F1-F3, F7, F10-F12 of Appendix I (molecules having catalog numbers K404-0834, K404-0838, K404-0885, K404-0910, K404-0855, K404-0860, and F0524-0611);

wherein for Family I, the molecule is selected from the group consisting of I1-I5 and 17 of Appendix I (molecules having catalog numbers T636-1937, T636-1114, T636-2387, T636-0134, T636-1210 and T636-2425);

wherein for Family M, the molecule is selected from the group consisting of M1 and M2 of Appendix I (molecules having catalog numbers T5599014 and T5653029);

wherein for Family PQRV, the molecule is selected from the group consisting of P1, Q1-Q3, R1, V1 and V2 of Appendix I (molecules having catalog numbers P025-0159, T5644989, T5599698, T5618591, T5580243, T6937001 and T5511047); and wherein for Family Y, the molecule is selected from the group consisting of Y1 and Y2 of Appendix I (molecules having catalog numbers L995-0125 and L995-0058).

Or Families A, C, E, F(7), F(6), G, I, M, PQRV, Y and Formulas I-VI have any of the structures described herein for the, C, E, F(7), F(6), G, I, M, PQRV, Y and Formulas I-VI for treating of preventing or for use in treatment or prevention a neurological disease, wherein said neurological disease includes ALS or a subtype thereof in a subject in need thereof.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is C 1-C 6 alkyl or C 1-C 4 alkyl. In some embodiments, the "alkenyl" is C 2-C 6 alkenyl or C 2-C 4 alkenyl. In some embodiments, the "alkynyl" is C 2-C 6 alkynyl or C 2-C 4 alkynyl. The term "alkylenyl" as used herein, means a bivalent branched or unbranched saturated hydrocarbon radical. In one aspect, "alkylene" has one to ten carbon atoms, and includes, for example, and without being limited thereto, methylenyl, ethylenyl, n-propylenyl, n-butylenyl and the like. An alkylenyl group can be optionally substituted as described herein. The term "alkenylenyl," as used herein, means a bivalent branched or unbranched hydrocarbon radical having one or more carbon-carbon double bonds (i.e., —CH═CH—). In one aspect, "alkenylenyl" has two to ten carbon atoms, and includes, for example, and without being limited thereto, ethenylenyl, n-propenylenyl, n-butenylenyl and the like. An alkenylenyl group can be optionally substituted as described herein. The term "alkynylenyl," as used herein, means a bivalent branched or unbranched hydrocarbon radical having one or more carbon-carbon triple bonds (i.e., —C≡C—). In one aspect, "alkynylenyl" has two to ten carbon atoms, and includes, for example, and without being limited thereto, ethynylenyl, n-propynylenyl, n-butynylenyl and the like. An alkynylenyl group can be optionally substituted as described herein.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperazinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", or "aryloxyalkyl", refers to carbocyclic aromatic ring systems. The term "aryl" may be used interchangeably with the terms "aryl ring" or "aryl group". "Carbocyclic aromatic ring" groups have only carbon ring atoms (typically six to fourteen) and include monocyclic aromatic rings such as phenyl and fused polycyclic aromatic ring systems in which a carbocyclic aromatic ring is fused to one or more other aromatic ring (carbocyclic aromatic or heteroaromatic), where the radical or point of attachment is on the carbocyclic aromatic ring. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring (carbocyclic aromatic or heteroaromatic), where the radical or point of attachment is on the heteroaromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo", "cyclic", "cyclic group" or "cyclic moiety", include mono-, bi-, and tri-cyclic ring systems including cycloaliphatic, heterocycloaliphatic, carbocyclic aryl, or heteroaryl, each of which has been previously defined.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic carbocyclic aryls, and bicyclic heteroaryls.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

As used herein an optionally substituted aralkyl can be substituted on either or both the alkyl and the aryl portion.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstituted.

According to at least some embodiments there is provided a method for treating a mammal in need of treatment thereof, comprising administering to the mammal an inventive molecule, or a pharmaceutical composition, as described above, for treatment of a neurological disease, wherein said neurological disease includes ALS (Amyotrophic lateral sclerosis), a subtype thereof or a related disease. Optionally, said subtype includes bulbar-onset ALS or limb-onset ALS. Optionally, the related disease includes one of primary lateral sclerosis (PLS), progressive bulbar palsy or progressive muscular atrophy.

The molecule, pharmaceutical composition or method as described above, may be used or performed delaying disease onset in individuals at risk for disease development according to one or more predictive markers.

The molecule, pharmaceutical composition or method as described above, wherein the molecule is in the Family PQRV, with the proviso that the molecule does not include one or more of. Thieno[3,2-c]pyridine-2-sulfonamide, 5-acetyl-4,5,6,7-tetrahydro-N-(phenylmethyl)-; Thieno[3,2-c]pyridine-2-sulfonamide, 5-acetyl-4,5,6,7-tetrahydro-N-[(3-methoxyphenyl)methyl]-; Thieno[3,2-c]pyridine-2-sulfonamide, 5-(cyclopropylcarbonyl)-4,5,6,7-tetrahydro-N-[3-(methylthio)phenyl]-; Thieno[3,2-c]pyridine-2-sulfonamide, 5-acetyl-N-(2,5-dimethylphenyl)-4,5,6,7-tetrahydro-; Thieno[3,2-c]pyridine-2-sulfonamide, 5-acetyl-N-(2,5-dimethylphenyl)-4,5,6,7-tetrahydro-; Thieno[3,2-c]pyridine-2-sulfonamide, 5-(cyclopropylcarbonyl)-N-(3-fluoro-4-methylphenyl)-4,5,6,7-tetrahydro-; Thieno[3,2-c]pyridine-2-sulfonamide, 5-acetyl-N-(2,5-dimethylphenyl)-4,5,6,7-tetrahydro-; Thieno[3,2-c]pyridine-2-sulfonamide, 5-acetyl-N-(2,5-dimethylphenyl)-4,5,6,7-tetrahydro-; Thieno[3,2-c]pyridine-2-sulfonamide, 5-acetyl-N-(2,5-dimethylphenyl)-4,5,6,7-tetrahydro-; Thieno[3,2-c]pyridine-2-sulfonamide, 5-(cyclopropylcarbonyl)-4,5,6,7-tetrahydro-N-[3-(methylthio)phenyl]-; Thieno[3,2-c]pyridine-2-sulfonamide, 5-acetyl-N-(2,5-dimethylphenyl)-4,5,6,7-tetrahydro-; Thieno[3,2-c]pyridine-2-sulfonamide, 5-(cyclopropylcarbonyl)-N-(3-fluoro-4-methylphenyl)-4,5,6,7-tetrahydro-.

Optionally the molecule, pharmaceutical composition or method provides a treatment that comprises an increase of energy metabolism in the nervous system.

It is understood that molecules shown in Appendix I that are toxic or inactive in one or more assays, for example as shown by the test results given herein, are not inventive molecules as described herein. However it is possible that even such molecules could be active if given at lower amounts (for toxic molecules) or at higher amounts or a different form (for molecules that are inactive in one or more assays).

Furthermore, if the readout is presented as a test of cellular toxicity, i.e. MTT, is actually a measurement of the activity of oxidoreductase enzymes, which are mostly present in the mitochondrial Krebs cycle. Hence, MTT can be used to measure mitochondrial activity, which, in some cases, can be used as a proxy for cellular toxicity. However, if compounds that are tested are known to enhance glycolysis, enhancing glycolysis can lead to elevated lactate secretion, which is only possible through the conversion of pyruvate into lactate. If less pyruvate is present in the cell because it is converted into lactate, less acetyl-coA will be generated from pyruvate, and the activity of oxidoreductase enzymes of the Krebs cycle could be transiently reduced, without any link to non-specific cellular toxicity. The use of MTT as a readout of 'toxicity' is therefore inaccurate in the case of compounds whose mode of action is to promote glycolysis and therefore can reduce mitochondrial activity without being toxic to the cell, such as the compounds described herein.

The present invention also provides different forms, including variations and derivatives, of the above compounds, including tautomers, resolved enantiomers, diastereomers, solvates, metabolites, salts and pharmaceutically acceptable prodrugs thereof.

In order that the present invention may be more readily understood, certain terms are first defined. Additional definitions are set forth throughout the detailed description.

As used herein, if a plurality of serial integral values is given, then the series is assumed to include all integral values in between each integral value.

The terms "individual", "host", "subject", and "patient" are used interchangeably herein, and refer any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Various aspects of the invention are described in further detail in the following subsections.

Methods of Treatment

As mentioned hereinabove the inventive molecules described herein can be used to treat a neurological disorder as described herein.

Thus, according to an additional aspect of the present invention there is provided a method of treating a neurological disorder. Specifically the neurological disorder includes ALS (Amyotrophic lateral sclerosis) and its subtypes. ALS subtypes include bulbar-onset ALS and limb-onset ALS. In addition to ALS and its subtypes, optionally the inventive molecules could be used for treatment of primary lateral sclerosis (PLS), progressive bulbar palsy and progressive muscular atrophy.

As used herein the term "treating" refers to preventing, delaying the onset of, curing, reversing, attenuating, alleviating, minimizing, suppressing or halting the deleterious effects of the above-described diseases, disorders or conditions. It also includes managing the disease as described above. By "manage" it is meant reducing the severity of the disease, reducing the frequency of episodes of the disease, reducing the duration of such episodes, reducing the severity of such episodes and the like.

Treating, according to the present invention, can be effected by specifically administering at least one of the inventive molecules of the present invention in the subject.

The inventive molecule may optionally be administered in as part of a pharmaceutical composition, described in more detail below.

Methods of Therapeutic Use

According to at least some embodiments, there is provided new uses and methods of treatment for neurological diseases by administering the inventive molecule to a subject in need of treatment thereof, in a therapeutically effective amount.

The amount to be administered depends upon the therapeutic need and could easily be determined by one of ordinary skill in the art according to the efficacy of the molecule as described herein.

Neurological Diseases and Disorders to be Treated

Neurological diseases and disorders that may be treated using the inventive molecules are described herein. These diseases include ALS (Amyotrophic lateral sclerosis) and its subtypes. ALS subtypes include bulbar-onset ALS and limb-onset ALS. In addition to ALS and its subtypes, optionally the inventive molecules could be used for treatment of primary lateral sclerosis (PLS), progressive bulbar palsy and progressive muscular atrophy.

Amyotrophic Lateral Sclerosis—ALS

ALS is a fatal motor neuron disorder that is characterized by progressive loss of the upper and lower motor neurons at the spinal or bulbar level. ALS is categorized in two forms. The most common form is sporadic (90-95%) which has no obvious genetically inherited component. The remaining 5-10% of the cases are familial-type ALS (FALS) due to their associated genetic dominant inheritance factor. Disease incidence of about 1/100,000. first onset of symptoms is usually between the ages of 50 and 65. The most common symptoms that appear in both types of ALS are muscle weakness, twitching, and cramping, which eventually can lead to the impairment of muscles, progressive muscle atrophy and paralysis, which typically results in patient death within 3 to 5 years of diagnosis (Haverkamp, Appel, &Appel, 1995) due to lack of an effective therapy.

ALS Symptoms and Prognosis

Amyotrophic lateral sclerosis (ALS) is a heterogeneous group of neurodegenerative disorders characterized by progressive loss of motor neurons, consequently resulting in muscle weakness, paralysis and ultimately death. Both upper motor neurons (in the brain) and lower motor neurons (spinal cord) are typically involved.

Patients typically present with either limb onset (80% cases) or bulbar onset (20% cases). In limb onset cases, symptoms appear either distally or proximally in either the upper or lower limb. Bulbar onset cases usually manifest with dysarthria and dysphagia, and limb symptoms can develop along with bulbar symptoms or may occur in the due course of the disease within a year. The typical age onset is about 55 years. It progresses at a fast pace with most of the patients dying within 3-5 years of the onset. However there is also a small subset of ALS cases that present with a relatively slower disease course. The incidence of the disease is approximately similar worldwide ranging from 1 to 2 new cases per 100,000 individuals every year and the prevalence is around 4-6 cases per 100,000 individuals.

Diagnosis of ALS

There is no single, definitive diagnostic test for ALS. While certain diagnostic tests may be ordered to exclude the possibility of ALS, generally only muscle activity and nerve conduction tests will provide evidence of ALS in a patient. Electromyography (EMG) is used to determine electrical activity of muscle fibers. A nerve conduction study (NCS) measures electrical activity of the nerves and muscles by assessing the nerve's ability to send a signal along the nerve or to the muscle.

There are some specific criteria for the diagnosis of ALS known as the E1 Escorial criteria. According to the E1 Escorial criteria, a diagnosis of ALS requires the following:

- signs of degeneration of lower motor neurons, which are in the spinal cord and brainstem, by clinical examination or specialized testing;
- signs of degeneration of upper motor neurons, which are in the brain, by clinical examination;
- progressive spread of signs within a region to other regions; and
- the absence of evidence of other disease processes that might explain the observed clinical and electrophysiological signs.

ALS Biomarkers

There are currently no biomarkers for ALS, although certain genetic abnormalities are seen in some groups of patients. As described in Chen et al ("Genetics of amyotrophic lateral sclerosis: an update", Mol Neurodegener. 2013; 8: 28), there are multiple mutations seen in different ALS cases. While 90% of ALS cases are sporadic, familial cases show different types of inheritance. The article notes that mutations in superoxide dismutase 1 (SOD1), TAR DNA-Binding Protein (TARDBP), fused in sarcoma (FUS), Ubiquilin2 (UBQLN2), C90RF72, alsin, senataxin (SETX), spatacsin, vesicle associated membrane protein associated protein B (VAPB), angiogenin (ANG), factor induced gene 4 (FIG. 4), and optineurin (OPTN) have all been found in ALS patients with the familial form of the disease. Other gene mutations may also be involved.

ALS Mechanism of Action

The mechanism of action of ALS is not known and may in fact involve different etiologies, due to the different genetic mutations and environmental factors which have been associated with the disease. However, researchers have found that dysfunctions of each of oligodendroglia and astrocytes may at least contribute to the pathology of ALS.

Oligodendria support axon survival and function through mechanisms independent of myelination and their dysfunction leads to axon degeneration. Lee et al ("Oligodendroglia metabolically support axons and contribute to neurodegeneration", Nature. 2012 Jul. 26; 487(7408): 443-448) demonstrated that disruption of a lactate transporter in the CNS, monocarboxylate transporter 1 (MCT1), which is expressed on oligodendria, produces axon damage and neuron loss in animal and cell culture models. In addition, this transporter is reduced in patients with, and mouse models of, amyotrophic lateral sclerosis (ALS), suggesting a role for oligodendroglial MCT1 in pathogenesis. Therefore, disruption of lactate metabolism may at least contribute to the pathology of ALS. Treating such a disruption could potentially treat ALS, at least resulting in a reduction of symptoms or a slowing of onset of such symptoms.

Astrocytes have been suggested to be a potential drug target for motor neuron disease, as well as for neurodegenerative diseases generally (Finsterwald et al, "Astrocytes: New Targets for the Treatment of Neurodegenerative Diseases", Current Pharmaceutical Design, 2015, 21, 3570-3581). Astrocytes are particularly important for maintaining normal neuronal metabolism. These cells, among other functions, are responsible to clear glutamate in the synaptic cleft and to initiate the astrocyte neuron lactate shuttle (ANLS). Without the ANLS, transfer of lactate from astrocytes to neurons is not maintained, which results in the impairment of energy metabolism in the nervous system. Again as noted above, disruption of lactate metabolism may at least contribute to the pathology of ALS. Treating such a disruption could potentially treat ALS, at least resulting in a reduction of symptoms or a slowing of onset of such symptoms.

Compounds of the Present Invention

The compounds of the present invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and diastereomers, and mixtures, racemic or otherwise, thereof. Accordingly, this invention also includes all such isomers, including diastereomeric mixtures, pure diastereomers and pure enantiomers of the compounds of this invention. The term "enantiomer" refers to two stereoisomers of a compound which are non-superimposable mirror images of one another. The term "diastereomer" refers to a pair of optical isomers which are not mirror images of one another. Diastereomers have different physical properties, e.g., melting points, boiling points, spectral properties, and reactivities.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention include solvates, pharmaceutically acceptable prodrugs and salts (including pharmaceutically acceptable salts) of such compounds.

The phrase "pharmaceutically acceptable" indicates that the substance or composition is compatible chemically and/or toxicologically with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" can also be used to refer to a complex wherein the solvent molecule is water.

A "prodrug" is a compound that may be converted under physiological conditions or by solvolysis to the specified compound or to a salt of such compound.

Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of an inventive compound can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyl-oxycarbonyl group, as outlined in D. Fleisher, Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., 1996, 39, 10. More specific examples include replacement of the hydrogen atom of the alcohol group with a group such as (C1-C6)alkanoyloxymethyl, 1-((C1-C6) alkanoyloxy)ethyl, 1-methyl-1-((C1-C6)alkanoyloxy)ethyl, (C1-C6)alkoxycarbonyloxymethyl, N—(C1-C6)alkoxycarbonylamino-methyl, succinoyl, (C1-C6)alkanoyl, α-amino (C1-C4)alkanoyl, arylacyl and α-aminoacyl, or (α-aminoacyl-α-aminoacyl, where each α-aminoacyl group is independently selected from the naturally occurring L-amino acids, $P(O)(OH)_2$, —$P(O)(O(C1-C6)alkyl)_2$ or gly-cosyl (the radical resulting from the removal of a hydroxyl group of the hemiacetal form of a carbohydrate).

Free amines of such compounds can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently (C1-C10)alkyl, (C3-C7)cycloalkyl, or benzyl, or R-carbonyl is a natural α-aminoacyl or natural α-aminoacyl-natural α-aminoacyl, —C(OH)C(O)OY wherein Y is H, (C1-C6)alkyl or benzyl, —C(OYO)Y1 wherein Y0 is (C1-C4)alkyl and Y1 is (C1-C6)alkyl, carboxy(C1-C6)alkyl, amino(C1-C4)alkyl or mono-N- or di-N, N—(C1-C6)alkylaminoalkyl, or —C(Y2)Y3 wherein Y2 is H or methyl and Y3 is mono-N- or di-N,N—(C1-C6) alkylamino, morpholino, piperidin-1-yl or pyrrolidin-1-yl.

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Alternatively or additionally, compound of the invention may possess a sufficiently acidic group, a sufficiently basic group, or both functional groups, and accordingly react with any of a number of inorganic or organic bases or acids to form a salt. Examples of salts include those salts prepared by reaction of the compounds of the present invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or ti-salts in a single compound.

If the inventive compound is a base, the desired salt may be prepared by any suitable method available in the art, for example, by treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired salt may be prepared by any suitable method, for example, by treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

In certain embodiments, the salt is a "pharmaceutically acceptable salt" which, unless otherwise indicated, includes salts that retain the biological effectiveness of the corresponding free acid or base of the specified compound and are not biologically or otherwise undesirable.

The compounds of the present invention as described herein also include other salts of such compounds which are not necessarily pharmaceutically acceptable salts, and which may be useful as intermediates for preparing and/or purifying such compounds and/or for separating enantiomers of such compounds.

Pharmaceutical Compositions

The present invention, in some embodiments, features a pharmaceutical composition comprising a therapeutically effective amount of a therapeutic agent according to the present invention. According to the present invention the therapeutic agent is an inventive molecule as described herein. The therapeutic agents of the present invention can be provided to the subject alone, or as part of a pharmaceutical composition where they are mixed with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, mucosal (including intra-nasal) or epidermal administration (e.g., by injection or infusion). Depending on the route of administration, the active compound may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include a pharmaceutically acceptable anti-oxidants. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. A pharmaceutical composition according to at least some embodiments of the present invention also may include additives such as detergents and solubilizing agents (e.g., TWEEN 20 (polysorbate-20), TWEEN 80 (polysorbate-80)) and preservatives (e.g., Thimersol, benzyl alcohol) and bulking substances (e.g., lactose, mannitol).

Examples of suitable aqueous and nonaqueous carriers that may be employed in the pharmaceutical compositions according to at least some embodiments of the present invention include water, buffered saline of various buffer content (e.g., Tris-HCl, acetate, phosphate), pH and ionic strength, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated.

Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Optionally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the present invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intraperitoneal, intravenous (IV) and intradermal), transdermal (either passively or using iontophoresis or electroporation), transmucosal (e.g., sublingual administration, nasal, vaginal, rectal, or sublingual), administration or administration via an implant, or other parenteral routes of administration, for example by injection or infusion, or other delivery routes and/or forms of administration known in the art.

The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion or using bioerodible inserts, and can be formulated in dosage forms appropriate for each route of administration. In a specific embodiment, an inventive molecule or a pharmaceutical composition comprising same according to at least some embodiments of the present invention can be administered intraperitoneally or intravenously.

Compositions of the present invention can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. For the inventive molecules and compositions comprising same as described herein, as further studies are conducted, information will emerge regarding appropriate dosage levels for treatment of various conditions in various patients, and the ordinary skilled worker, considering the therapeutic context, age, and general health of the recipient, will be able to ascertain proper dosing.

The selected dosage depends upon the desired therapeutic effect, on the route of administration, and on the duration of the treatment desired. For example, dosage levels of 0.0001 to 100 mg/kg of body weight daily may be administered to mammals and more specifically 0.001 to 20 mg/kg. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Generally, for intravenous injection or infusion, dosage may be lower. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Optionally the pharmaceutical formulation may be administered in an amount between 0.0001 to 100 mg/kg weight of the patient/day, preferably between 0.001 to 20.0 mg/kg/day, according to any suitable timing regimen. A therapeutic composition according to at least some embodiments according to at least some embodiments of the present invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years).

Alternatively, therapeutic agent can be administered as a sustained release formulation, in which case less frequent administration is required. Dosage and frequency vary depending on the half-life of the therapeutic agent in the patient. The half-life for molecules may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an inventive molecule preferably results in a decrease in severity of disease symptoms, an increase in frequency and duration of disease symptom-free periods, an increase in lifespan, disease remission, or a prevention or reduction of impairment or disability due to the disease affliction.

One of ordinary skill in the art would be able to determine a therapeutically effective amount based on such factors as the subject's size, the severity of the subject's symptoms, and the particular composition or route of administration selected.

In certain embodiments, the pharmaceutical compositions are administered locally, for example by injection directly into a site to be treated. Typically, the injection causes an increased localized concentration of the pharmaceutical compositions which is greater than that which can be achieved by systemic administration. For example, in the case of a neurological disorder, the inventive molecule may be administered locally to a site near the CNS.

Pharmaceutical compositions of the present invention may be administered with medical devices known in the art. For example, in an optional embodiment, a pharmaceutical composition according to at least some embodiments of the present invention can be administered with a needle or other hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in an optional embodiment, a therapeutic composition according to at least some embodiments of the present invention can be administered with a needle or hypodermic injection device, such as the devices disclosed in U.S. Pat. Nos. 5,399,163; 5,383, 851; 5,312,335; 5,064,413; 4,941,880; 4,790,824; or 4,596, 556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447, 233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, therapeutic agents according to at least some embodiments of the present invention can be formulated to ensure proper distribution in vivo. For example, the blood-brain barrier (BBB) excludes many highly hydrophilic compounds. To ensure that the therapeutic compounds according to at least some embodiments of the present invention cross the BBB (if desired), they can be formulated, for example, in liposomes. For methods of manufacturing liposomes, see, e.g., U.S. Pat. Nos. 4,522, 811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Formulations for Parenteral Administration

In a further embodiment, pharmaceutical compositions disclosed herein are administered in an aqueous solution, by parenteral injection. The formulation may also be in the form of a suspension or emulsion. In general, pharmaceutical compositions are provided including effective amounts of an inventive molecule as described herein, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., water soluble antioxidants such as ascorbic acid, sodium metabisulfite, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, alpha-tocopherol; and metal chelating agents, such as citric acid, ethylenediamine tetraacetic acid (EDTA), sorbitol, tartaric acid, phosphoric acid), and preservatives (e.g., Thimersol, benzyl alcohol) and bulking substances (e.g., lactose, mannitol). Examples of non-aqueous solvents or vehicles are ethanol, propylene glycol, polyethylene glycol, vegetable oils, such as olive oil and corn oil, gelatin, and injectable organic esters such as ethyl oleate. The formulations may be freeze dried (lyophilized) or vacuum dried and redissolved/ resuspended immediately before use. The formulation may be sterilized by, for example, filtration through a bacteria retaining filter, by incorporating sterilizing agents into the compositions, by irradiating the compositions, or by heating thecompositions.

Formulations for Topical Administration

Inventive molecules disclosed herein can be applied topically, preferably to one or more of the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers.

Controlled Delivery Polymeric Matrices

Inventive molecules disclosed herein may also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the inventive molecules are dispersed within a solid polymeric matrix or microcapsules, where the core is of a different material than the polymeric shell, and the inventive molecule is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of inventive molecules, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl Polymer ScL, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

Combination Therapy

It will be appreciated that treatment of the above-described diseases according to the present invention may be combined with other treatment methods known in the art (i.e., combination therapy). Thus the therapeutic agents and/or a pharmaceutical composition comprising same, as recited herein, according to at least some embodiments of the present invention can also be used in combination with one or more of the following agents. Riluzole and edaravone may be used with any inventive molecule as described herein.

Other combinations will be readily appreciated and understood by persons skilled in the art. In some embodiments, the therapeutic agents can be used to attenuate or reverse the activity of a drug suitable for treatment of a neurological disease as described herein, and/or limit the adverse effects of such drugs.

As persons skilled in the art will readily understand, the combination can include the therapeutic agents and/or a pharmaceutical composition comprising same, according to at least some embodiments of the invention and one other drug; the therapeutic agents and/or a pharmaceutical composition comprising same, as recited herein, with two other drugs, the therapeutic agents and/or a pharmaceutical composition comprising same, as recited herein, with three other drugs, etc. The determination of the optimal combination and dosages can be determined and optimized using methods well known in the art.

The therapeutic agent according to the present invention and one or more other therapeutic agents can be administered in either order or simultaneously.

Where the therapeutic agents and/or a pharmaceutical composition comprising same, as recited herein, according to at least some embodiments of the invention are administered in conjunction with another therapy, e.g. as herein above specified, dosages of the co-administered drug will of course vary depending on the type of co-drug employed, on the specific drug employed, on the condition being treated and so forth.

Treatment of neurological diseases using the agents of the present invention may be combined with other treatment methods known in the art that are non-drug treatments. Examples of such non-drug treatments include Non-drug therapies include mechanical ventilation, whether invasive or non-invasive.

Example 1—Testing of Inventive Molecules for ALS

Material and Methods

1. Mouse Animal Experimentation

All experiments were carried out in accordance with the Swiss Federal Guidelines for Animal Experimentation and were approved by the Cantonal Veterinary Office for Animal Experimentation in Switzerland.

2. Cell Cultures

Primary cultures of cerebrocortical astrocytes were obtained from 1-2-day-old OF1 mouse pups (Charles River Laboratories). Briefly, cortices were isolated and minced in small pieces under a dissecting microscope. The cells were incubated for 30 min at 37° C. in a solution containing 20 U/ml of papain enzyme (Worthington Biochemical), L-cysteine 1 mM (Sigma), and 10 kU/ml DNase I (Worthington Biochemical) for an enzymatic dissociation. Papain activity was stopped by the addition of fetal calf serum (FCS) to the solution, and a single-cell suspension was then obtained by mechanical dissociation, which consisted in cells trituration in a DMEM (D7777, Sigma-Aldrich) medium (supplemented with 44 mm $NaHCO_3$, and 10 ml/L antibiotic/antimycotic solution) containing 10% FCS. The cells were seeded at an average density of $6 \times 10^4$ cells/$cm^2$ in poly-D-lysine-coated 96, 12 or 6-well culture plates, depending on their use, and incubated at 37° C. in a humidified atmosphere containing 5% $CO_2$/95% air. Culture medium was renewed twice per week. Cells were stimulated and harvested between DIV14 and DIV17, when confluence and cell growth were optimal.

2.1 High Throughput Screening (HTS) for Lactate Secretion

Secretion of lactate in a high-throughput screening (HTS) fashion was measured indirectly through the acidification of extracellular medium. To this end, primary astrocytes grown in 96-well plates for 17 days were stimulated with the compounds as listed herein.

After washing the cells twice with stimulation medium (DMEM (D5030, Sigma), 3 mM $NaHCO_3$ and 5 mM Glucose) at 37° C., cells were stimulated with the compounds at a final concentration of 10 uM (1% DMSO final) in 50 ul per well of stimulation medium supplemented with 10 uM of the extracellular pH sensor SNARF-5F %-(AND-6)-CAR (Life Technologies Corporation). Each compound was tested in two different plates for duplicates.

After 90 min stimulation, fluorescence was read at exc. (excitation) 480 nm/emm. (emission) 580 nm and at exc 480 nm/emm. 630 nm. The ratio of fluorescence between 630 nm and 580 emission values, which represents extracellular pH, was calculated.

In each plate, 8 wells were used for negative controls (DMSO) and 8 wells were used for positive controls (CCCP 2 uM in DMSO). Z prime values were calculated for each of the plates tested and values<0 were discarded.

The average and SD of compounds' values tested in duplicates were calculated, and compound was noted as HIT when the difference between compound's average and negative control's average was greater than three times the sum of compound's SD and negative controls' SD. Only scores greater than 40% were considered as lead Hits for the CDC54K library; for the remaining libraries, all hits were considered. Scores are calculated as the % of activity compared to the positive control in each plate (which is 100%).

Primary screening hits were cherry picked on new plates and confirmed for SNARF5 effect, after having discarded those compounds that are fluorescent (exc. 480 nm/emm. 580 nm or 630 nm) before stimulation. Extracellular medium was next analyzed for extracellular lactate quantification for secondary screening.

2.2 Extracellular Lactate Quantification

Secretion of L-lactate was determined in the extracellular medium of 96-well plated astrocytes after 90 min stimulation (at 37° C., in 5% $CO_2$/95% air conditions) with the drug of interest. The stimulation medium was composed of D5030 medium (completed with D-glucose 5 mM and 44 mM sodium bicarbonate) for 90 min in concentrations ranging from 0 to 100 µM.

Briefly, 200 µl of a Glycine (Sigma)-Semicarbazide (Acros) 0.2M pH 10 buffer containing 3 mM NAD (Roche) and LDH 14 U/ml (Roche) was added to each well of a 96-well plate containing 30 µl aliquots complemented with 20 µl fresh complete D5030 medium. Samples were incubated at 37° C. for 1 h. After samples cooled down at room temperature, the fluorescence intensity (340 nm excitation/450 nm emission) that represents the amount of NADH produced was measured, and lactate concentration values were determined from a standard curve of L-lactate.

2.3 Intracellular Glycogen Quantification

For glycogen dosage, a protein dosage was first performed in order to assess whether harvested astrocytes from primary cell cultures yielded enough and equivalent amounts of proteins comparing each replicate, and to ensure that the obtained differences in glycogen quantities were due to drug action and not to inner protein quantities.

Astrocytes used for these dosages were previously grown in 6-well plates for 17 days and stimulated with Vehicle (DMSO) or drug of interest (1 µM to 100 µM) for 180 min, at 37° C. 5% $CO_2$/95% air in D5030 complete medium. Medium was removed and replaced with 600 µl of 30 mM Tris HCl, and stored at −20° C.

Proteins were dosed using the micro BCA Protein Assay kit (Thermo Scientific), as described in the manufacturer's instructions. Briefly, thawed cells were sonicated and 5 µl aliquots were placed in a transparent 96-well plate, to which we added 25 µl 30 mM Tris HCl, 70 µl H2O and 100 µl of a BCA mix (made as described in manufacturer's guidelines). After a 120 min-incubation at 37° C., absorbance was measured with Safire 2 spectrophotometer at a wavelength of 562 nm, and protein quantities were determined from a standard curve of Bovine Serum Albumin (BSA).

Glycogen was quantified using a 250 µl-aliquot of the same stimulated, thawed, and sonicated cells. After an incubation period of 30 min at 90° C. and 400 rpm, 28 µl of an acetic acid/sodium acetate (both from Sigma) 0.1M pH 4.6 buffer was added to each aliquot, which was then separated in two. Each split aliquot received whether 5 µl of amyloglucosidase (Roche) or 5 µl H2O, and all cell solutions were incubated for 120 min in a shaking 37° C.-waterbath. After a centrifugation at 16'000G for 5 min, 20 µl of supernatant were placed 96-well plate, to which 150 µl of a mix containing 0.67 mM ATP (Roche), 0.67 mM NADP (Roche), 1.8% hexokinase/glucose-6-phosphate dehydrogenase (Roche) and 0.1M Tris Buffer-HCl/3.3 mM magnesium (Fluka)/pH 8.1 buffer was added. Fluorescence was measured with Safire 2 spectrophotometer (340 nm excitation/440 nm emission). Glycogen concentration was obtained by substracting glucose value of samples with amyloglucosidase to samples without amyloglucosidase, and were expressed relative to the amount of proteins previously determined.

2.4 MTT Viability Assay

For cell toxicity determination, astrocytes in 96-well plates were stimulated 24 h (37° C. 5% $CO_2$/95% air) with a gradient ranging from 0.1 to 200 µM of tested compounds. After stimulation, 5 mg/ml thiazol blue tetrazolium bromide (MTT, Sigma-Aldrich) in warm D5030 complete medium was added to each well, and cells were incubated for 4 h at 37° C. (5% $CO_2$). The medium was then removed by aspiration, and the reaction was stopped by the addition of 50 µl DMSO per well.

The amount of reduced MTT (formazan) solubilized in DMSO was then determined spectrophotometrically using absorbance at 570 nm (Safire 2; Tecan).

2.5 Production of Reactive Oxygen Species (ROS).

Hydrogene peroxide ($H_2O_2$) released in the supernatant is detected enzymatically with Amplex red (Zhou, Diwu et al. 1997). Oxidation of Amplex red is catalysed by the horseradish peroxidase in presence of H2O2 into highly fluorescent resorufin. Fluorescence measure is read at 545 nm extinction, 590 nm emission. The amount of H2O2 was expressed relatively to the proteins content extracted from the cells in culture.

3. In Vivo Testing 3.1 Mice

For in vivo acute toxicity, in vivo chronic toxicity, pharmacodynamics experiments, and pharmacokinetics experiments, adult male or female C57Bl/6J mice weighting 18-28 g (8 weeks of age) were used (Charles River or Harlan).

For ALS mouse models, G93A SOD1 transgenic male or female mice on B6.SJL1-Gur/J genetic background were used (Jackson Laboratory).

All experiments were conducted in strict accordance with the Guide for the Care and Use of Laboratory Animals (National Research Council 2011) and were approved by relevant animal care authorities.

Animals were housed in groups of 3-5 in polypropylene cages (30×40×15 cm) with wire mesh top in a temperature (22±2° C.) and humidity (55±15%) controlled environment on a 12 hour light cycle (07.00-19.00 h lights on), except after surgeries when animal were housed individually.

3.2 In Vivo Drug Administration

Drugs were administered per os (gavage) in a solution made of water supplemented with 0.4% hydroxypropyl methylcellulose (HPMC) Methocel 4KM (w/v) and 0.25% Tween-20 (v/v), as previously described. The compound was administered at 10 mg/kg. Concentrations of drugs tested ranged from 10 to 100 mg/kg.

3.3 In Vivo Acute Toxicity

In vivo acute toxicity was assessed with a starting maximal concentration of 100 mg/kg. If at any point toxic effects were observed, a second 10-times lower concentration was tested, and so forth until non-toxic concentration was reached, hence providing optimal dose of our compound for in vivo testing. Groups of 6-8 female mice were monitored for 14 days after single oral administration of the drug, weighted every day, and a macroscopic histological examination was performed at the end of the experiment. Clinical evaluation included the observation of mice' ability to feed, hydrate, notification of any visible pain, unusual grooming or respiration, blood loss, evidence of microbial infection, and/or significant loss of weight.

3.4 In Vivo Chronic Toxicity

Chronic toxicity was assessed in groups of 10 male and 10 female C57BL/6J mice over a period of 28 days. Drugs or Vehicle were administered per os, once a day, as previously described. During this period, clinical symptoms and weight were recorded. At the end of the 28-day period, 3 mice per group were sacrificed for histopathological analyses. The other mice were kept for another 14 days without treatment to assess for late-coming toxic effects, followed by the same analyses. Histopathology was performed by specialized platform of mouse pathology facility at the CHUV hospital (Lausanne, Switzerland).

3.5 In Vivo Pharmacodynamics—Lactate Biosensors

Extracellular levels of lactate were monitored in vivo using lactate biosensors (Pinnacle Technology), according to the manufacturer's instructions. Cannulae were surgically implanted in mice cerebral cerebral motor cortex areas M1/M2 (coordinates: +1.94 mm (to bregma), lateral −1.4 mm (to mideline), ventral −1.0 mm (to dura)) 5-7 days before administration of the compounds. Drugs were administered per os as previously described, and cerebral levels of extracellular lactate were dynamically recorded for 6 hours. Mice were administered vehicle alone first, followed 3 hours later by vehicle or drug (10 or 100 mg/kg). Area Under the Curve (AUC) quantifying the fluctuations of extracellular lactate concentrations for each of the compound tested was calculated using Graphad Prism and the ratio of AUC after drug over Vehicle administration was calculated. Groups of 8 male mice were used for each condition.

3.6 In Vivo Pharmacodynamics—Glycogen Quantification

To measure intracerebral levels of glycogen, mice were euthanized at different time points after drug administration, using a microwave beam (1 sec, 6 kW) focused directly on mice brains. This method of fixation results in the rapid inhibition of enzymatic reactions, thereby preserving intact metabolic state in the brain of euthanized animals. Glycogen concentration was quantified using standard biochemical procedure. Groups of 8 male mice were used for each condition.

3.7 In Vivo Pharmacokinetics 3.7.1 Surgery

Mice were anesthetized using isoflurane (2% and 800 mL/min O2). Before surgery, Finadyne (1 mg/kg, s.c.) was administered for analgesia during surgery and the post-surgical recovery period. A mixture of bupivacaine and epinephrine was used for local anesthesia of the incision site of the periost of the skull.

3.7.2 Microdialysis Probe Implantation into the Prefrontal Cortex (PFC)

The animals were placed in a stereotaxic frame (Kopf instruments, USA). MetaQuant microdialysis probes with a 3 mm exposed polyacrylonitrile membrane (MQ-PAN 3/3, Brainlink, the Netherlands) were implanted into the prefrontal cortex (coordinates for the tip of the probe: AP=+2.0 mm (to bregma), lateral=−0.7 mm (to mideline), ventral=−3.3 mm (to dura), with the incisor bar set at 0.0 mm and an angle of 8°). All coordinates were based on "The mouse brain in stereotaxic coordinates" by Paxinos and Franklin (2004). The probes were attached to the skull with a stainless steel screw and dental cement (Fuji Plus Capsules, Henry Schein, the Netherlands).

3.7.3 Jugular Vein Cannulation

In the same surgical procedure, a catheter was placed into the jugular vein to accommodate blood sampling. An indwelling cannula was inserted into the right jugular vein, and exteriorized through an incision on top of the skull. The end of the jugular vein catheter was fixed in position with dental acrylic cement and attached to the skull with two stainless steel screws.

3.7.4 Experimental Design

Experiments were initiated one day after surgery. The MetaQuant microdialysis probes were connected with flexible PEEK tubing (Western Analytical Products Inc. USA; PK005-020) to a microperfusion pump (CMA Microdialysis) and perfused with aCSF+0.2% BSA at a flow rate of 0.12 µL/min. Ultrapurified water+0.2% BSA was used as the carrier flow at a flow rate of 0.80 µL/min. After a minimum of 1.5 hours of prestabilization, microdialysis samples were collected in 30 minute intervals. Samples were collected into polystyrene microvials (Microbiotech/se AB, Sweden; 4001029) using an automated fraction collector (UV 8301501, TSE, Univentor, Malta). After collection of three basal samples, at t=0 minutes, drug of interest was administered per os. Eight additional samples were collected after compound administration. All samples were stored at −80° C. until off-line analysis.

In parallel, blood samples (50 µL) were taken from the jugular vein through the cannula. These samples were collected at specified intervals into vials containing 5 µL heparin (500 IE/mL in saline). The samples were mixed by inverting the tubes and, subsequently, centrifuged at 4000 rpm (1500×g) for 10 min at 4° C. The supernatant was stored as plasma in 1.5 mL Eppendorf vials (Sarstedt, Germany) at −80° C. until off-line analysis.

At the end of the experiment, the animals were euthanized and terminal brain tissue was collected for visual histological verification of the probe positions.

3.8 Therapeutic Effect—SOD1 G93A Mouse Model

The ALS mouse model features transgenic mice having a B6.SJL1-Gur/J genetic background that overexpress the human mutated gene G93A SOD1. Mating colonies were composed of wild-type female mice and SOD1 G93A male mice, both on B6.SJL1-Gur/J background. F1 pups were genotyped after ear punching at weaning, using quantitative PCR (qPCR), which allows determining the number of SOD1 copies in transgenic mice.

To test for therapeutic effect, SOD1 mice were administered orally the molecule of interest (10 to 100 mg/kg) or vehicle every day from post-natal day 30 throughout their entire life. 3 groups were compared: wild-type mice treated with Vehicle, G93A SOD1 mice treated with Vehicle, and G93A SOD1 mice treated with the drug of interest. Groups of at least 12 male and female mice were used. Weight was recorded every day for each mouse throughout the entire treatment, while neuromuscular function was measured once a week. Evaluation of neuromuscular function consisted in testing muscle strength using the grip test, and in assessing motor deficit evolution in a score sheet according to specific visual observation: normal walking (0), one paw curls up when tail-suspended (1), both paws curl up when tail-suspended (2), paralyzed paw when walking (3), inability to move back when mouse is placed on its back (4).

3.8.1 Grip Test

The experiment was conducted in a room with a low light intensity of ~30 lux, to avoid any additional stressful conditions. Mice were individually placed in the center of an elevated (35 cm height) upside-down 42×42 cm grid, which was placed on a bubble pack-lined table, for a maximal period of 5 min. Their ability to grip the grid (time[s]) was measured in order to assess for muscle strength.

3.8.2 Survival

Mice were sacrificed when they reached at least one of the predefined criteria: i) losing ≥15% of their maximal weight, ii) taking ≥20 s to move back when placed on their back (criteria of 4 on the paralysis evaluation scale). The obtained Kaplan-Meier survival curves were then compared using Graphpad prism v.6.

4. Statistical Analyses

Statistical analyses were done using Graphpad prism v.6 using unpaired or paired 2-way Student's t-test for pairwise comparisons, or one-way or two-ways ANOVA followed by Dunnett, Bonferroni or Tukey HSD post-hoc tests when appropriate for multiple pair-wise comparisons.

Results Summary

1. High Throughput Cellular Screening

Identification of lactate-enhancing drugs with high throughput screening (HTS) experiments on astrocytes primary cultures using extracellular pH dye (SNARF5F 5-(and-6)-carboxylic acid) for 90 min. The procedure is described in Material and Methods (2. Cell culture, 2.1. HTS for lactate secretion and 2.2. Extracellular lactate quantification).

The procedure was performed as follows:
- Primary screening: acidification of the extracellular medium
- Primary screening confirmation: acidification of the extracellular medium, removal of compounds with fluorescent activity at exc. 480 nm/emm. 580 nm or 630 n.
- Secondary screening: dosage of extracellular lactate The first library screened was the Prestwick library, composed of 1240 FDA-approved drugs (available from Prestwick Holding and Chemical Inc., USA). The best stimulators of release of lactate were found to be the following 19 hits in Table 1.

TABLE 1

Prestwick hits

| Prestwick number | Name | Internal code | Score |
|---|---|---|---|
| Prestw-1040 | Pyrvinium pamoate | | 0.990552111 |
| Prestw-999 | Proguanil hydrochloride | GP3 | 0.554660869 |
| Prestw-827 | Propantheline bromide | | 0.490672894 |
| Prestw-79 | Diphemanil methylsulfate | GP4 | 0.484445876 |
| Prestw-777 | Alexidine dihydrochloride | | 0.388893362 |
| Prestw-583 | Papaverine hydrochloride | GP7 | 0.355181577 |
| Prestw-1467 | Troglitazone | | 0.269935851 |
| Prestw-1288 | Idebenone | | 0.258984889 |
| Prestw-372 | Debrisoquin sulfate | GP5 | 0.237512414 |
| Prestw-1181 | Tibolone | GP6 | 0.226776176 |
| Prestw-298 | Fipexide hydrochloride | | 0.165794347 |
| Prestw-961 | Denatonium benzoate | | 0.109751188 |
| Prestw-292 | Trazodone hydrochloride | | 0.083769493 |
| Prestw-1393 | Dibenzepine hydrochloride | | 0.080119172 |
| Prestw-67 | Miconazole | | 0.073462705 |
| Prestw-76 | Dibucaine | | 0.061223394 |
| Prestw-1390 | Desloratadine | | 0.060793945 |
| Prestw-1423 | Fosinopril | | 0.057143624 |
| Prestw-68 | Isoxsuprine hydrochloride | | 0.054996377 |

The next library tested was the CDC54K library composed of 54,000 compounds (from the Bioscreening facility at EPFL, Lausanne, Switzerland), grouped into chemical families. Appendix I features a list of chemical motifs, based upon structural analysis of the full list of hits. Appendix II features a list of molecules that were shown to be active but that may be additional to the molecules of Appendix I. The molecules listed in Table 1 above, as well as in Appendix II, are termed herein "inventive molecules".

Any molecule featuring a motif or that is related to a molecular structure given in Appendix I, and has suitable metabolic activity in at least one assay as described herein, may also be termed herein an "inventive molecule".

2. In Vitro Characterization

Hits were characterized in vitro on primary astrocytes cultures for their effect on lactate secretion (EC50), glycogen degradation, $H_2O_2$ production (to avoid molecules that stimulate glycolysis through blocking of mitochondrial respiration) and cellular toxicity (LD50). The molecules were also characterized for their 'druggability' through Pfizer rule of 5 and theoretical crossing of the blood brain barrier (polar surface area <90 Å).

Technical procedures are described in Material and Methods (2. Cell culture).

a. Hits from Prestwick Library i. Secretion of Lactate

Levels of lactate secreted by astrocytes were measured in the extracellular medium at 90 min after stimulation with 20 hits (molecules) from the Prestwick library (10 μM each), as shown in FIG. 1. n=6-10; Ctrl pos. is CCCP (2 uM). Statistical analysis consisted in ANOVA followed by Fisher LSD post-hoc test for pair-wise comparisons. In addition, a range of concentrations of the Prestwick compounds (0-100 μM) was used to calculate EC50, as shown in Table 1 below.

ii. Degradation of Glycogen

Figure 2:
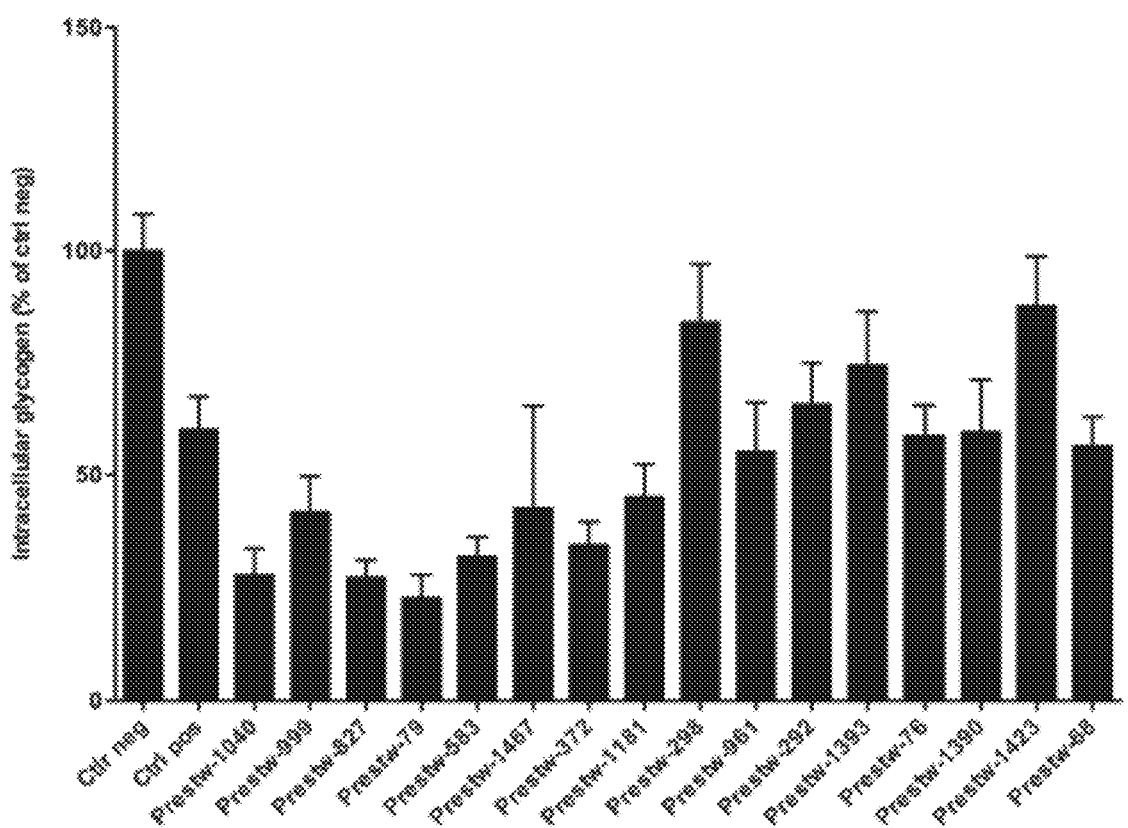
FIG. 2 shows the intracellular levels of glycogen in astrocytes after treatment with lead hits (molecules) from the Prestwick library.

Levels of intracellular glycogen in astrocytes were measured at 3 h after stimulation with 20 Hits from the Prestwick library (10 μM each), as shown in FIG. 2. n=6-10; Ctrl pos. is glutamate (0.5 mM). Statistical analysis consisted in ANOVA followed by Fisher LSD post-hoc test for pair-wise comparisons.

iii. Cellular Toxicity by MTT

Figure 3:
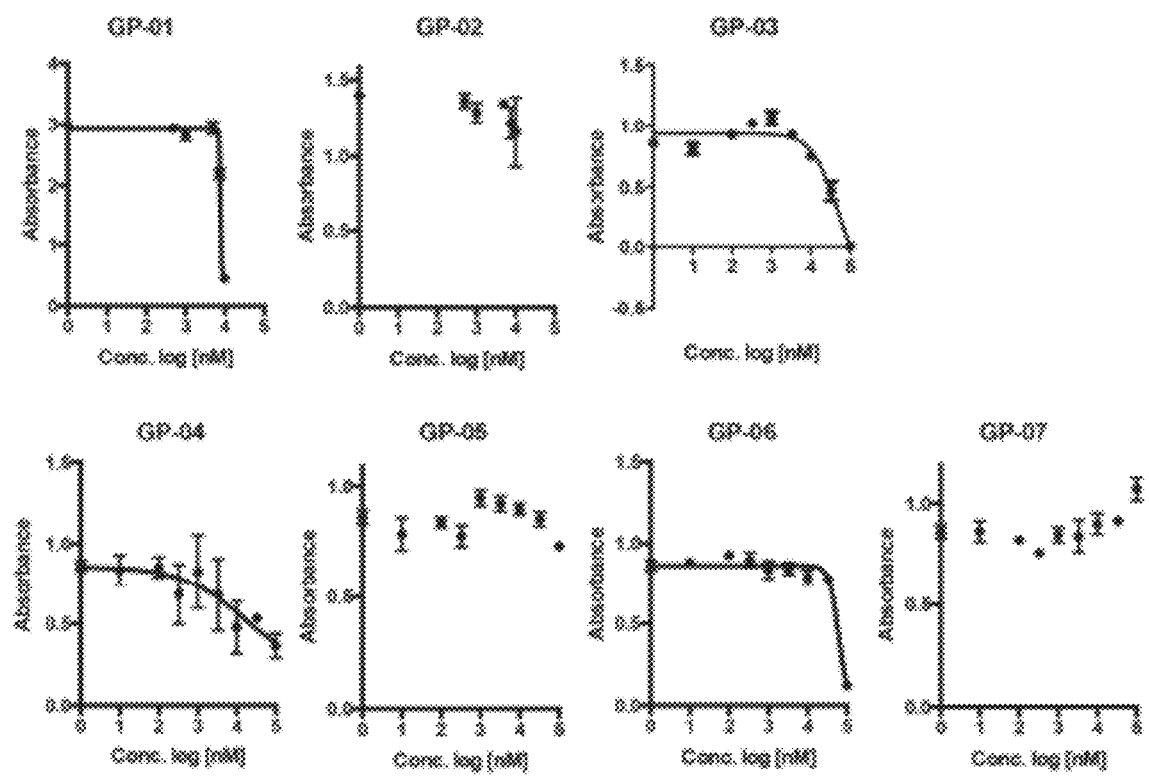
FIG. 3 shows the results for the MTT Assay in astrocytes after treatment with lead hits (molecules) from the Prestwick library.

MTT cellular viability assay was performed on astrocytes exposed to Preswtick Hits (concentrations ranging from 0 uM to 200 uM). Examples for lead molecules are shown in FIG. 3. The cellular toxicity results are summarized in Table 2 below.

iv. Mitochondrial Activity

Figure 4:
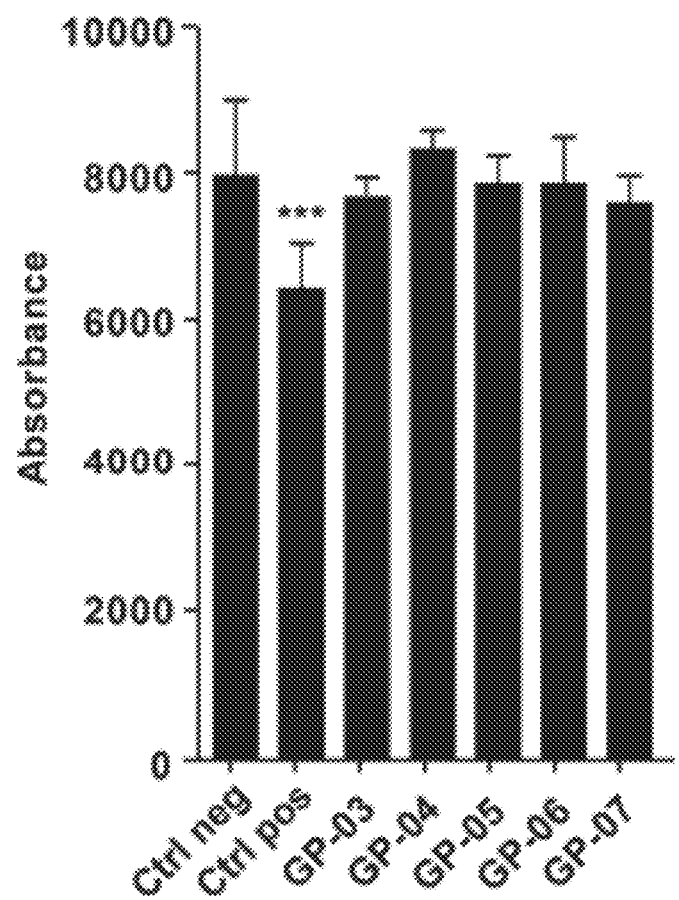
FIG. 4 shows mitochondrial activity in astrocytes after treatment with lead hits (molecules) from the Prestwick library.

Mitochondrial respiration in astrocytes was measured through production of $H_2O_2$ at 90 min after stimulation with Prestwick Hits (10 uM each). FIG. 4 shows mean absorbance+SEM; n=4. CCCP (2 uM) was used as positive control.

v. List Summary

Table 2 shows a summary of Prestwick hits activity, including HTS score, lactate effect (EC50), statistical significance of glycogen degradation (* $p<0.05$,  $p<0.01$, * $p<0.001$, **** $p<0.0001$), cellular toxicity measured by MTT (IC50), Pfizer Rule of 5 and total polar surface area (PSA).

TABLE 2

| Prestwick Library number | Name | Internal code | HTS Score (lactate) | Lactate EC50 (uM) | Glycogen | MTT IC50 (uM) | Pfizer Rule of 5 | PSA |
|---|---|---|---|---|---|---|---|---|
| Prestw-1040 | Pyrvinium pamoate | | 0.991 | | **** | | ok | 12.06 |
| Prestw-999 | Proguanil hydrochloride | GP3 | 0.555 | 0.8536 | *** | 48.1 | ok | 83.78 |
| Prestw-827 | Propantheline bromide | | 0.491 | 11.714 | **** | 12.8 | ok | 35.54 |
| Prestw-79 | Diphemanil methylsulfate | GP4 | 0.484 | 1.174 | **** | 13.9 | ok | 0 |
| Prestw-777 | Alexidine dihydrochloride | | 0.389 | — | — | — | no | 167.6 |
| Prestw-583 | Papaverine hydrochloride | GP7 | 0.355 | 0.6293 | **** | >200 | ok | 49.83 |
| Prestw-1467 | Troglitazone | | 0.270 | 2.574 | *** | 105.5 | milogp | 84.86 |

TABLE 2-continued

| Prestwick Library number | Name | Internal code | HTS Score (lactate) | Lactate EC50 (uM) | Glycogen | MTT IC50 (uM) | Pfizer Rule of 5 | PSA |
|---|---|---|---|---|---|---|---|---|
| Prestw-1288 | Idebenone | | 0.259 | 0.6018 | — | 112.3 | ok | 72.84 |
| Prestw-372 | Debrisoquin sulfate | GP5 | 0.238 | 2.728 | **** | >200 | ok | 53.11 |
| Prestw-1181 | Tibolone | GP6 | 0.227 | 2.235 | *** | 60.7 | ok | 37.3 |
| Prestw-298 | Fipexide hydrochloride | | 0.166 | 5.16 | ns | 44.0 | ok | 51.25 |
| Prestw-961 | Denatonium benzoate | | 0.110 | 12.219 | ** | 178.0 | ok | 29.1 |
| Prestw-292 | Trazodone hydrochloride | | 0.084 | 10.954 | ns | >200 | milogp | 39.31 |
| Prestw-1393 | Dibenzepine hydrochloride | | 0.080 | | ns | | ok | 30.18 |
| Prestw-67 | Miconazole | | 0.073 | | — | | milogp | 27.06 |
| Prestw-76 | Dibucaine | | 0.061 | | * | | ok | 3.3 |
| Prestw-1390 | Desloratadine | | 0.061 | 2.095 | * | 11.0 | ok | 24.92 |
| Prestw-1423 | Fosinopril | | 0.057 | | ns | | no | 110.2 |
| Prestw-68 | Isoxsuprine hydrochloride | | 0.055 | | ** | | ok | 61.7 | b. Hits from the CDC54K Library
i. Lactate Secretion

Figure 5A:
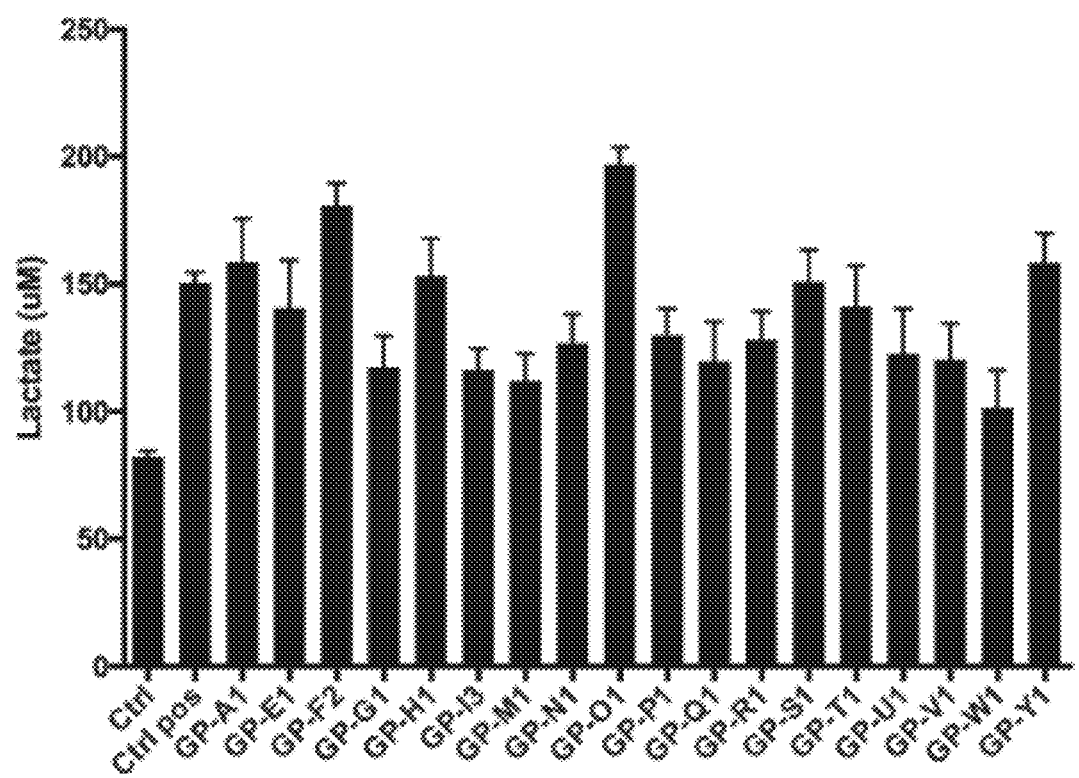
FIG. 5A shows the extracellular levels of lactate in astrocytes after treatment with 18 hits (molecules) from the CDC54K library.

Levels of lactate secreted by astrocytes were measured in the extracellular medium at 90 min after stimulation with hits (molecules) from the CDC54K library. Concentrations ranging from 0 to 100 uM were used to calculate EC50, as shown in Table 3 below. Lead hits from the CDC54K library that have been tested consisted in one member of each of the 18 CDC54K families. The results are shown in FIG. 5A.

ii. Glycogen Degradation

Figure 5B:
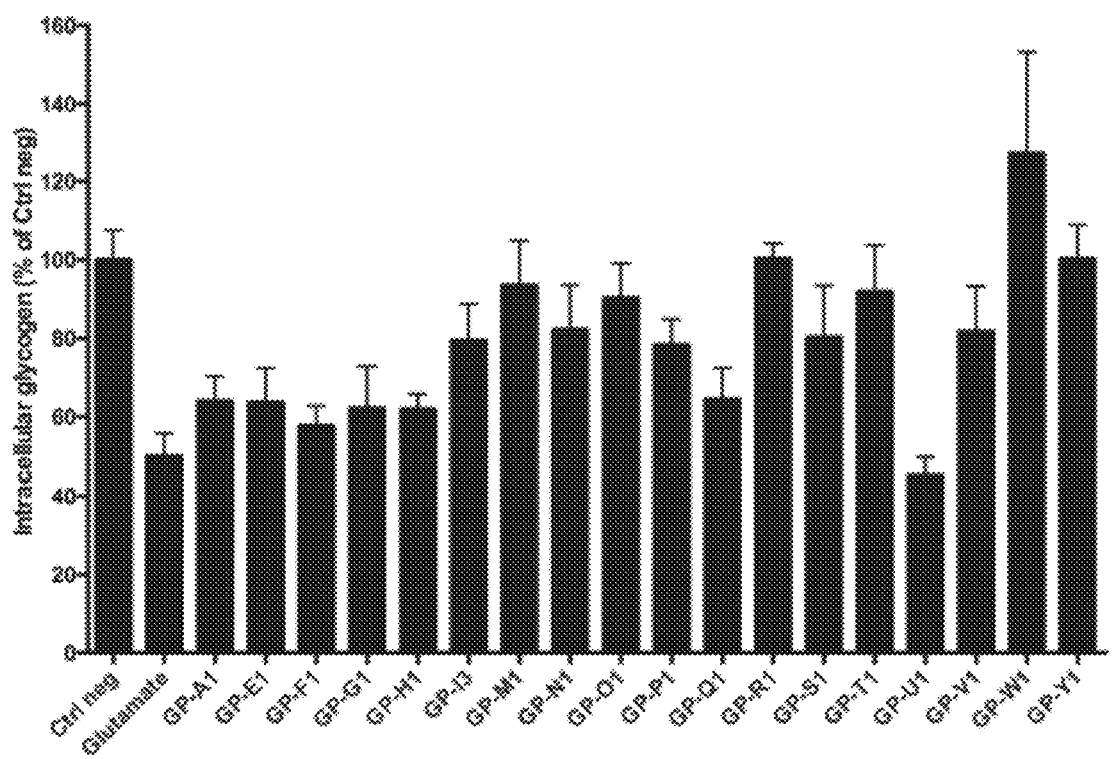
FIG. 5B shows levels of intracellular glycogen in astrocytes measured at 3 h after stimulation with 18 hits (molecules) from the CDC54K library.

FIG. 5B shows levels of intracellular glycogen in astrocytes that were measured at 3 h after stimulation with 18 hits from the CDC54K library (10 μM each). n=6-10; Ctrl pos. is Glutamate or Nor-epinephrine. Statistical analysis consisted in ANOVA followed by Fisher LSD post-hoc test for pair-wise comparisons.

iii. Cellular Toxicity by MTT

MTT cellular viability assay was performed on astrocytes exposed to CDC54K Hits (concentrations ranging from 0 uM to 200 uM). IC50 data are summarized in Table 3.

iv. Mitochondrial Activity

Mitochondrial respiration in astrocytes was measured through production of $H_2O_2$ at 90 min after stimulation with CDC54K Hits (ranging from 0 to 200 uM). IC50 data are summarized in Table 3.

v. List Summary

Table 3 shows a summary of CDC54K hits activity, including HTS score, lactate effect (EC50), statistical significance of glycogen degradation, cellular toxicity measured by MTT (IC50), effect on H2O2, Pfizer Rule of 5 and total polar surface area (PSA).

TABLE 3

| CDC54K Library number | Family | Internal code | HTS Score (SNARF5) | Lactate EC50 (uM) | Glycogen | MTT IC50 (uM) | H2O2 IC50 (uM) | Pfizer Rule of 5 | PSA |
|---|---|---|---|---|---|---|---|---|---|
| F228-0422 | A | GP-A1 | 1.058 | 0.5 | ** | >200 | >200 | ok | 71.26 |
| T5463586 | C | GP-C1 | 0.77 | 10.0 | *** | >200 | >200 | ok | 55.85 |
| L287-0468 | E | GP-E1 | 0.597 | 7.9 | ** | >200 | >200 | ok | 85.09 |
| K404-0834 | F(7) | GP-F1 | 1.123 | 1.8 | ** | 150 | >200 | ok | 35.7 |
| L924-1031 | G | GP-G1 | 0.929 | 25.3 | ** | >200 | 48.6 | ok | 25.89 |
| T0508-5190 | H | GP-H1 | 0.459 | 3.1 | ** | 75 | 185.4 | ok | 59.52 |
| T636-2387 | I | GP-I3 | 0.445 | 11.5 | ns | >200 | >200 | ok | 69.02 |
| T5599014 | M | GP-M1 | 0.542 | 8.8 | ns | >200 | 157.9 | ok | 74.85 |
| T0517-8250 | N | GP-N1 | 0.957 | 3.0 | ns | 139.6 | >200 | ok | 29.02 |
| T202-1455 | O | GP-O1 | 0.971 | 15.0 | ns | >200 | >200 | ok | 43.19 |
| P025-0159 | P | GP-P1 | 0.953 | 8.7 | ns | >200 | >200 | ok | 60.93 |
| T5644989 | Q | GP-Q1 | 0.68 | 7.9 | ** | >200 | >200 | ok | 79.37 |
| T5580243 | R | GP-R1 | 0.853 | 11.0 | ns | >200 | >200 | ok | 68.3 |
| T0511-9200 | S | GP-S1 | 0.844 | 10.2 | ns | >200 | >200 | ok | 71.95 |
| K851-0113 | T | GP-T1 | 0.722 | 2.0 | ns | >200 | >200 | ok | 61.2 |
| T5884038 | U | GP-U1 | 0.721 | 12.2 | **** | 70.5 | >200 | ok | 46.17 |
| T6937001 | V | GP-V1 | 0.809 | 11.5 | ns | >200 | >200 | ok | 59.06 |
| T5967389 | W | GP-W1 | 0.79 | 23.5 | * | >200 | >200 | ok | 75.71 |
| L995-0125 | Y | GP-Y1 | 0.854 | 2.0 | ns | >200 | 173.4 | ok | 92.51 |

3. In Vivo Characterization
a. Acute Toxicity

Figure 6:
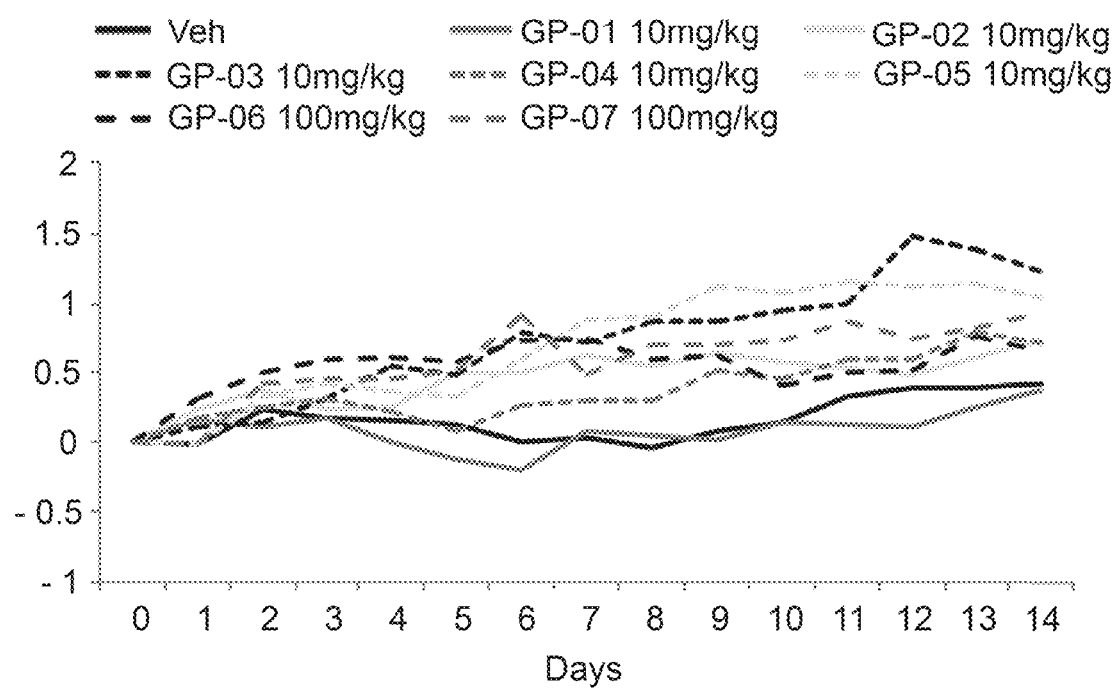
FIG. 6 shows the results of weight monitored during a 14-day period after acute administration of the drug (100 mg/kg when not indicated otherwise) in C57Bl/6 female mice; n=6.

Lead molecules from in vitro were tested in vivo, starting with acute toxicity/dose optimization on wild-type C57Bl/6 female mice for a period of 14 days following administration. For this period, mice were weighted and clinically monitored (feeding, hydration, pain, grooming, respiration, blood loss, microbial infection). At the end of the 14-day evaluation, mice were sacrificed and high level organ analysis was performed. Drugs were always administered per os (gavage) in solution composed of Methocel 4KM 0.4%, Tween 0.25%. The results are shown in FIG. 6.

Summary

GP-03 was toxic at 100 mg/kg but not at 10 mg/kg (dose optimization)

None of the other tested molecules (GP-01-GP-07; GP-A, I, P, Q, R, V) were toxic at 100 mg/kg b. Chronic Toxicity Chronic toxicity was assessed before chronic administration in SOD1 mice. C57Bl/6 male and female mice were used with GP-01, 02, 04, 05, 06 and 07 at 10 mg/kg. GP-03 was not tested as was already toxic after acute administration at 100 mg/kg, and did not show good PD effect at 10 mg/kg (see below for more information).

Figure 7:
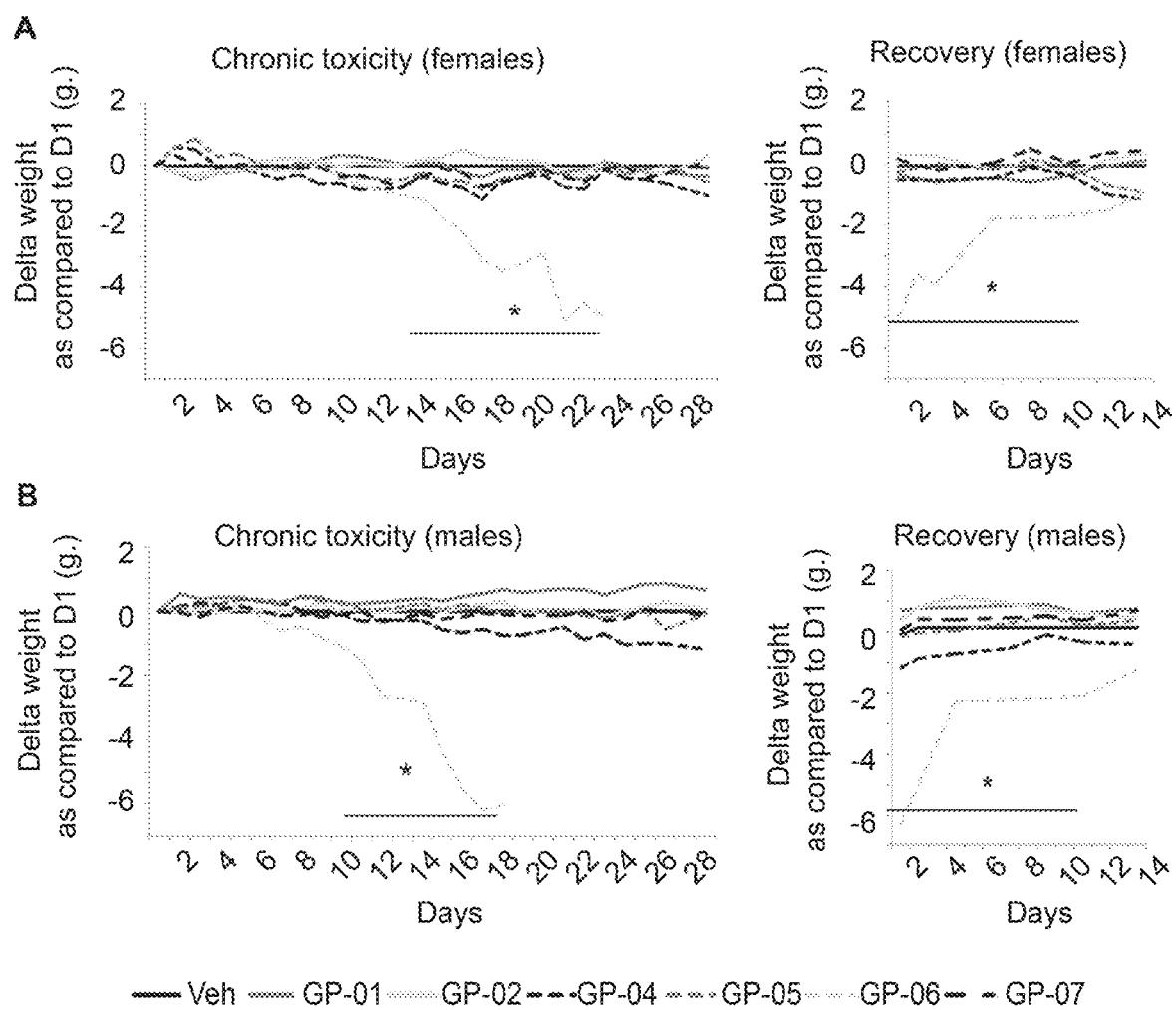
FIG. 7 shows the weight of male and female mice during a 28-day period chronic treatment with GP-01, GP-02, GP-04, GP-05, GP-07 and GP-07 at 10 mg/kg, followed by a 14-day recovery period; n>10.
Figure 8:
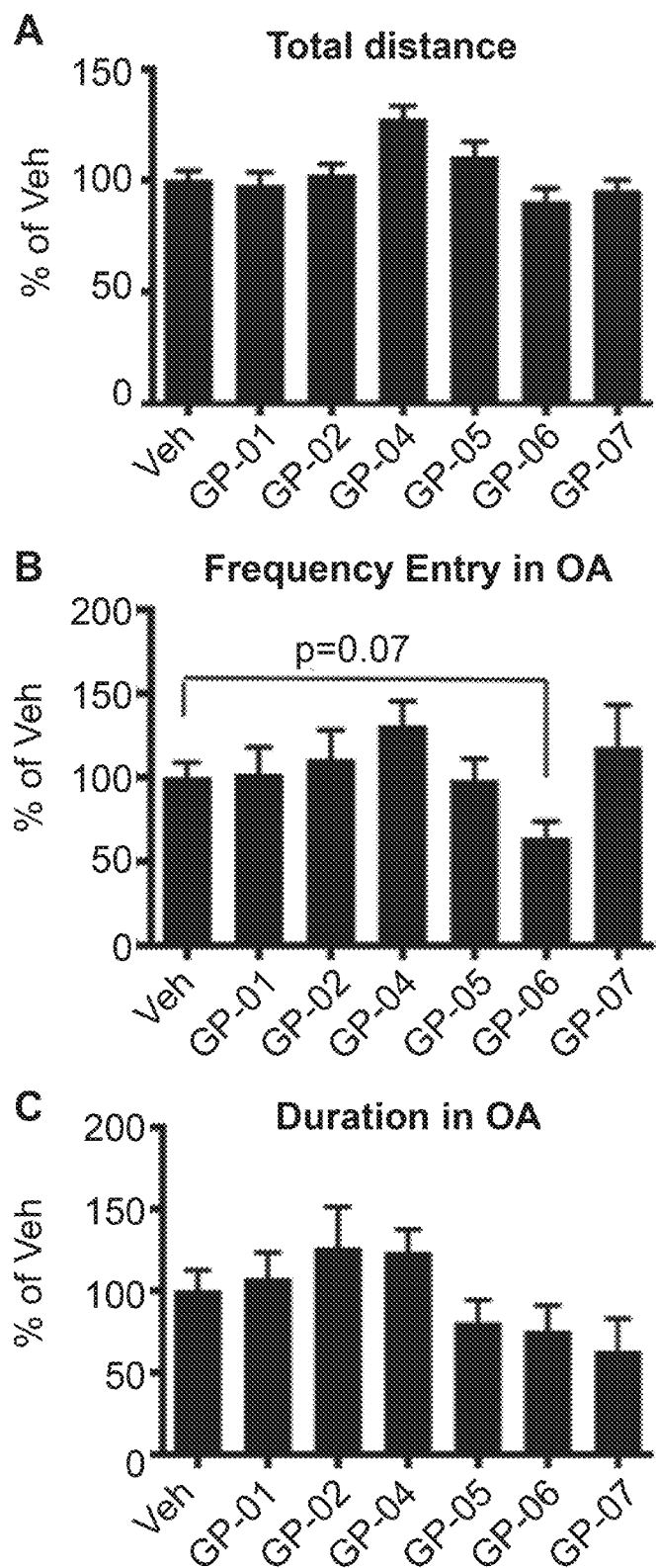
FIG. 8 shows the results of anxiety testing: at the end of the chronic treatment, mice were tested for anxiety in an EPM (elevated plus maze). Total distance, frequency of entry and duration in the open arms were measured using Ethovision automatic scoring; n>10.

Mice were treated for 28-day and monitored for their weight and clinical symptoms, and were next tested for anxiety in an elevated plus maze (EPM). Half of mice were then sacrificed and pathological analysis was performed on a number of organs (brain, tongue, esophagus, diaphragm, stomach, small intestine, pancreas, large intestine, kidneys, adrenal, liver, spleen, pancreas, mesentheric lymph nodes, spinal cord, bone marrow, muscle), while half of mice were sacrificed 14-day later to assess for recovery effects and/or remote toxicity and same pathological analysis ways performed. Results are shown in FIGS. 7 and 8.

Summary

GP-06 chronic administration at 10 mg/kg was toxic and interrupted when weight loss was >20%. Therefore chronic administration of GP-06 at 10 mg/kg will not be used in chronic treatment on SOD1 mice.

GP-01, GP-02, GP-04, GP-05 and GP-07 are safe when administered chronically at 10 mg/kg.

EPM analysis revealed increased anxiety of GP-06 treated mice at the end of the treatment, which correlates with toxicity of the chronic treatment. None of the other chronic treatments resulted in significantly elevated anxiety.

Pathological analysis performed by mouse pathology facility at the CHUV revealed minor treatment-related effects in GP-07-treated mice, including leukocyte cell infiltrates, single cell necrosis in the liver and bulbe duct proliferation. The same was true for a focal amorphous, intratubular vacuole in the kidney of one male mouse treated with GP-07.

c. Pharmacodynamics—Lactate Biosensors

Figure 9:
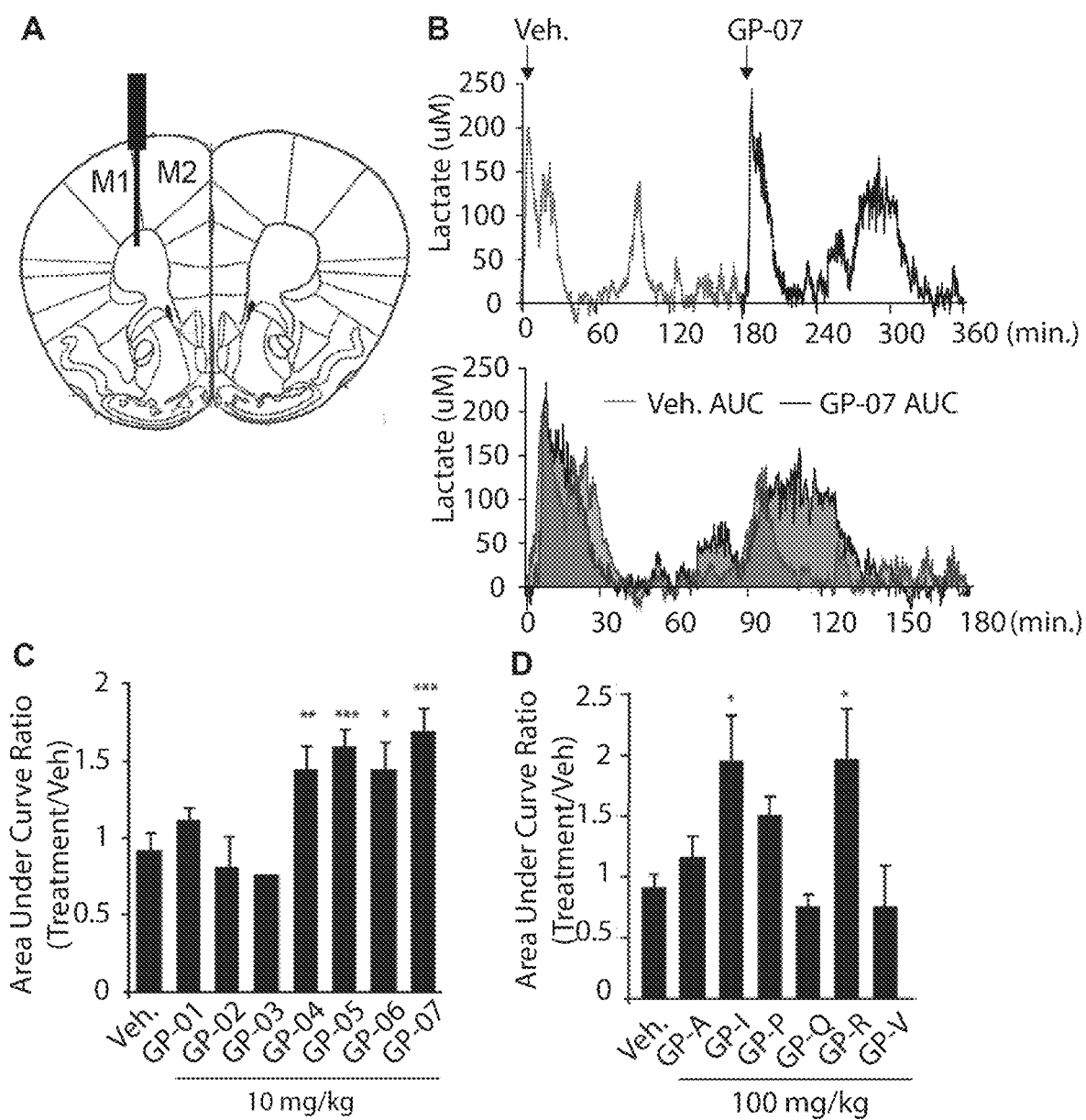
FIG. 9. (A) Localization of the lactate probe implanted in mouse brain. (B) Example of intracerebral lactate probe recording after administration of Vehicle, followed 3 h later by GP-07. Area under curve (AUC) were used to calculate treatment effect (Treatment AUC/Veh AUC). (C-D) AUC ratio after administration of Vehicle followed by Vehicle or tested drug at 10 mg/kg or 100 mg/kg; n=4-6.
Figure 10:
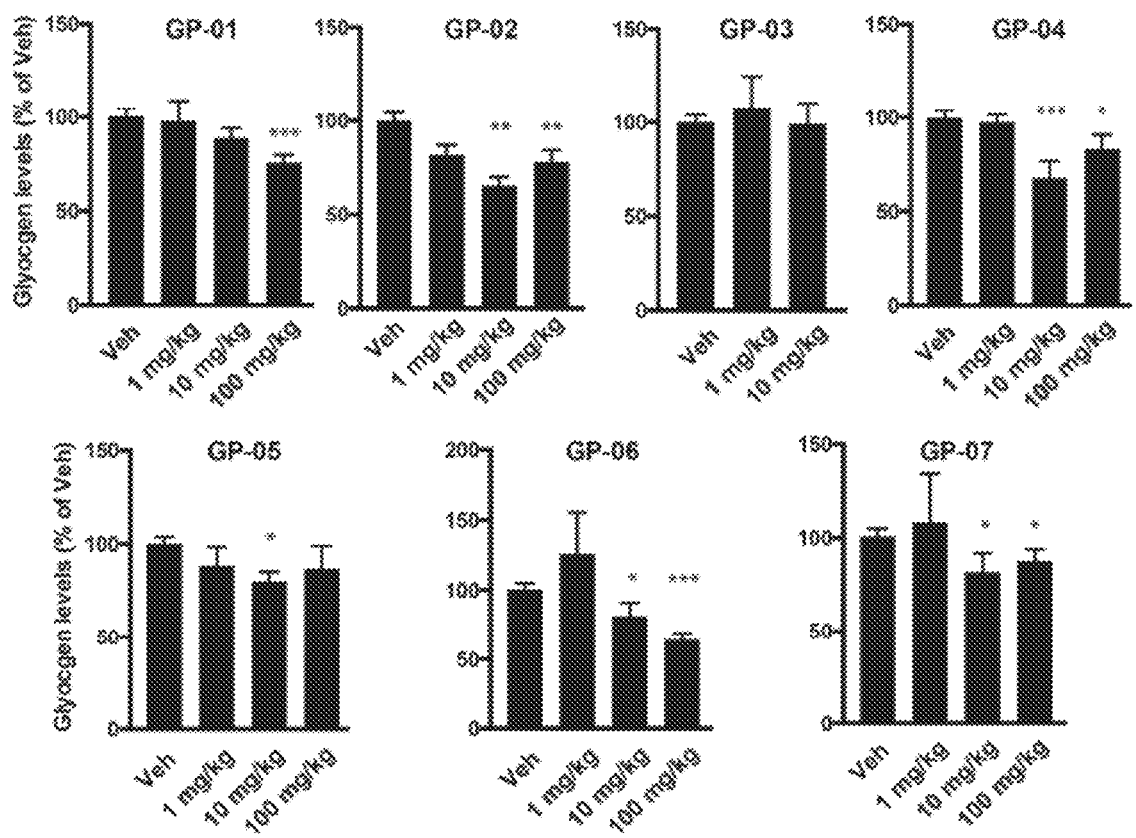
FIG. 10 shows glycogen levels in PFC (prefrontal cortex) at 3H after administration of the drug per os at 1, 10 or 100 mg/kg; n≥6.

To measure biological effect of lead molecules in vivo in the brain, lactate levels were quantified after administration of the drug by using lactate biosensors implanted in the cortex of freely moving mice. The results are shown in FIG. 9.

Summary

Significant increase of cerebral lactate with GP-04, GP-05, GP-06 and GP-07 at 10 mg/kg (Prestwick library), and family GP-I3, GP-P1 and GP-R1 at 100 mg/kg (10 mg/kg not yet tested; CDC54K library).

d. Pharmacodynamics—Glycogen Levels

Glycogen levels were measured in microwave-fixed mouse prefrontal cortex (PFC) (6 kW, 1 sec), which ensures enzymatic inhibition and stops glycogen degradation. Samples were then flash frozen before dosage.

First, glycogen levels were analyzed at 1 h, 3 h and 6 h after drug administration. The highest decreases in PFC glycogen were observed at 3H. This time point was subsequently used for dose-response experiments. Glycogen levels were quantified at 3H after administration with GP-01 to GP-07 at 1, 10 or 100 mg/kg. The results are shown in Figure Summary All tested molecules showed significant decrease of cerebral levels of glycogen at 10 mg/kg and/or 100 mg/kg, except for GP-03.

e. Pharmacokinetics (PK)

Figure 11A:
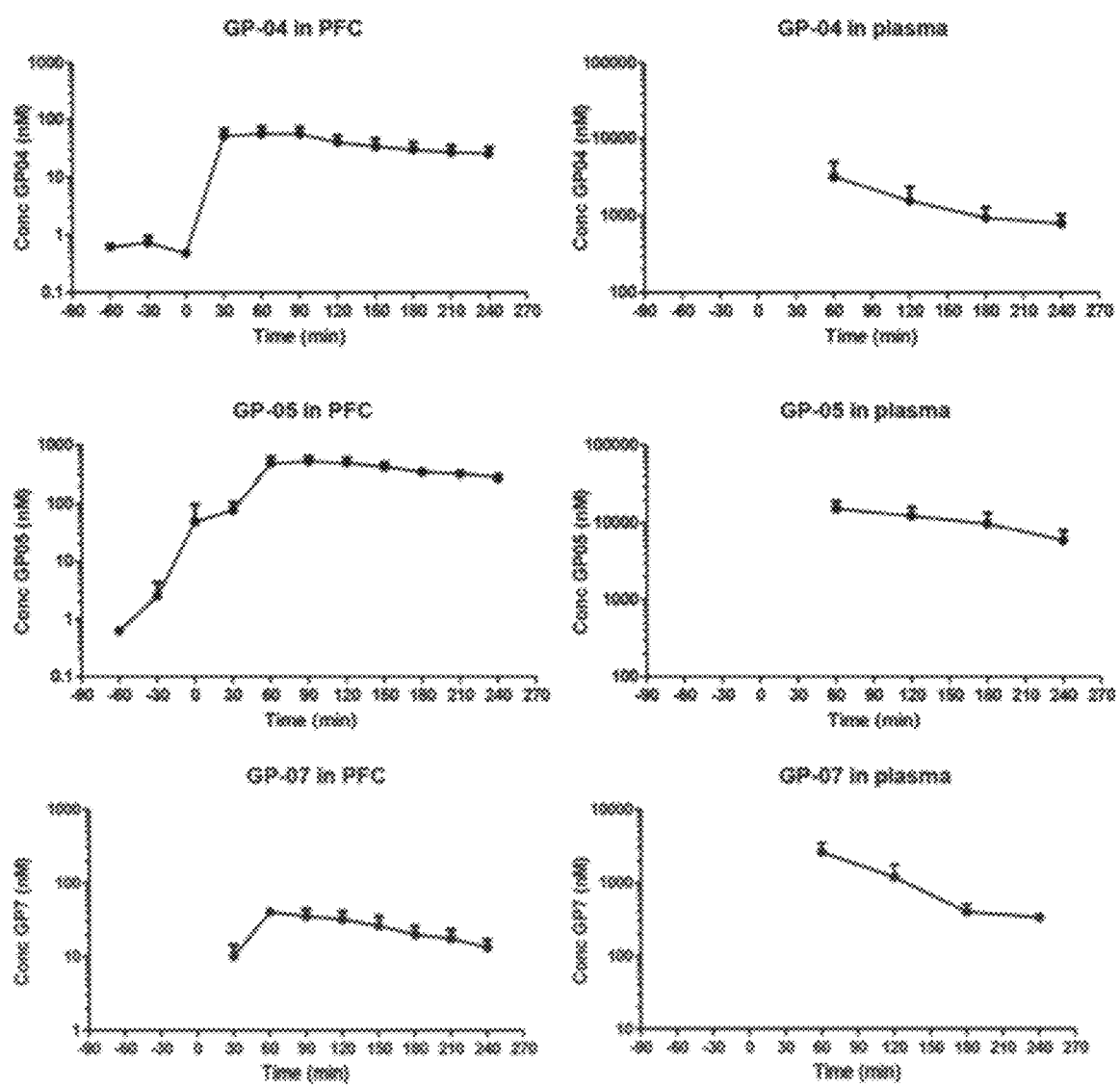
FIGS. 11A and 11B show the results after GP-04, GP-05, GP-07, GP-P1 and GP-R1 concentrations were measured in microdialysed samples of prefrontal cortex (left panels) and in the plasma (right panels) at 30 min intervals before and after compound's administration (100 mg/kg), n=5.
Figure 11B:
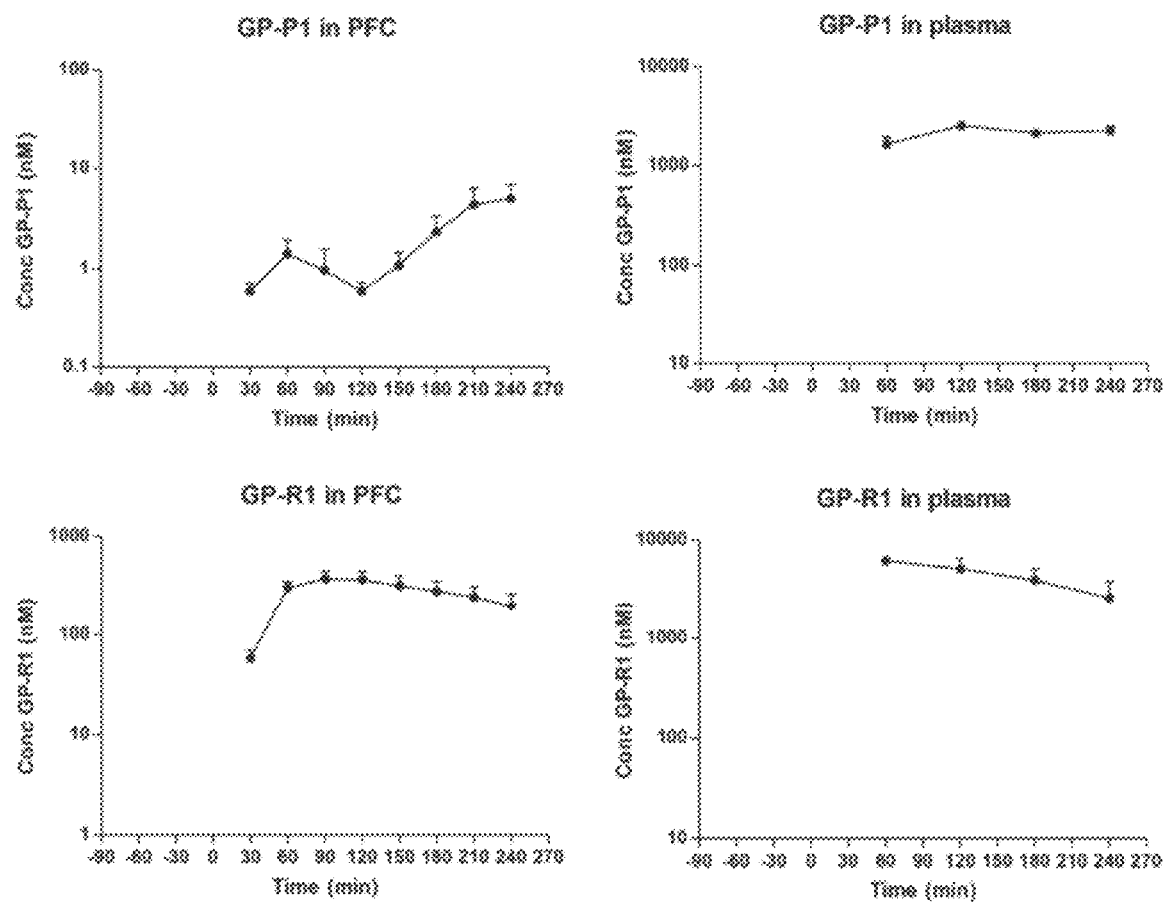

PK was measured for GP-04, GP-05, GP-07, GP-R1 and GP-P1 in the prefrontal cortex and plasma of wild type C56Bl/6 mice by CRO Brainsonline. The results are shown in FIGS. 11A and 11B.

Summary

Levels of GP-04, GP-05, GP-07 and GP-R1 are at therapeutic range (100 nM to 1 uM) and sustained over several hours in the prefrontal cortex after gavage with 100 mg/kg.

Figure 12:
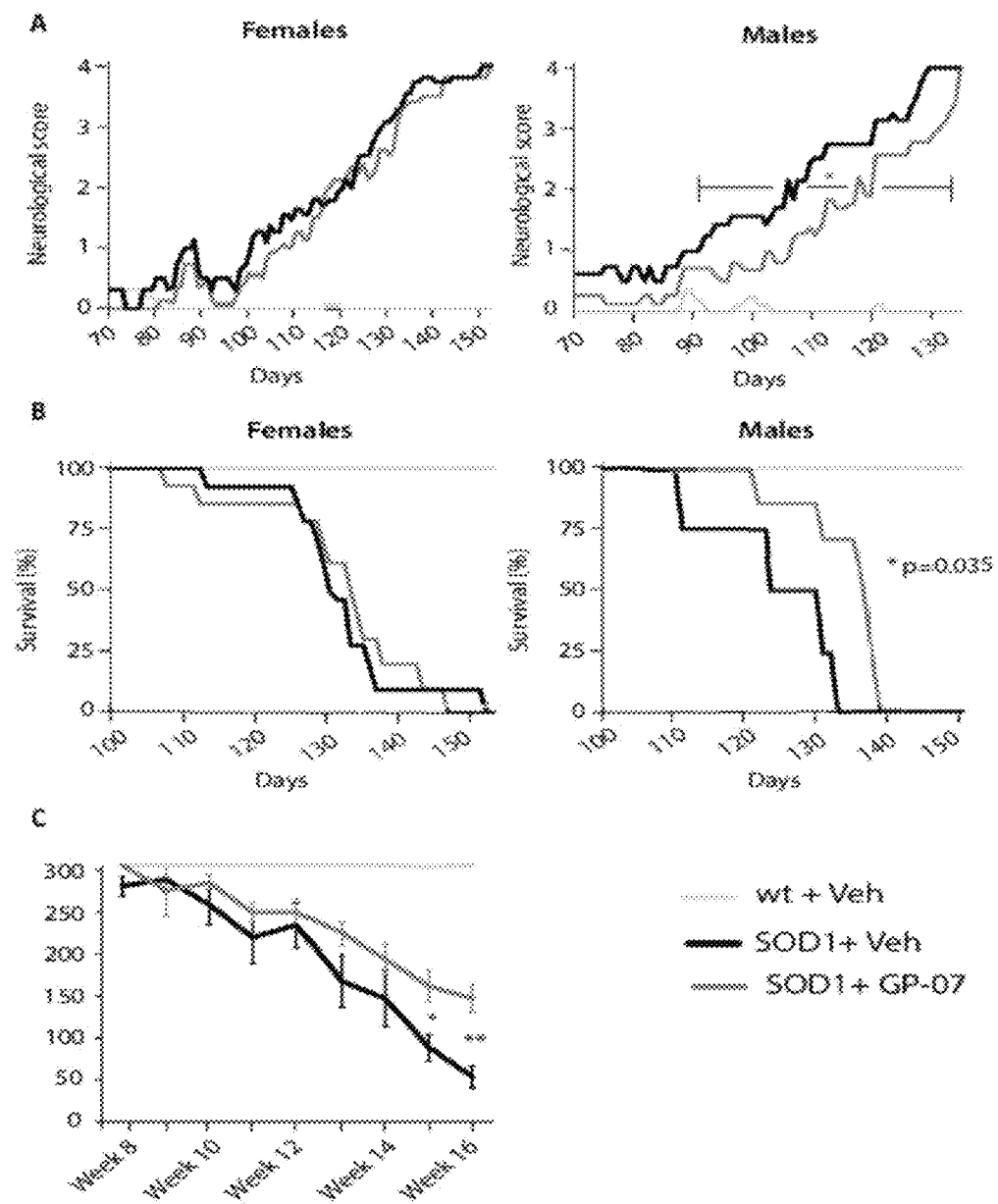
FIG. 12 shows the results after wild-type or SOD1 female or male mice were treated with Vehicle alone or GP-07 (10 mg/kg) from P30 until their sacrifice. Neurological scoring (A), survival (B) and grip test (C) are reported for each group (n≥12)
Figure 13:
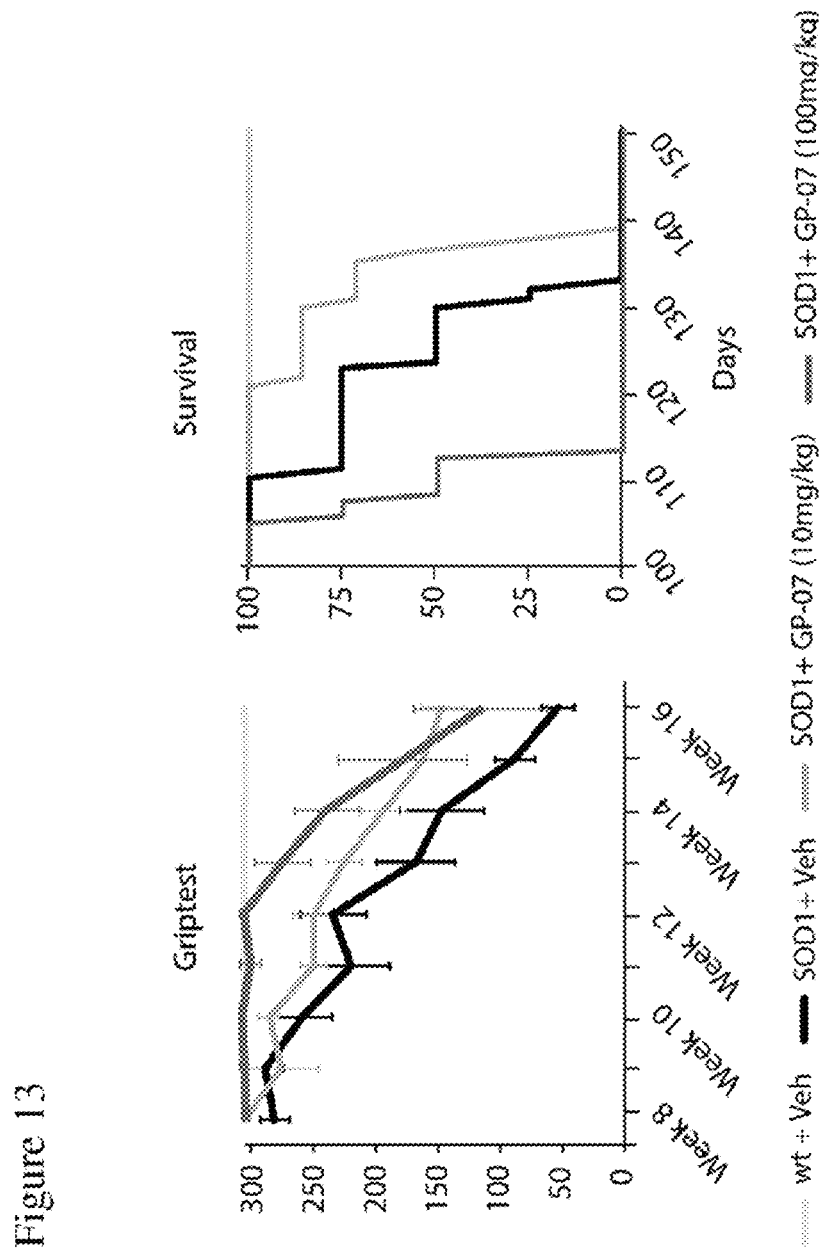
FIG. 13 shows the results after GP-07 was administered in male SOD1 mice at 10 mg/kg vs. 100 mg/kg. Muscle function (Griptest) and survival is shown; n≥12.
Figure 14:
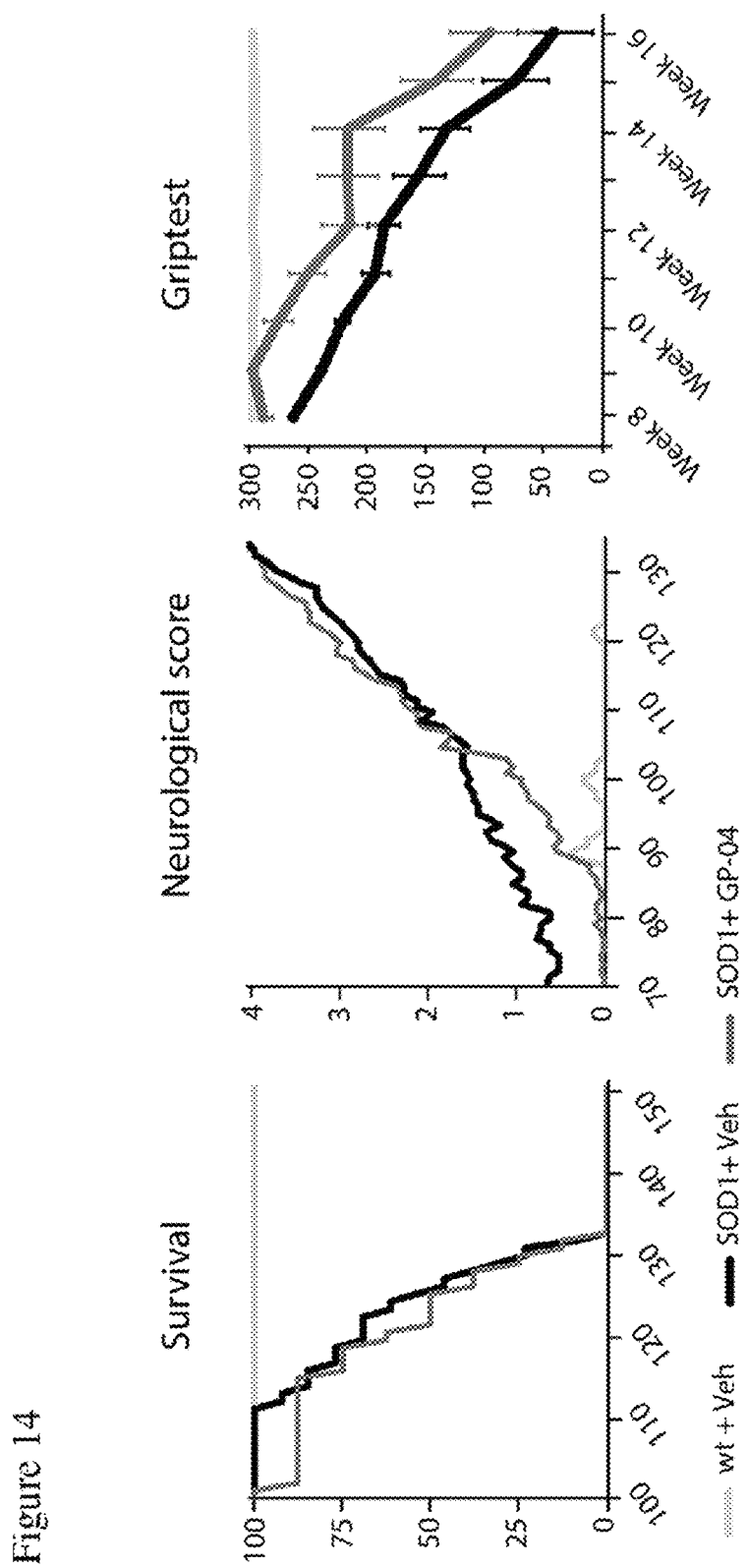
FIG. 14 shows the results of survival, neurological scoring and griptest of male mice treated with GP-04 at 10 mg/kg. Results were similar for female groups; n≥12.

GP-01, GP-02 and GP-P1 need chemical improvement to reach their target at therapeutic dose in the brain 4. SOD1 Mouse Model of ALS To test neuroprotective effect of lactate-enhancing drugs in ALS, SOD1 G93A mice were used. Drug was administered every day from P30 to final stage. Weight and neurological scoring (0-4) were recorded every day; muscular strength (griptest) and coordination (rotarod) were measured weekly. Results are shown in FIG. 12. Results for GP-07 alone are shown in FIG. 13 and for GP-04 alone are shown in FIG. 14.

Summary

Treatment with GP-07 at 10 mg/kg significantly improved motor function (griptest), neurological scoring and survival of SOD1 male mice. No effect was observed for GP-07 in female SOD1 mice.

Treatment with GP-07 at 100 mg/kg (SOD1 male mice) was significantly better than at 10 mg/kg until week 14, where it became toxic, resulting in accelerated death of animals.

Treatment with GP-04 at 10 mg/kg improved motor function in both male and female SOD1 mice, improved neurological scoring until P100, but had no effect on survival. GP-04 seems to have early rather than late effects.

Treatment with GP-05 at 10 mg/kg did not affect motor function, neurological score or survival.

Example 2: In Vitro Effects of Compounds of the Invention in Enhancing Glucose Uptake and Lactate Levels Secretion To assess for the effect of the compounds of the invention, those were tested in primary astrocytes, as described below. Secretion of lactate was measured directly in the extracellular medium, and indirectly through the acidification of extracellular medium using extracellular pH sensor SNARE-5F-(AND-6)-CAR (SNARF5). Glucose uptake was measured by quantification 2-deoxyglucose in the cell.

Cell Cultures

Primary cultures of cerebrocortical astrocytes were obtained from 1 to 2-day-old OF1 mouse pups (Charles River). Briefly, cortices were isolated and minced in small pieces under a dissecting microscope. The cells were incubated for 30 min at 37° C. in a solution containing 20 U/ml papain, 1 mM L-cysteine and 10 kU/ml DNase I. After dissociation, papain activity was stopped by the addition of fetal calf serum (FCS). Single-cell suspension was then obtained by mechanical dissociation, which consisted in cells trituration in a DMEM D7777 medium supplemented with 44 mm $NaHCO_3$, 10 ml/L antibiotic/antimycotic solution and 10% FCS. The cells were seeded at an average density of ~10'000 cells/cm2 on poly-D-lysine coated 96- or 12-well culture plates, depending on their use, and grown in DMEM D7777 medium supplemented with 44 mm NaHCO3, 10 ml/L antibiotic/antimycotic solution and 10% FCS at 37° C. in a humidified atmosphere containing 5% CO2/95% air. Culture medium was renewed twice a week. Cells were stimulated and harvested between DIV14 and DIV17, when confluence and cell growth were optimal.

Extracellular Medium Acidification (SNARF5)

Secretion of lactate was measured indirectly through the acidification of extracellular medium using extracellular pH sensor SNARE-5F-(AND-6)-CAR (SNARF5). After washing cells twice with stimulation medium (DMEM (D5030, Sigma), 1 mM $NaHCO_2$, and 5 mM Glucose, pH 7.4) at 37° C., cells were stimulated with compounds at a final concentration ranging from 10 nM to 30 µM in 50 µl per well of stimulation medium supplemented with 10 µM of SNARF5 (Life Technologies Corporation). Each compound was tested in two different plates for duplicates. After 90 min stimulation, fluorescence was read at exc. (excitation) 480 nm/emm. (emission) 580 nm and at exc 480 nm/emm. 630 nm. The ratio of fluorescence between 630 nm and 580 emission values, which is proportional to extracellular pH, was calculated. In each plate, 8 wells were used for negative controls (DMSO 0.1%) and 8 wells were used for positive controls (CCCP 2 µM in DMSO).

Figure 15:
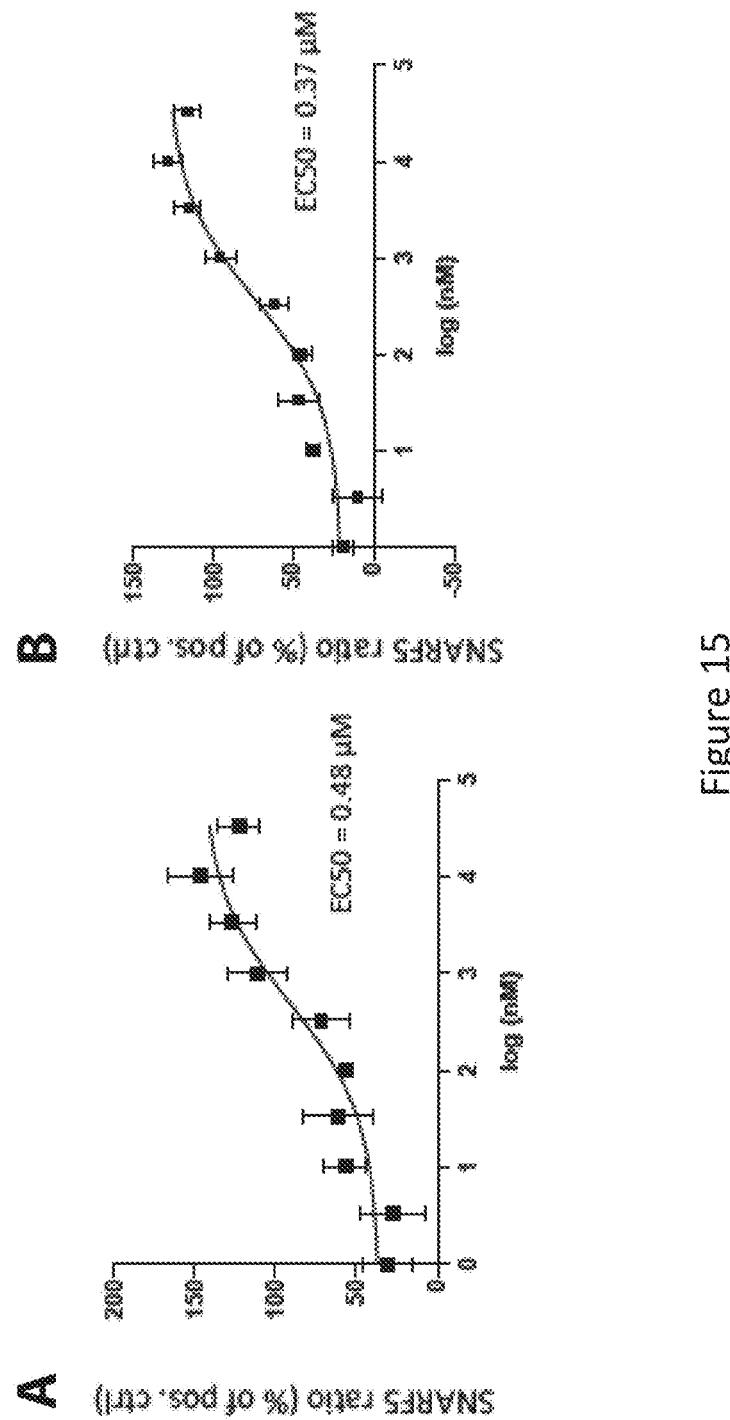
FIG. 15 shows the glycolytic index from primary cultures of astrocytes measured with extracellular fluorescent pH probe SNARF5 at 1.5H (A) and 3H (B) after treatment with compound of the invention (GP-A1) at concentrations ranging from 3 nM to 30 μM as described in Example 2, represented as % of positive control effect (carbonyl cyanide m-chlorophenyl hydrazone (CCCP), 2 μM)±SEM; n=4.

The extracellular medium acidification in primary mouse astrocytes treated with GP-A1 was quantified (FIG. 15). Extracellular medium acidification was measured over a period of 1.5 h and 3 h. GP-A1 was tested at different concentrations ranging from 3 nM to 30 µM to determine their EC50 and GP-A1 has an EC50 of 0.37 to 0.48 µM.

Extracellular Lactate Quantification

Secretion of L-lactate was measured in the extracellular medium of 96-well plated astrocytes after 90 min stimulation (at 37° C., in 5% CO2/95% air conditions) with Vehicle (DMSO), the compounds of the invention (100 nM to 100 µM) or positive control. The positive control consisted in carbonyl cyanide m-chlorophenyl hydrazine (CCCP, 2 µM), an inhibitor of mitochondrial oxidative phosphorylation that hence leads to enhanced glycolysis and secretion of lactate. Stimulation medium was composed of D5030 medium complemented with 5 mM D-glucose and 44 mM sodium bicarbonate, pH 7.2. To quantify lactate concentrations in the extracellular medium, 200 µl of a 0.2M Glycine-semicarbazide buffer (pH 10) containing 3 mM NAD and 1 U/ml LDH was added to each well of a 96-well plate containing 30 µl aliquots of extracellular medium. Samples were incubated at 37° C. for 1 h. Fluorescence intensity (340 nm excitation/450 nm emission), which represents the amount of NADH produced, was measured, and lactate concentration values were determined relative to a standard curve of L-lactate concentrations.

Figure 16:
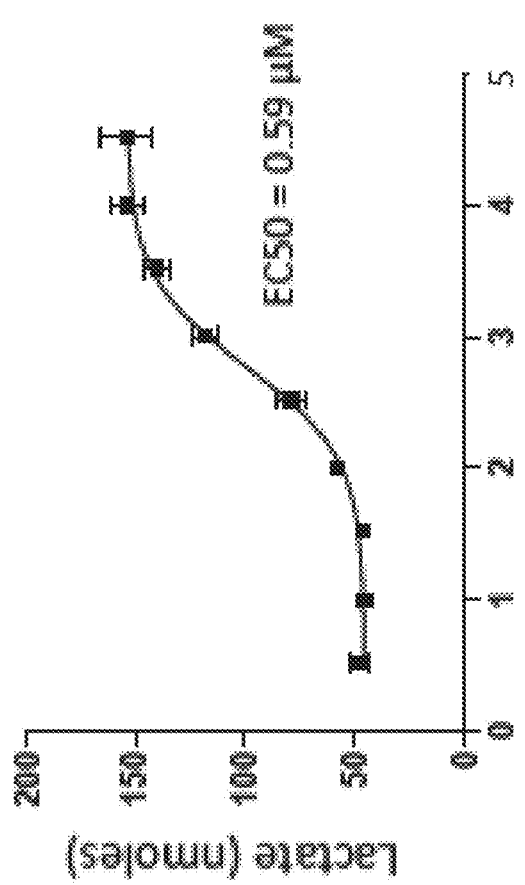
FIG. 16 shows the lactate release from primary cultures of astrocytes at 3H after treatment with compound of the invention (GP-A1) at concentrations ranging from 3 nM to 30 μM as described in Example 2, represented as nmoles±SEM; n=4.

The release of lactate from primary mouse astrocytes treated with GP-A1 was quantified (FIG. 5A and FIG. 16). Accumulation of lactate in the extracellular medium was measured over a period of 1.5 h. GP-A1 was tested at different concentrations ranging from 3 nM to 30 µM to determine their EC50 and GP-A1 has an EC50 of 0.59 µM.

Intracellular Glycogen Quantification

Astrocytes grown on 12-well plates were used for intracellular glycogen quantifications. Cells were stimulated with Vehicle (DMSO), with compounds of the invention (10 µM), or with a positive control for 180 min, at 37° C. 5% CO2/95% air in D5030 medium complemented with 5 mM D-glucose and 44 mM sodium bicarbonate (pH 7.2). Positive control consisted in an activator of glycogen phosphorylase, which hence triggers glycogen degradation in astrocytes (10 µM). At the end of the stimulation, medium was removed and replaced with 600 µl of 30 mM Tris HCl, and stored at −20° C.

Figure 20:
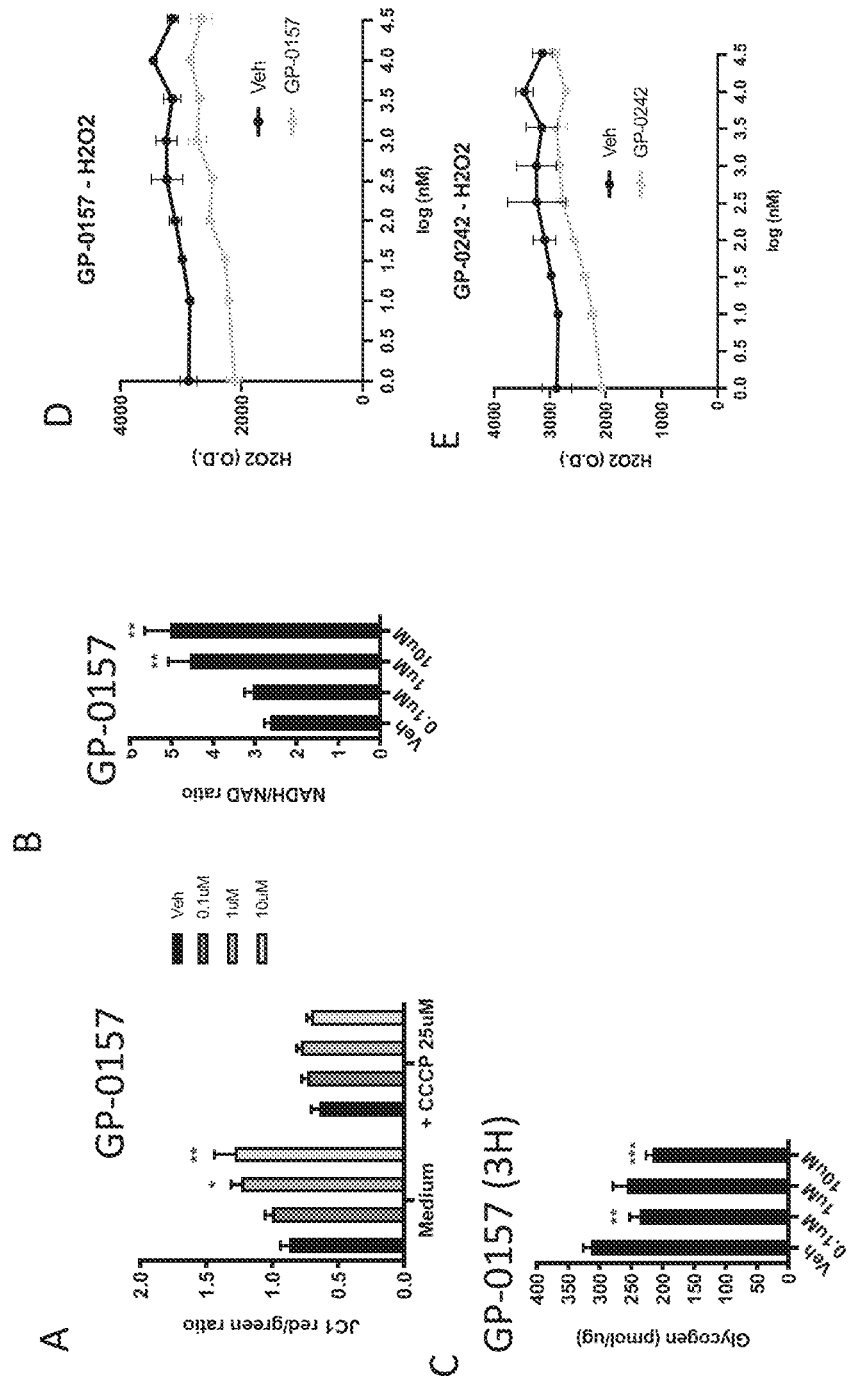
FIG. 20 shows inner membrane mitochondrial potential (JC1) after treatment with Veh (01.% DMSO), or GP-0157 (0.1, 1 and 10 μM), alone or with the mitochondrial decoupling agent CCCP (25p M) (A), NADH/NAD+ ratio after treatment with Veh or GP-0157 (0.1, 1 and 10 μM) (B), intracellular glycogen concentrations after treatment with Veh or GP-0157 (0.1, 1 and 10 μM) (C), and $H_2O_2$ release after treatment with Veh, GP-0157 or GP-0242 (10 nM to 30 μM) (D and E).

First, the amount of proteins in each sample was quantified to assess whether harvested astrocytes from primary cell cultures yielded enough and equivalent amounts of proteins on each replicates. Proteins were quantified using the micro BCA Protein Assay kit (Thermo Scientific), according to manufacturer's instructions. Next, intracellular glycogen concentrations were quantified using a 250 µl-aliquot of the same stimulated, thawed, and sonicated cell lysate. After an incubation period of 30 min at 90° C. and 400 rpm, 28 µl of a 0.1M acetic acid/sodium acetate buffer (pH 4.6) was added to each lysate aliquots, which were then separated in two. Each split aliquots received either 5 µl of amyloglucosidase or $H_2O$, and incubated for 120 min at 37° C. After centrifugation at 16'000G for 5 min, 20 µl of supernatant were placed in a 96-well plate, to which 150 µl of a mix containing 0.67 mM ATP, 0.67 mM NADP, 1.8% hexokinase/glucose-6-phosphate dehydrogenase in a 0.1M Tris Buffer-HCl/3.3 mM magnesium (pH 8.1) buffer was added. Fluorescence intensity (340 nm excitation/440 nm emission) was measured using a Safire 2 spectrophotometer. Glucose concentrations were assessed relative to a glucose standard curve, and glycogen concentrations were calculated by subtracting glucose values of samples that had received amyloglucosidase (i.e. that had degraded their glycogen stores) to samples that had not. Intracellular levels of glycogen, which is the main source of glucose storage in the brain, were analyzed in primary astrocytes after treatment with compounds of interest (10 µM, 3 h) (FIG. 5B), and compound GP-0157 (0.1, 1, 10 µM, 3 h) (FIG. 20). It was observed that compounds GP-A1, E1, F1, GI, H1, I3, N1, P1, Q1, U1, V1 and GP-0157 significantly enhance the mobilization of intracellular glycogen, which may act, at least in part, as the energy fuel necessary to produce lactate by astrocytes during the process of aerobic glycolysis.

2-Deoxyglucose (2DG) Uptake

Figure 17:
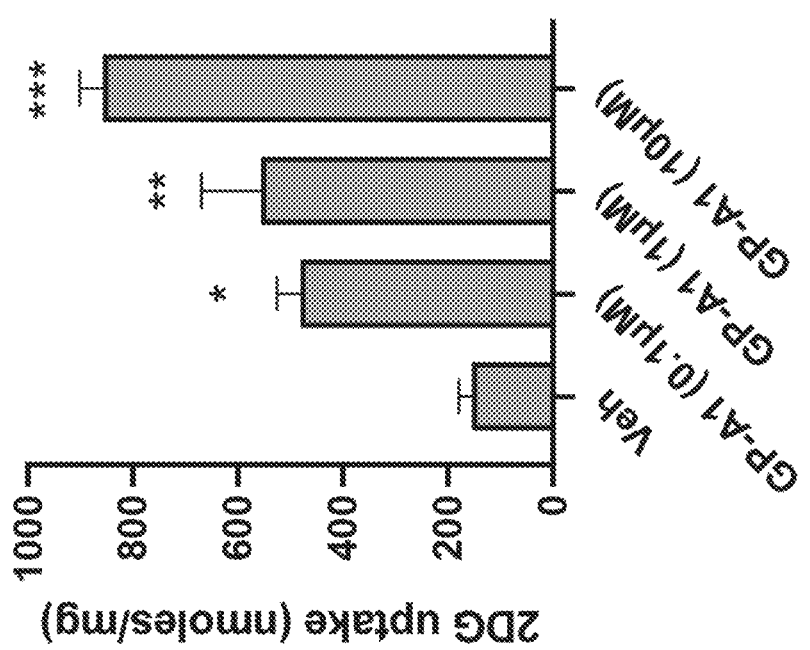
FIG. 17 shows glucose uptake assessed by quantification of intracellular 2-deoxyglucose in primary cultures of astrocytes measured at 30 min after stimulation with compound of the invention (GP-A1) at concentrations ranging from 100 nM to 10 μM as described in Example 2, represented as nmoles per mg of total proteins±SEM; n=4.
Figure 19:
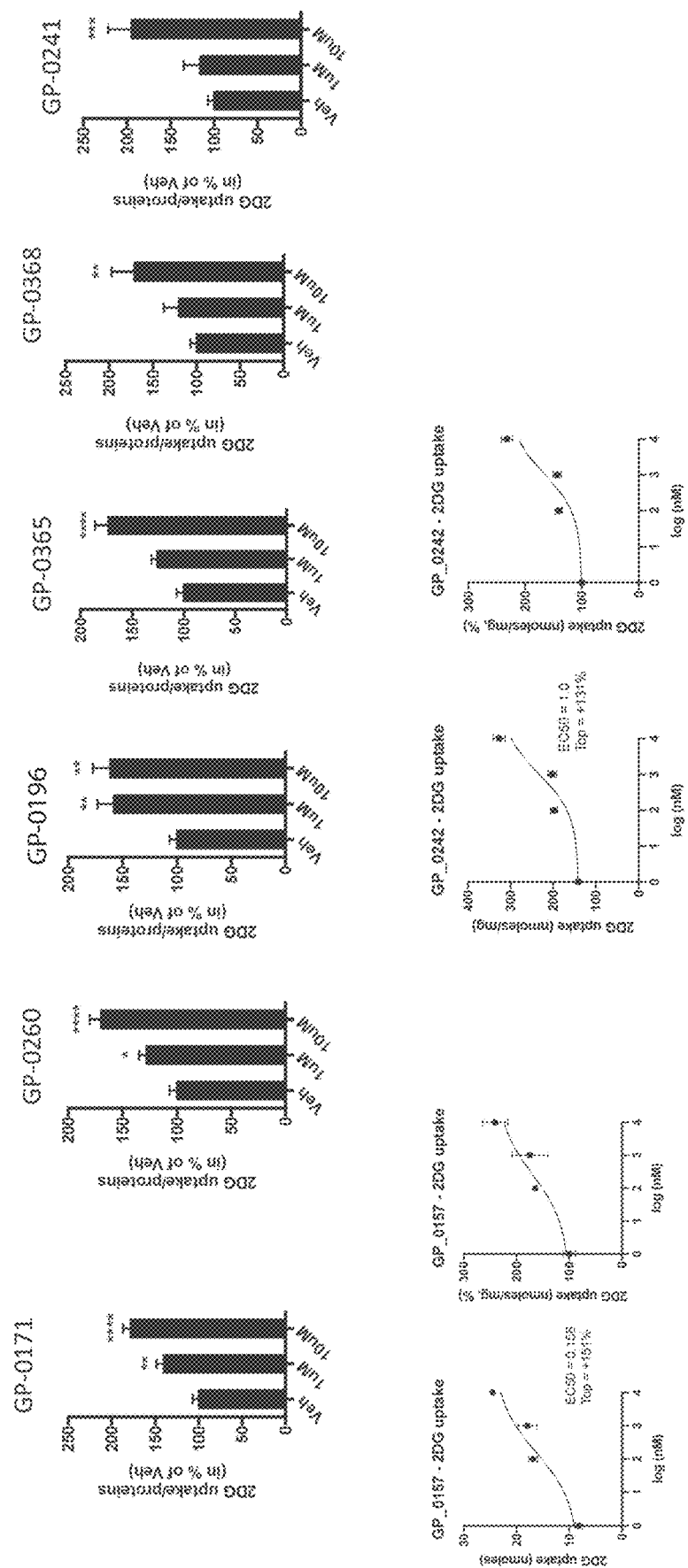
FIG. 19 shows glucose uptake assessed by quantification of intracellular 2-deoxyglucose in primary cultures of astrocytes measured at 30 min after stimulation with compounds of the invention GP-0171, GP-0260, GP-0196 GP-0365, GP-368 and GP-0241 at concentrations ranging from 1 to 10 μM (upper panel) and compounds of the invention GP-0157 and GP-0242 at concentrations ranging from 100 nM to 10 μM (lower pane) described in Example 2, represented as nmoles per mg of total proteins (% of Veh)±SEM; n=4.

Astrocytes grown on 12-well plates were used. 1 day after having replaced 25 mM glucose-containing medium with 5 mM containing glucose medium (DIV13), 2DG uptake was measured after treatment for 30 min with Vehicle (0.1% DMSO) or with the GP-A1 (concentrations of 0.1, 1 or 10 µM) (FIG. 17) or with compounds GP-0157, GP-0171, GP-0196, GP-0241, GP-0242, GP-0260, GP-0365 and GP-0368 (FIG. 19). During treatment, 1 mM 2DG was added to the medium for assessment of 2DG uptake. At the end of the stimulation, medium was removed and replaced with 150 µl NaOH 0.1M, and stored at −20° C. After thawing, cells were collected using cell scraper and heated for 40 min at 85° C. Then, 150 ul HCl 0.1M and TAE buffer 200 mM was added to each condition. 20 µl were added to a transparent 96-well plate and 2DG was quantified by addition of a reaction solution containing 50 mM TAE, 50 mM KCl, 0.02% BSA, 0.1 mM NADP, 0.2 U/ml diaphorase, 2 mM resazurin and 20 U/ml glucose-6-phosphate dehydrogenase. Concentration of 2DG in samples were calculated by comparison with standard curve of deoxy-glucose-6-phophate ranging from 0 to 1 nmoles and expressed relative to total protein content (mg) that was quantified using BCA procedure.

Inner Membrane Mitochondrial Potential (JC1)

Astrocytes grown for 13 days in vitro (DIV13) were used to measure inner membrane mitochondrial potential after treatment with Vehicle (0.1% DMSO) or Compound GP-0157 (0.1, 1, 10 µM) (FIG. 20). A solution containing 6.25 µg/ml JC-1 dye (Invitrogen) was added to each well of 12-well culture plates 15 minutes before the end of stimulation. JC-1 dye exhibits mitochondrial potential-dependent fluorescence. At low potential, monomers are formed and display green fluorescence while at high potential, JC-1 aggregates and displays red fluorescence. After 1.5H incubation, fluorescence was measured using Tecan fluorescence microplate reader (594 nm emission/497 nm excitation (red), and 527 nm emission/497 nm excitation (green). The mitochondrial potential level was quantified by calculating the ratio of both fluorescence values. Addition of CCCP (25 µM), a mitochondrial decoupling agent, has been used as control showing reduction of mitochondrial potential.

H2O2 Production

Hydrogen peroxide (H2O2) accumulated in cell culture medium was detected enzymatically with Amplex red $H_2O_2$ probe (Invitrogen). Astrocytes grown in 96-well plates were treated for 6 hours in stimulation medium complemented with 10 µM Amplex red and 1 U/ml HRP (Sigma Aldrich) with GP-0157 or GP-0242 (10 nM to 30 µM) (FIG. 20). Oxidation of Amplex red is catalyzed by the horseradish peroxidase (HRP) in presence of H2O2, which results in fluorescent resorufin that was quantified using Tecan fluorescence microplate reader (excitation 545 nm, emission 590 nm). Data indicate that neither GP-0157 or GP-0242 affect $H_2O_2$ production.

Intracellular NADH/NAD+Redox Ratio

Intracellular NADH/NAD+redox ratio was measured using enzymatic quantification after treatment with Veh (0.1% DMSO) or GP-0157 (0.1, 1 or 10 µM) for 1.5 hours. Briefly, cells were washed in PBS after treatment and 600 µl of 20 mM $NaHCO_3$/100 mM Na2CO3 buffer (pH10) containing 1 M nicotinamide was added followed by flash freeze to disrupt cell membranes. Once thawed, samples were separated in two parts: one for the dosage of NADH+NAD+ and the other one for NADH only. Samples for NADH detection were heated at 60° C. for 30 minutes to destroy NAD+. Next, 150 µl of a reaction mix composed of 133 mM bicine, 5.33 mM EDTA, 0.56 mM MTT, 2.21 mM PES, 667 mM ethanol and 40 U/ml alcohol dehydrogenase was added to each of the 50 µl samples. Reduction of MTT was followed by measuring absorbance at 570 mm using Tecan fluorescence microplate reader, and NAD+ values were calculated by subtracting NADH from NADH+NAD+ values.

Figure 21:
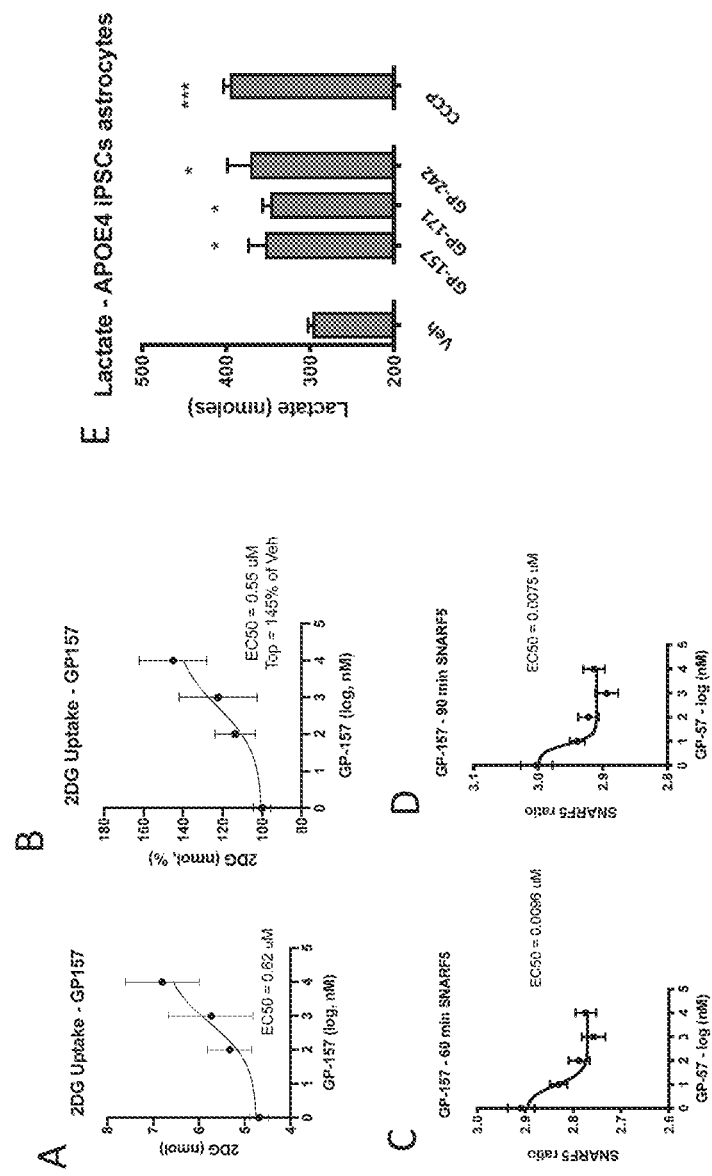
FIG. 21 shows glucose uptake from human-derived iPSCs astrocytes after treatment with Veh (01.% DMSO), or GP-0157 (0.1, 1 and 10 μM) for 30 min (A and B), extracellular medium acidification (SNARF5) after treatment with Veh (01.% DMSO), or GP-0157 (0.1, 1 and 10 μM) for 60 min to 90 min (C and D), and extracellular lactate levels in human-derived iPSCs astrocytes from APOE4 carrier patient treated with Vehicle (0.1% DMSO), GP-0157, GP-0171, GP-0242 (each 10 μM), or CCCP (2 μM) for 90 min (E).

Human-Derived Induced-Pluripotent Stem Cells (IPSCs) Astrocytes 2-deoxyglucse (2DG) uptake, extracellular medium acidification (SNARF5) were quantified, as previously described, in human-derived induced-pluripotent stem cells (iPSCs) astrocytes purchased from NCardia. Astrocytes grown on 12-well plates were used to quantify 2DG uptake. 1 day after having replaced 25 mM glucose-containing medium with 5 mM containing glucose medium (DIV8), 2DG uptake was measured after treatment for 30 min with Vehicle (0.1% DMSO) or with the compound GP-0157 (concentrations of 0.1, 1 or 10 µM) (FIG. 21). Secretion of lactate was measured indirectly through the acidification of extracellular medium using extracellular pH sensor SNARE-5F-(AND-6)-CAR (SNARF5) in human iPSCS astrocytes grown in 96-well plates, as previously described, after treatment with GP-0157 for 60 min or 90 min (FIG. 21). Lactate secretion was quantified, as previously described, in human-derived induced-pluripotent stem cells (iPSCs) astrocytes from a patient with Alzheimer's disease that was carrier of the APOE4 allele, which were purchased from Axol Bioscience. The release of lactate after treated with Veh (0.1% DMSO) or Compounds GP-0157, GP-0171 or GP-0242 (10 µM each), or CCCP (2 uM) was quantified (FIG. 21). Accumulation of lactate in the extracellular medium was measured over a period of 1.5 h. Data indicate that GP-0157, GP-0171 and GP-0242 lead to significant lactate release from APOE4 iPSCs astrocytes.

Example 3: In Vivo Effects of Compounds of the Invention

To assess for the effect of the compounds of the invention on brain extracellular levels of lactate, they have been tested though the in vivo monitoring of glucose and lactate levels after treatment with the compounds of the invention as follows.

All experiments were carried out in strict accordance with the Swiss Federal Guidelines for Animal Experimentation and were approved by the Cantonal Veterinary Office for Animal Experimentation (Canton of Vaud or Canton of Geneva, Switzerland). Adult male C57Bl/6J wild-type mice weighting 18-28 g (8 weeks of age) were used (Charles River). Animals were housed in groups of 3-5 in polypropylene cages (30×40×15 cm) with wire mesh top in a temperature (22±2° C.) and humidity (55±15%) controlled environment on a 12 hour light cycle (07.00-19.00 h lights on), except after surgeries when animal were housed individually. The samples (Vehicle or compounds of the invention) were administered per os (gavage) in a solution made of water supplemented with 0.4% hydroxypropyl methylcellulose (HPMC) Methocel 4KM (w/v) and 0.25% Tween-20 (v/v), as previously described (Thackaberry et al., 2010, Toxicol Sci., 117(2):485-92). Concentrations of the compounds tested ranged from 10 to 100 mg/kg.

In Vivo Pharmacodynamics—Glucose and Lactate Biosensors

Figure 22:
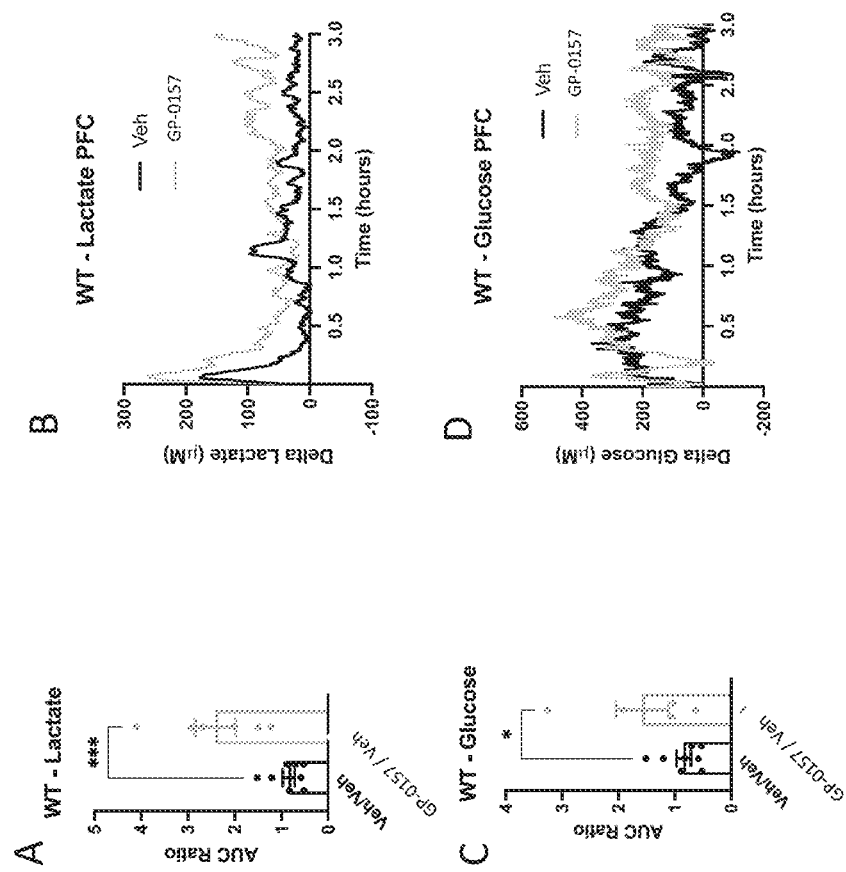
FIG. 22 shows the monitoring of cerebral lactate concentrations (A and B) and glucose concentrations (C and D). A: Comparison of Veh/Veh lactate AUC ratio (Veh., n=5) and GP-0157/Veh lactate AUC ratio (n=6). B: Fluctuation of lactate levels for a duration of 3 hours after oral administration of Veh or compound of the invention (GP-0157) at a dose of 10 mg/kg. C: Comparison of Veh/Veh lactate AUC ratio (Veh., n=4) and GP-0157/Veh glucose AUC ratio (n=5). D: Fluctuation of glucose levels for a duration of 3 hours after oral administration of Veh or compound of the invention (GP-0157) at a dose of 10 mg/kg. Data are the average±SEM. * p<0.05; ** p<0.01 (unpaired bilateral Student's t-test).

Cerebral extracellular levels of glucose and lactate were monitored in vivo using glucose and lactate biosensors (Pinnacle Technology), respectively, according to the manufacturer's instructions. Cannulae were surgically implanted in the cerebral prefrontal cortex (coordinates: −1.0 mm (to bregma), lateral+/−1.0 mm (to midline), ventral −1.0 mm (to dura)) 1) of isoflurane-anesthetized mice 5 to 7 days prior experiment. After surgery, mice were monitored closely and received analgesic treatment for at least 4 days. After mice had fully recovered from surgery, compounds of the invention or vehicle were administered per os as previously described and cerebral levels of extracellular lactate were dynamically recorded for 6 hours using lactate biosensors. Mice were administered vehicle alone first, followed 3 hours later by vehicle or GP-A1 (10 mg/kg), or GP-0157 (10 mg/kg). Concentrations of cerebral extracellular glucose and lactate were calculated from glucose and lactate probe electric signals, respectively, using post-calibration values. Each signal of glucose or lactate fluctuation after compound (or vehicle) administration was expressed as a fold change relative to the glucose or lactate fluctuation following the first administration of vehicle alone, each animal hence being its own control. Area Under the Curve (AUC) of glucose or lactate concentration curves were calculated using Graphad Prism and the ratio of AUC after drug over Vehicle administration was calculated. Extracellular concentrations of glucose or L-lactate were measured in real time in freely moving animals for 3 hours after administration of Vehicle or GP-0157 (FIG. 22). Results indicate that treatment with GP-0157 at 10 mg/kg significantly increases extracellular glucose and lactate levels in the brain of treated mice, as compared to vehicle (FIG. 22).

It will be appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination. It will also be appreciated by persons skilled in the art that the present invention is not limited by what has been particularly shown and described hereinabove. Rather the scope of the invention is defined only by the claims which follow.

Appendix I
Family A
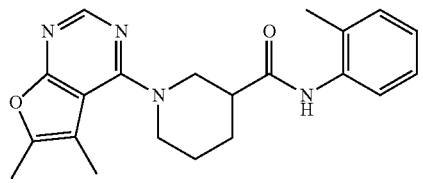
unknown chirality
A1
| | |
|---|---|
| CatalogID | F228-0422 |
| Score | 1.057299178434214 |
| Score_SNA RF | 0.7701853152834461 |
| Score_LAC TATE | 0.6363638379469401 |
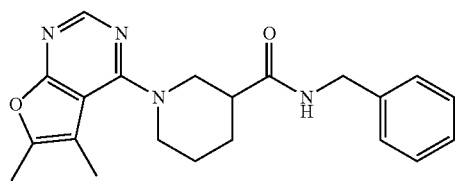
unknown chirality
| | |
|---|---|
| CatalogID | F228-0365 |
| Score | 1.0347684901720595 |
| Score_SNA RF | 0.942866402185284 |
| Score_LAC TATE | 0.9000644924199342 |
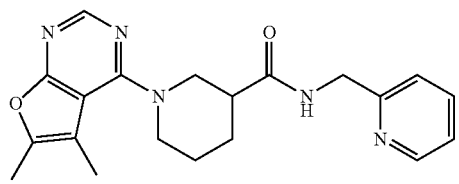
unknown chirality
A2
| | |
|---|---|
| CatalogID | F228-0350 |
| Score | 0.9575255500229646 |
| Score_SNA RF | 1.0109377915014888 |
| Score_LAC TATE | 1.022932010836847 |
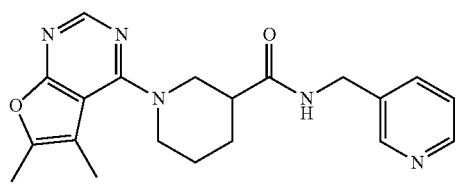
unknown chirality
| | |
|---|---|
| CatalogID | F228-0351 |
| Score | 0.5920192604665382 |
| Score_SNA RF | 0.819975594094603 |
| Score_LAC TATE | 0.898536677505049 |

-continued
Appendix I
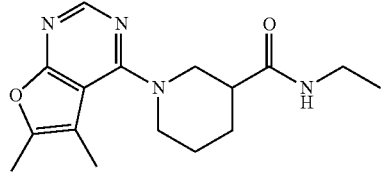
unknown chirality
A3
| | |
|---|---|
| CatalogID | F228-0534 |
| Score | 0.35368992473276867 |
| Score_SNA | 0.5203267581394291 |
| RF | |
| Score_LAC | 0.3387117841389162 |
| TATE | |
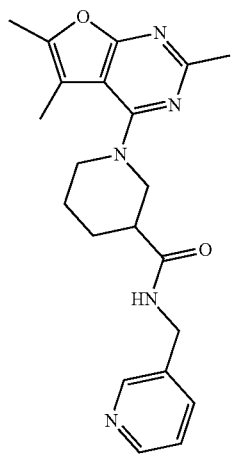
unknown chirality
| | |
|---|---|
| CatalogID | F228-0856 |
| Score | 0.18647369720387383 |
| Score_SNA | 0 |
| RF | |
| Score_LAC | 0 |
| TATE | |
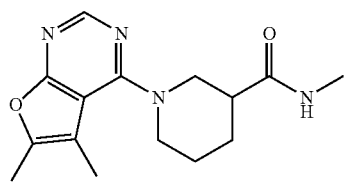
unknown chirality
| | |
|---|---|
| CatalogID | F228-0541 |
| Score | 0.15277599688164334 |
| Score_SNA | 0.36093980523381536 |
| RF | |
| Score_LAC | 0 |
| TATE | |

-continued
Appendix I
Family C
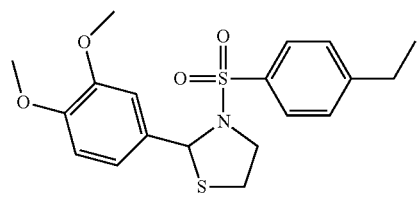
unknown chirality
C1
| | |
|---|---|
| CatalogID | T5463586 |
| Score | 0.7706610463405941 |
| Score_SNA | 0.5553240531901028 |
| RF | |
| Score_LAC | 0.3935782163943059 |
| TATE | |
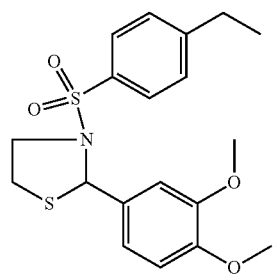
unknown chirality
C2
| | |
|---|---|
| CatalogID | 4052-4304 |
| Score | 0.4940426943326044 |
| Score_SNA | 0.44913944402072394 |
| RF | |
| Score_LAC | 0.433527881002696 |
| TATE | |
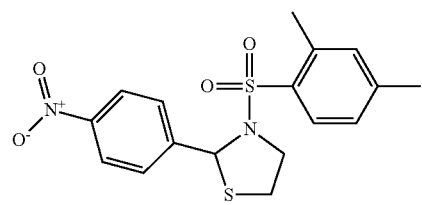
unknown chirality
| | |
|---|---|
| CatalogID | T5464782 |
| Score | 0.27666864801157476 |
| Score_SNA | NOT_TESTED |
| RF | |
| Score_LAC | NOT_TESTED |
| TATE | |

Appendix I
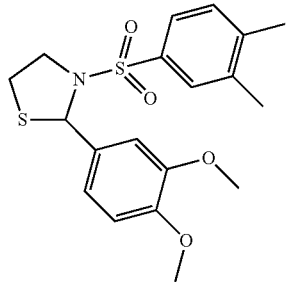
unknown chirality
| | |
|---|---|
| CatalogID | F1462-0491 |
| Score | 0.27239461193483955 |
| Score_SNA | 0 |
| RF | |
| Score_LAC | 0 |
| TATE | |
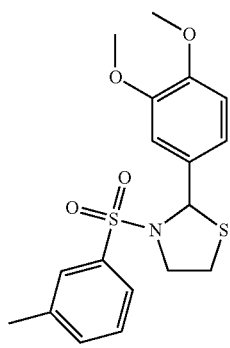
C3
unknown chirality
| | |
|---|---|
| CatalogID | T5463658 |
| Score | 0.2721822922258924 |
| Score_SNA | 0.4683062878625885 |
| RF | |
| Score_LAC | 0.37725037983836096 |
| TATE | |
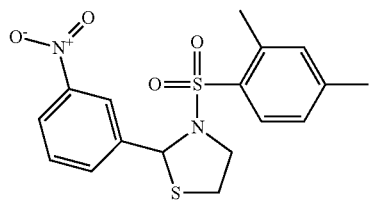
unknown chirality
| | |
|---|---|
| CatalogID | T5463709 |
| Score | 0.24395452401314383 |
| Score_SNA | NOT_TESTED |
| RF | |
| Score_LAC | NOT_TESTED |
| TATE | |

Appendix I
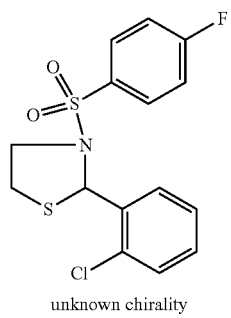 [SMILES: O=S(=O)(c1ccc(F)cc1)N1CCSC1c1ccccc1Cl]
unknown chirality
| | |
|---|---|
| CatalogID | 4052-4279 |
| Score | 0.15619544912441768 |
| Score_SNA RF | NOT_TESTED |
| Score_LAC TATE | NOT_TESTED |
Family E
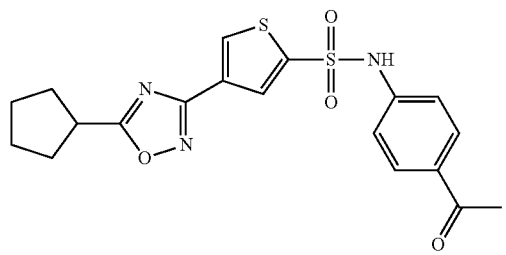 [SMILES: CC(=O)c1ccc(NS(=O)(=O)c2cc(-c3noc(C4CCCC4)n3)cs2)cc1]
| | |
|---|---|
| CatalogID | L287-1577 |
| Score | 1.1941965522070632 |
| Score_SNA RF | 1.059135232742917 |
| Score_LAC TATE | 1.2154260492545208 |
E2
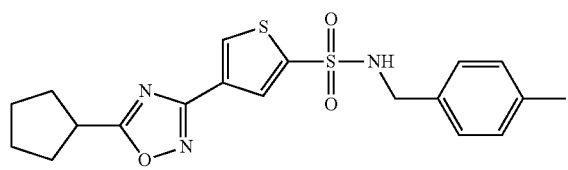 [SMILES: Cc1ccc(CNS(=O)(=O)c2cc(-c3noc(C4CCCC4)n3)cs2)cc1]
| | |
|---|---|
| CatalogID | L287-1641 |
| Score | 0.7717661404373028 |
| Score_SNA RF | 0.6259648254476997 |
| Score_LAC TATE | 0.8035139544488019 |
E1
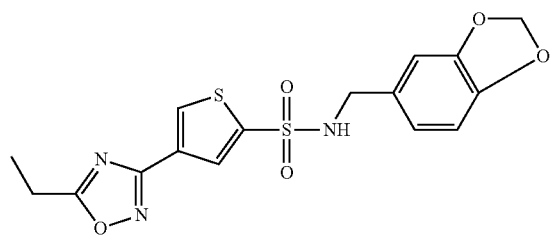 [SMILES: CCc1nc(-c2csc(S(=O)(=O)NCc3ccc4c(c3)OCO4)c2)no1]
| | |
|---|---|
| CatalogID | L287-0468 |
| Score | 0.597113045524908 |
| Score_SNA RF | 0.6592317135195043 |
| Score_LAC TATE | 0.6179394415979561 |

Appendix I
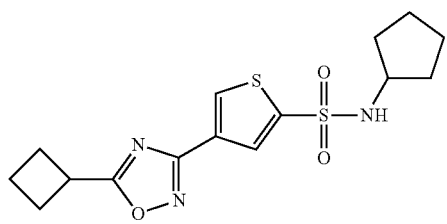 [SMILES: O=S(=O)(NC1CCCC1)c1cc(-c2noc(C3CCC3)n2)cs1]
E3
| CatalogID | L287-1221 |
|---|---|
| Score | 0.5155681934872474 |
| Score_SNA RF | 0.5994953570205764 |
| Score_LAC TATE | 0.6601796155644594 |
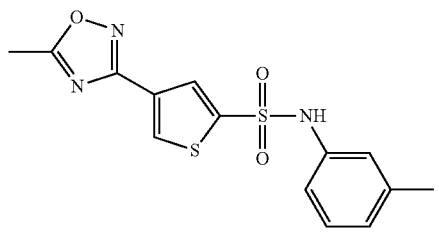
E4
| CatalogID | L287-0220 |
|---|---|
| Score | 0.35245757621656926 |
| Score_SNA RF | 0.5828763746073296 |
| Score_LAC TATE | 1.5779605457379224 |
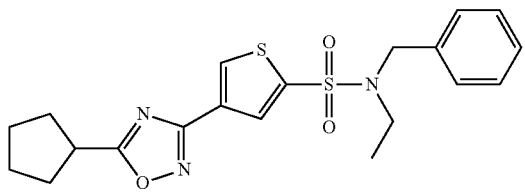 [SMILES: CCN(Cc1ccccc1)S(=O)(=O)c1cc(-c2noc(C3CCCC3)n2)cs1]
| CatalogID | L287-1758 |
|---|---|
| Score | 0 |
| Score_SNA RF | NOT_TESTED |
| Score_LAC TATE | NOT_TESTED |
Family F (1/3)
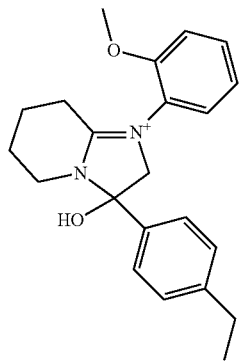
unknown chirality
| CatalogID | K404-0672 |
|---|---|
| Score | 1.245294619968429 |
| Score_SNA | 1.0137401503371428 |

Appendix I (continued)
| | |
|---|---|
| RF | |
| Score_LAC | 1.3564152530836169 |
| TATE | |
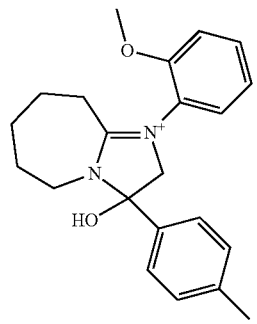
F1
unknown chirality
| | |
|---|---|
| CatalogID | K404-0834 |
| Score | 1.1228184799775751 |
| Score_SNA | 1.022137061560947 |
| RF | |
| Score_LAC | 1.6126572223635596 |
| TATE | |
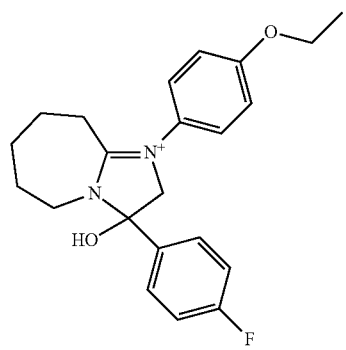
F3
unknown chirality
| | |
|---|---|
| CatalogID | K404-0885 |
| Score | 1.0632020143035092 |
| Score_SNA | 0.9078708580769379 |
| RF | |
| Score_LAC | 0.9014739788461116 |
| TATE | |
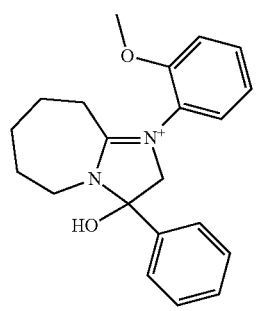
F2
unknown chirality
| | |
|---|---|
| CatalogID | K404-0838 |
| Score | 1.030964579539889 |
| Score_SNA | 0.8328339622087815 |
| RF | |
| Score_LAC | 1.0509377415150052 |
| TATE | |

Appendix I -continued
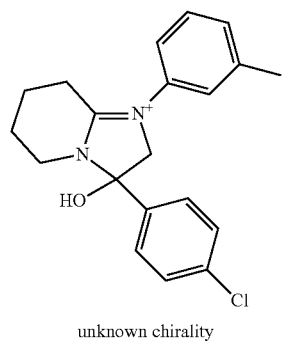 [SMILES: Cc1cccc([N+]2=C3CCCCN3C(O)(c3ccc(Cl)cc3)C2)c1]
unknown chirality
F4
| CatalogID | K404-0800 |
|---|---|
| Score | 0.9729596471903071 |
| Score_SNA | 0.7385730422972991 |
| RF | |
| Score_LAC | 0.8385058046355538 |
| TATE | |
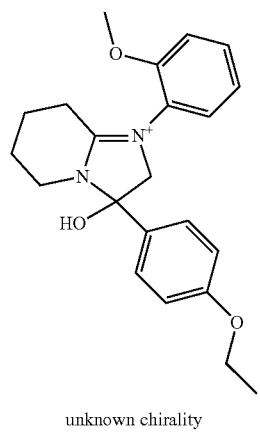 [SMILES: CCOc1ccc(C2(O)C[N+](c3ccccc3OC)=C3CCCCN32)cc1]
unknown chirality
F5
| CatalogID | K404-0673 |
|---|---|
| Score | 0.9305928701278892 |
| Score_SNA | 0.975128679661051 |
| RF | |
| Score_LAC | 2.0243685786220746 |
| TATE | |
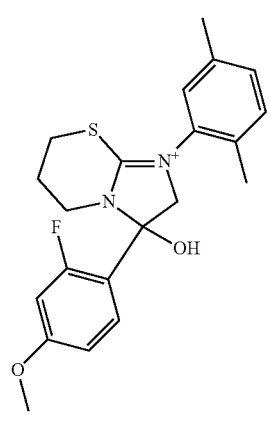
unknown chirality
| CatalogID | K404-0183 |
|---|---|
| Score | 0.895586999693623 |
| Score_SNA | 0 |

Appendix I
| | |
|---|---|
| RF Score_LAC TATE | 0 |
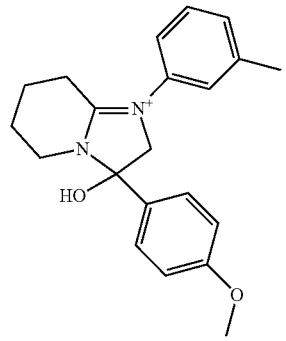
unknown chirality
| | |
|---|---|
| CatalogID | K404-0796 |
| Score | 0.8606816213733115 |
| Score_SNA | 0.6402071193972154 |
| RF Score_LAC TATE | 0 |
F6
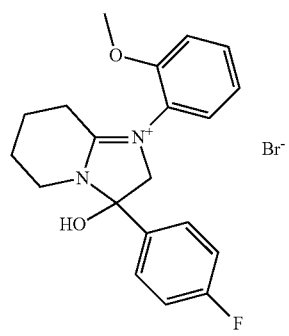
unknown chirality
| | |
|---|---|
| CatalogID | F0524-0338 |
| Score | 0.7360202432760756 |
| Score_SNA | 0.6339637469346097 |
| RF Score_LAC TATE | 1.584755646134777 |
F7
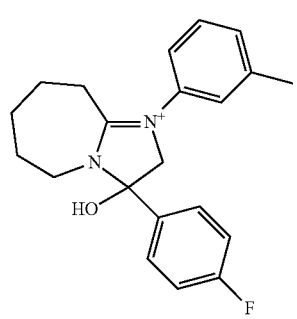
unknown chirality
| | |
|---|---|
| CatalogID | K404-0910 |
| Score | 0.7255494073967776 |
| Score_SNA | 0.587837672209965 |
| RF Score_LAC TATE | 0.6219124056361738 |

Appendix I
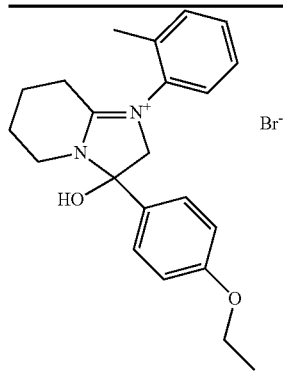
unknown chirality
| | |
|---|---|
| CatalogID | F0524-0511 |
| Score | 0.7004940551078669 |
| Score_SNA | 0.5555152736849276 |
| RF | |
| Score_LAC | 0 |
| TATE | |
F8
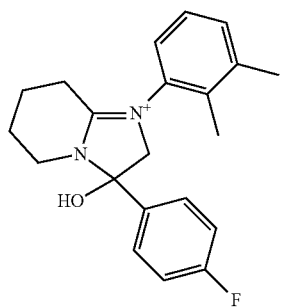
unknown chirality
| | |
|---|---|
| CatalogID | K404-0685 |
| Score | 0.6788640765960137 |
| Score_SNA | 0.6561775100211843 |
| RF | |
| Score_LAC | 0.6821438644674629 |
| TATE | |
Family F (2/3)
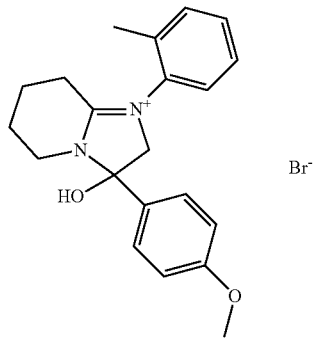
unknown chirality
| | |
|---|---|
| CatalogID | F0524-0507 |
| Score | 0.6120319085702075 |
| Score_SNA | 0.4490842880759446 |
| RF | |
| Score_LAC | 0 |
| TATE | |

-continued
Appendix I
F9
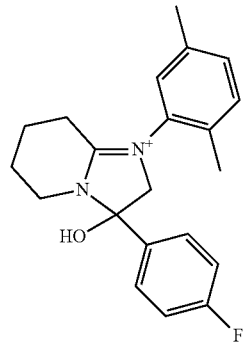
unknown chirality
| | |
|---|---|
| CatalogID | K404-0697 |
| Score | 0.5955558493686706 |
| Score_SNA | 0.5122850686232165 |
| RF | |
| Score_LAC | 0.6526243981885684 |
| TATE | |
F10
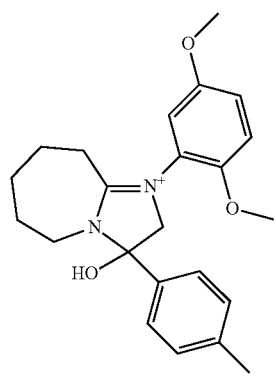
unknown chirality
| | |
|---|---|
| CatalogID | K404-0855 |
| Score | 0.5849297608174214 |
| Score_SNA | 0.49441470822619804 |
| RF | |
| Score_LAC | 0.6276573393012033 |
| TATE | |

-continued
Appendix I
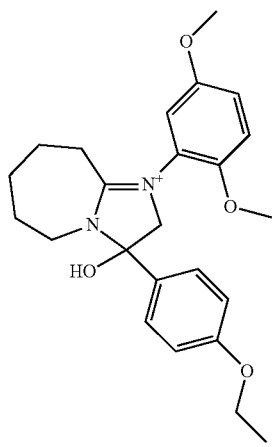
unknown chirality
F11
| CatalogID | K404-0860 |
|---|---|
| Score | 0.5789542930848154 |
| Score_SNA RF | 0.6137065353631177 |
| Score_LAC TATE | 0.4765859547890614 |
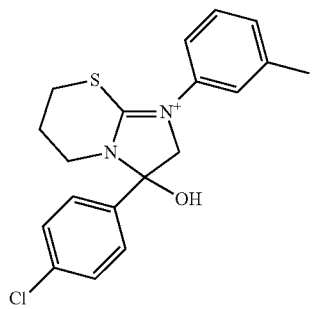
unknown chirality
| CatalogID | F0522-0533 |
|---|---|
| Score | 0.5572373039563334 |
| Score_SNA RF | 0.47052230558046815 |
| Score_LAC TATE | 0 |
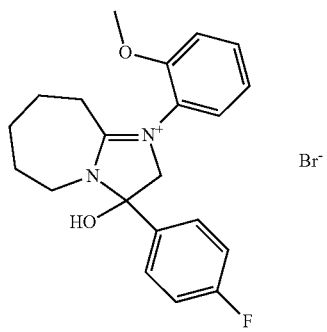
unknown chirality
F12
| CatalogID | F0524-0611 |
|---|---|
| Score | 0.5339163037048325 |

| Appendix I | |
|---|---|
| Score_SNA RF | 0.5953907345776432 |
| Score_LAC TATE | 1.5467390894846487 |
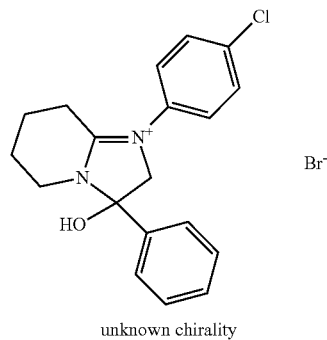 [SMILES: OC1(c2ccccc2)C[N+](c2ccc(Cl)cc2)=C2CCCCN21 ; [Br-]]
unknown chirality
| | |
|---|---|
| CatalogID | F0524-0488 |
| Score | 0.5117725163099112 |
| Score_SNA RF | 0.3488588317771778 |
| Score_LAC TATE | 0 |
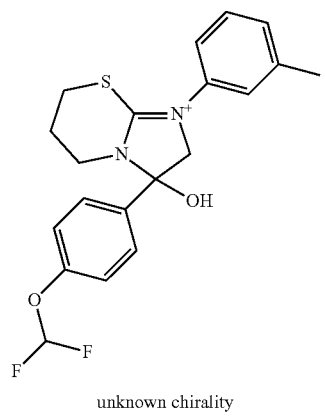 [SMILES: Cc1cccc([N+]2=C3SCCCN3C(O)(c3ccc(OC(F)F)cc3)C2)c1]
unknown chirality
| | |
|---|---|
| CatalogID | K404-0400 |
| Score | 0.3634628173863156 |
| Score_SNA RF | NOT_TESTED |
| Score_LAC TATE | NOT_TESTED |
F13
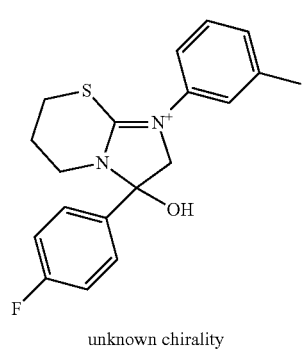 [SMILES: Cc1cccc([N+]2=C3SCCCN3C(O)(c3ccc(F)cc3)C2)c1]
unknown chirality
| | |
|---|---|
| CatalogID | K404-0394 |
| Score | 0.3467068112662994 |

-continued
Appendix I
| | |
|---|---|
| Score_SNA RF | 0.3308952459455954 |
| Score_LAC TATE | 0.44285355839996976 |
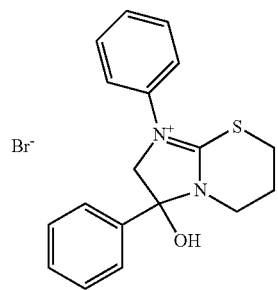
unknown chirality
| | |
|---|---|
| CatalogID | T0507-8442 |
| Score | 0.26840498230024956 |
| Score_SNA RF | NOT_TESTED |
| Score_LAC TATE | NOT_TESTED |
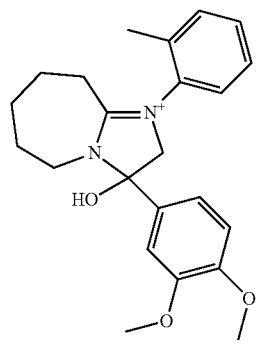
unknown chirality
| | |
|---|---|
| CatalogID | K404-0906 |
| Score | 0.1913767711510388 |
| Score_SNA RF | 0 |
| Score_LAC TATE | 0 |

Appendix I
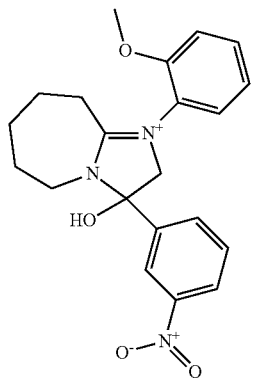
unknown chirality
| | |
|---|---|
| CatalogID | K404-0842 |
| Score | 0.169031494172405 |
| Score_SNA RF | 0.2021699692940943 |
| Score_LAC TATE | 0 |
Family F (3/3)
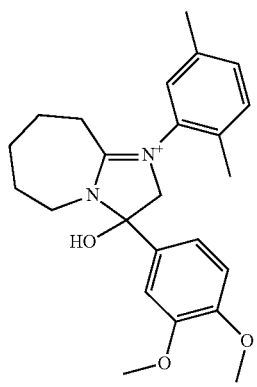
unknown chirality
| | |
|---|---|
| CatalogID | K404-0852 |
| Score | 0 |
| Score_SNA RF | NOT_TESTED |
| Score_LAC TATE | NOT_TESTED |
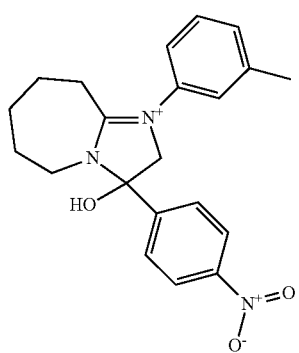
unknown chirality
| | |
|---|---|
| CatalogID | K404-0914 |
| Score | 0 |

|  |  |
| --- | --- |
| Appendix I | |
| Score_SNA RF | NOT_TESTED |
| Score_LAC TATE | NOT_TESTED |
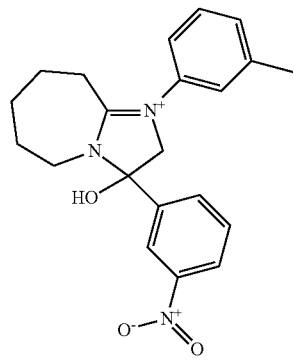
unknown chirality
| | |
| --- | --- |
| CatalogID | K404-0915 |
| Score | 0 |
| Score_SNA RF | NOT_TESTED |
| Score_LAC TATE | NOT_TESTED |
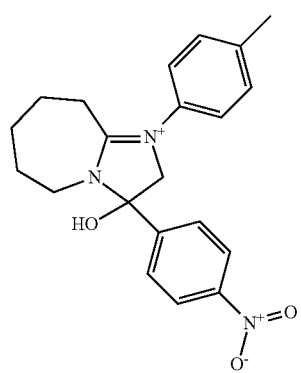
unknown chirality
| | |
| --- | --- |
| CatalogID | K404-0828 |
| Score | 0 |
| Score_SNA RF | NOT_TESTED |
| Score_LAC TATE | NOT_TESTED |

| Appendix I |
|---|
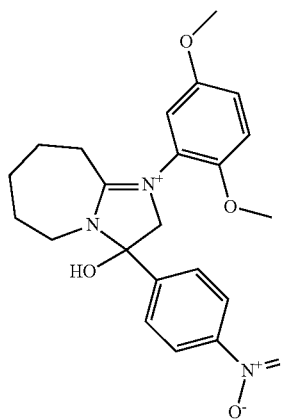
unknown chirality
| | |
|---|---|
| CatalogID | K404-0863 |
| Score | 0 |
| Score_SNARF | NOT_TESTED |
| Score_LACTATE | NOT_TESTED |
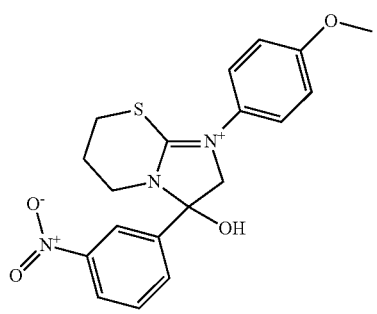
unknown chirality
| | |
|---|---|
| CatalogID | K404-0277 |
| Score | 0 |
| Score_SNARF | NOT_TESTED |
| Score_LACTATE | NOT_TESTED |
| Family F2 |
|---|
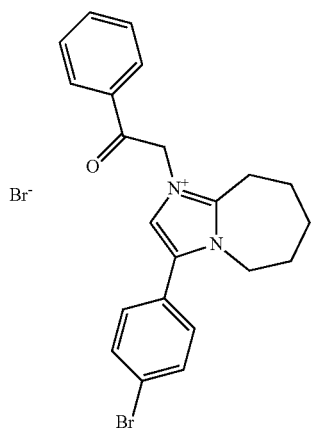 [SMILES: [Br-] ; O=C(C[n+]1cc(-c2ccc(Br)cc2)n2c1CCCCC2)c1ccccc1]
| | |
|---|---|
| CatalogID | T0500-4648 |
| Score | 1.0945456348515448 |

-continued
| Appendix I | |
|---|---|
| Score_SNA RF | 1.0336425682807298 |
| Score_LAC TATE | 1.1162396727491835 |
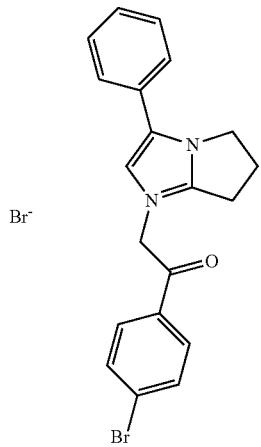
| CatalogID | T0502-5560 |
| Score | 1.0186741404078639 |
| Score_SNA RF | 0.8504454491757103 |
| Score_LAC TATE | 0.8523597142194843 |
| Family G | |
|---|---|
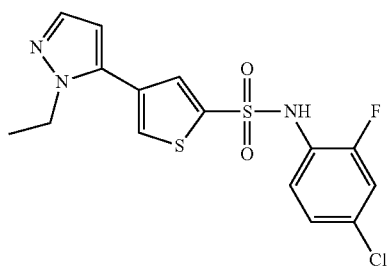 [SMILES: CCn1nccc1-c1csc(S(=O)(=O)Nc2ccc(Cl)cc2F)c1]
G1
| CatalogID | L924-1031 |
| Score | 0.9285626587383733 |
| Score_SNA RF | 0.8713278858649929 |
| Score_LAC TATE | 1.6324528424335565 |
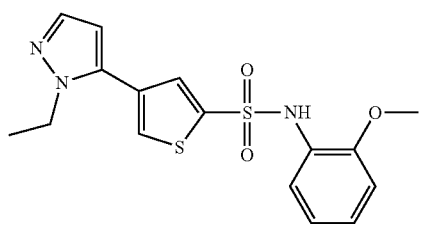 [SMILES: CCn1nccc1-c1csc(S(=O)(=O)Nc2ccccc2OC)c1]
G3
| CatalogID | L924-1088 |
| Score | 0.7850885946772328 |
| Score_SNA RF | 0.8834624954983981 |
| Score_LAC TATE | 0.9105778321422937 |

-continued
Appendix I
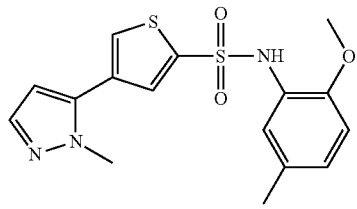 [SMILES: COc1ccc(C)cc1NS(=O)(=O)c1cc(-c2ccnn2C)cs1]
G2
| CatalogID | L924-0830 |
|---|---|
| Score | 0.7820290835785534 |
| Score_SNA | 0.7153389708932881 |
| RF | |
| Score_LAC | 0.9168484167457057 |
| TATE | |
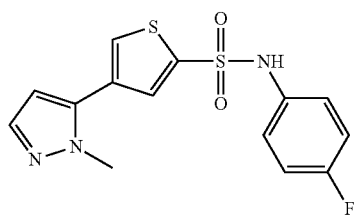 [SMILES: Cn1nccc1-c1csc(S(=O)(=O)Nc2ccc(F)cc2)c1]
G4
| CatalogID | L924-0760 |
|---|---|
| Score | 0.6913326730640292 |
| Score_SNA | 0.7695123014835685 |
| RF | |
| Score_LAC | 0.7898333850310828 |
| TATE | |
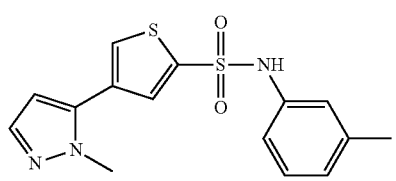 [SMILES: Cc1cccc(NS(=O)(=O)c2cc(-c3ccnn3C)cs2)c1]
G5
| CatalogID | L924-0884 |
|---|---|
| Score | 0.6560790709954556 |
| Score_SNA | 0.7507266569597015 |
| RF | |
| Score_LAC | 0.7362417013630416 |
| TATE | |
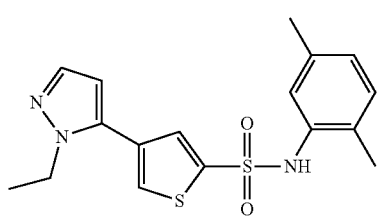 [SMILES: CCn1nccc1-c1csc(S(=O)(=O)Nc2cc(C)ccc2C)c1]
G6
| CatalogID | L924-0988 |
|---|---|
| Score | 0.5266337896361102 |
| Score_SNA | 0.6651843383172913 |
| RF | |
| Score_LAC | 0.6138869900753379 |
| TATE | |

| Appendix I |
|---|
| Family H |
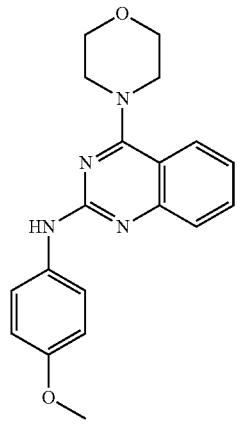 [SMILES: COc1ccc(Nc2nc(N3CCOCC3)c3ccccc3n2)cc1]
H1
CatalogID T0508-5190
Score 0.4587604202347154
Score_SNA_RF 0.4029122435484707
Score_LAC_TATE 0.2892472208157204
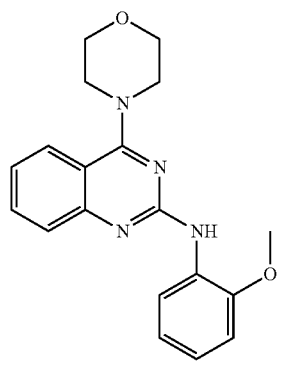 [SMILES: COc1ccccc1Nc1nc(N2CCOCC2)c2ccccc2n1]
CatalogID F3007-0009
Score 0.19840697203688884
Score_SNA_RF 0
Score_LAC_TATE 0
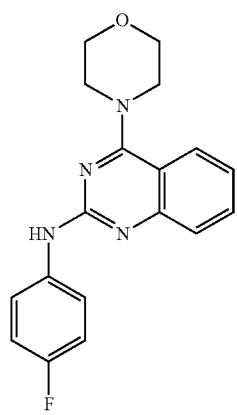 [SMILES: Fc1ccc(Nc2nc(N3CCOCC3)c3ccccc3n2)cc1]
CatalogID T0508-5193
Score 0.19512447407576727

Appendix I
| | |
|---|---|
| Score_SNA RF | 0.30521182534409874 |
| Score_LAC TATE | 0 |
Family I (1/2)
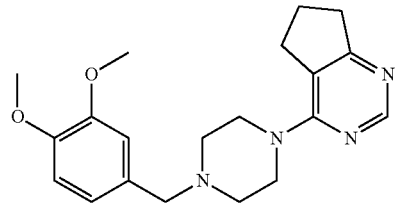 [SMILES: COc1ccc(CN2CCN(c3ncnc4c3CCC4)CC2)cc1OC]
| | |
|---|---|
| CatalogID | T636-2007 |
| Score | 1.0151791427998305 |
| Score_SNA RF | 0.8595986424585913 |
| Score_LAC TATE | 0.9841180645962743 |
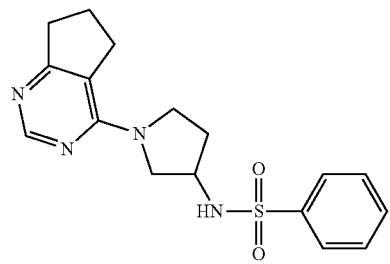
unknown chirality
| | |
|---|---|
| CatalogID | T636-1250 |
| Score | 0.9644615645907111 |
| Score_SNA RF | 0.8587018300764222 |
| Score_LAC TATE | 0.8982224440823987 |
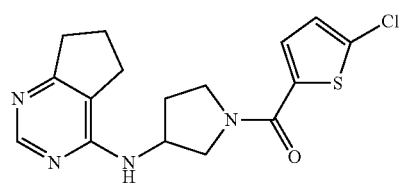
unknown chirality
| | |
|---|---|
| CatalogID | T636-2391 |
| Score | 0.932345345636482 |
| Score_SNA RF | 0.8743350166506818 |
| Score_LAC TATE | 0.8854443852559006 |
I4
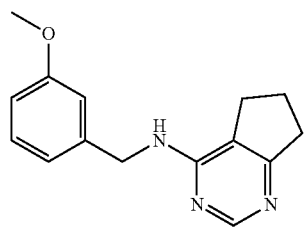 [SMILES: COc1cccc(CNc2ncnc3c2CCC3)c1]
| | |
|---|---|
| CatalogID | T636-0134 |
| Score | 0.7513378916885404 |
| Score_SNA | 0 |

Appendix I
| | |
|---|---|
| RF Score_LAC TATE | 0.3283315307869653 |
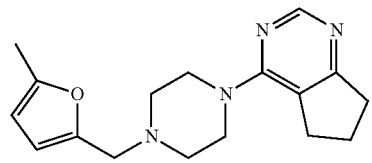 [SMILES: Cc1ccc(CN2CCN(c3ncnc4c3CCC4)CC2)o1]
I1
| | |
|---|---|
| CatalogID | T636-1937 |
| Score | 0.7395424373026418 |
| Score_SNA | 0.4729802324443744 |
| RF Score_LAC TATE | 0.8044660300257542 |
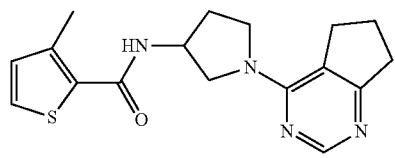
unknown chirality
I2
| | |
|---|---|
| CatalogID | T636-1114 |
| Score | 0.7253618680052571 |
| Score_SNA | 0.6238040062507072 |
| RF Score_LAC TATE | 0.547728388970824 |
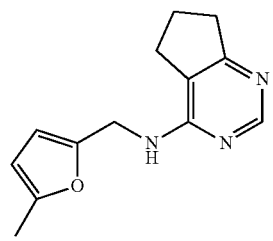 [SMILES: Cc1ccc(CNc2ncnc3c2CCC3)o1]
| | |
|---|---|
| CatalogID | T636-0054 |
| Score | 0.5530676837158811 |
| Score_SNA | 0 |
| RF Score_LAC TATE | 0 |
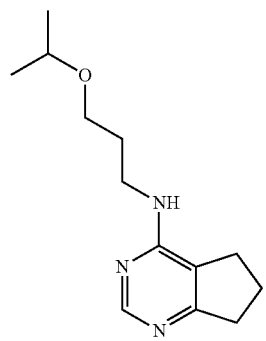 [SMILES: CC(C)OCCCNc1ncnc2c1CCC2]
| | |
|---|---|
| CatalogID | T636-0027 |
| Score | 0.5361875692026127 |
| Score_SNA | 0 |
| RF Score_LAC TATE | 0 |

-continued
Appendix I
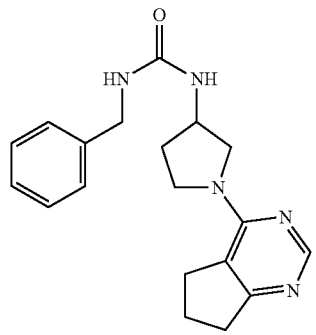
unknown chirality
| | | I5 |
|---|---|---|
| CatalogID | | T636-1210 |
| Score | | 0.48863237586667874 |
| Score_SNA | | 0.4304512346811785 |
| RF | | |
| Score_LAC | | 0.3226177294562539 |
| TATE | | |
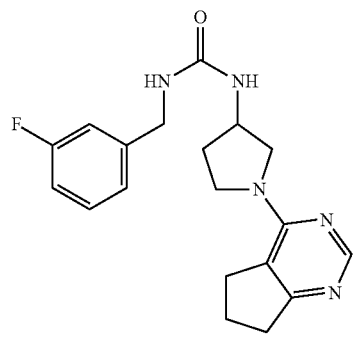
unknown chirality
| CatalogID | T636-1243 |
|---|---|
| Score | 0.45504840873980434 |
| Score_SNA | 0.417885043238299 |
| RF | |
| Score_LAC | 0 |
| TATE | |
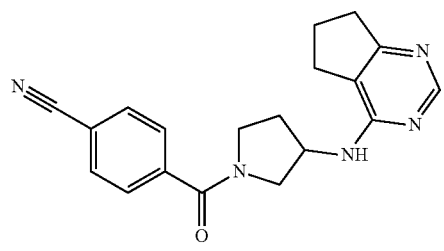
unknown chirality
| | | I3 |
|---|---|---|
| CatalogID | | T636-2387 |
| Score | | 0.4448438080296549 |
| Score_SNA | | 0.4808881204258762 |
| RF | | |
| Score_LAC | | 0.3005490442971268 |
| TATE | | |

Appendix I
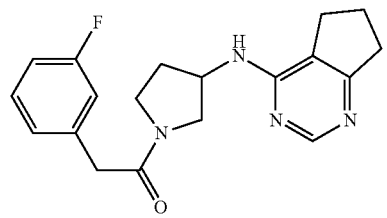
unknown chirality
| | |
|---|---|
| CatalogID | T636-2360 |
| Score | 0.4400292377018727 |
| Score_SNA RF | 0 |
| Score_LAC TATE | 0.41303393247609077 |
Family I (2/2)
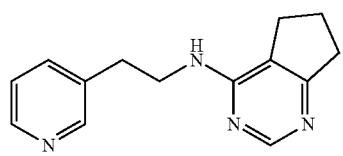 [SMILES: c1cncc(CCNc2ncnc3c2CCC3)c1]
| | |
|---|---|
| CatalogID | T636-0085 |
| Score | 0.28353821549062785 |
| Score_SNA RF | NOT_TESTED |
| Score_LAC TATE | NOT_TESTED |
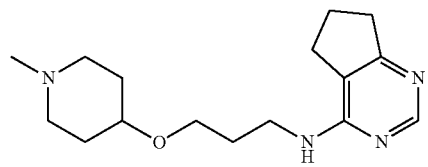 [SMILES: CN1CCC(OCCCNc2ncnc3c2CCC3)CC1]
| | |
|---|---|
| CatalogID | T636-0181 |
| Score | 0.22771221504714034 |
| Score_SNA RF | NOT_TESTED |
| Score_LAC TATE | NOT_TESTED |
I7
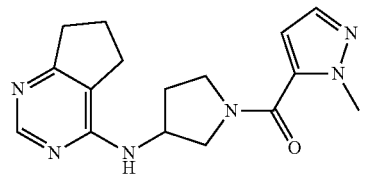 [SMILES: Cn1nccc1C(=O)N1CCC(Nc2ncnc3c2CCC3)C1]
| | |
|---|---|
| CatalogID | T636-2425 |
| Score | 0.21958972496943524 |
| Score_SNA RF | 0.27247555941127144 |
| Score_LAC TATE | 0.30269809289243466 |
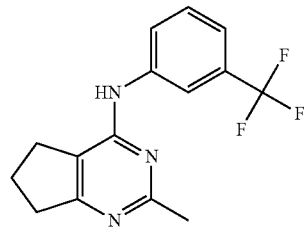 [SMILES: Cc1nc2c(c(Nc3cccc(C(F)(F)F)c3)n1)CCC2]

-continued

Appendix I

| | |
|---|---|
| CatalogID | D278-0514 |
| Score | 0 |
| Score_SNA RF | NOT_TESTED |
| Score_LAC TATE | NOT_TESTED |

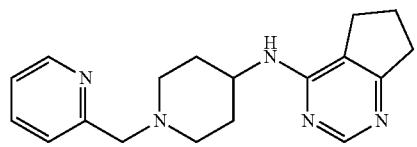 [SMILES: c1ccc(CN2CCC(Nc3ncnc4c3CCC4)CC2)nc1]

| | |
|---|---|
| CatalogID | T636-1715 |
| Score | 0 |
| Score_SNA RF | NOT_TESTED |
| Score_LAC TATE | NOT_TESTED |

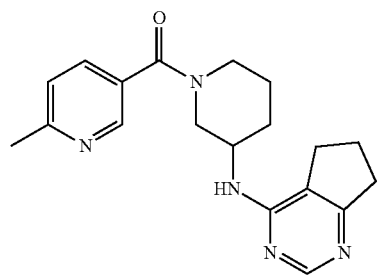

unknown chirality

| | |
|---|---|
| CatalogID | T636-2144 |
| Score | 0 |
| Score_SNA RF | NOT_TESTED |
| Score_LAC TATE | NOT_TESTED |

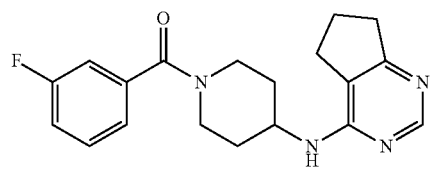 [SMILES: O=C(c1cccc(F)c1)N1CCC(Nc2ncnc3c2CCC3)CC1]

| | |
|---|---|
| CatalogID | T636-1601 |
| Score | 0 |
| Score_SNA RF | NOT_TESTED |
| Score_LAC TATE | NOT_TESTED |

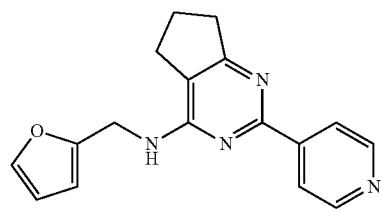 [SMILES: c1coc(CNc2nc(-c3ccncc3)nc3c2CCC3)c1]

| | |
|---|---|
| CatalogID | T636-0973 |
| Score | 0 |
| Score_SNA RF | NOT_TESTED |
| Score_LAC TATE | NOT_TESTED |

Appendix I
Family M
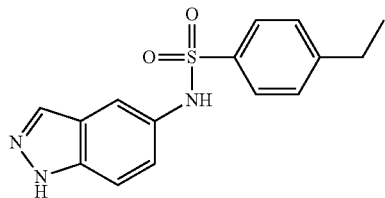 [SMILES: CCc1ccc(S(=O)(=O)Nc2ccc3[nH]ncc3c2)cc1]
M1
| | |
|---|---|
| CatalogID | T5599014 |
| Score | 0.5423680180991681 |
| Score_SNA RF | 0.5778347174521993 |
| Score_LAC TATE | 0.4418517946231513 |
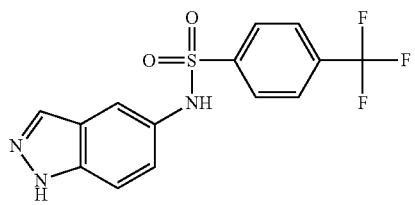 [SMILES: O=S(=O)(Nc1ccc2[nH]ncc2c1)c1ccc(C(F)(F)F)cc1]
M2
| | |
|---|---|
| CatalogID | T5653029 |
| Score | 0.36218450009714054 |
| Score_SNA RF | 0.5641600427647684 |
| Score_LAC TATE | 1.3535979987810212 |
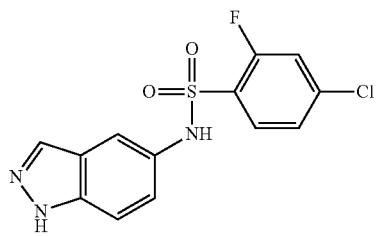 [SMILES: O=S(=O)(Nc1ccc2[nH]ncc2c1)c1ccc(Cl)cc1F]
| | |
|---|---|
| CatalogID | T5436375 |
| Score | 0 |
| Score_SNA RF | NOT_TESTED |
| Score_LAC TATE | NOT_TESTED |
Family N
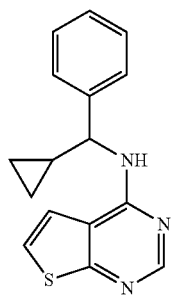
unknown chirality
| | |
|---|---|
| CatalogID | T6016487 |
| Score | 1.2641125532358868 |
| Score_SNA | 1.081418939812701 |

-continued
Appendix I
RF
Score_LAC 1.8565016432738268
TATE
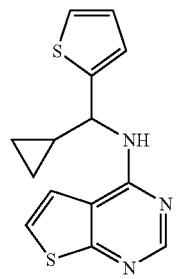
unknown chirality
CatalogID T5713637
Score 1.1408694959783288
Score_SNA 1.1838450634294277
RF
Score_LAC 1.287213975075479
TATE
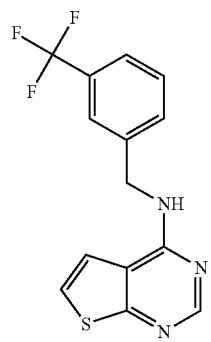 [SMILES: FC(F)(F)c1cccc(CNc2ncnc3sccc23)c1]
CatalogID T5346988
Score 0.9960475361592487
Score_SNA 0.9569371376034257
RF
Score_LAC 0.9326889609464317
TATE
N1
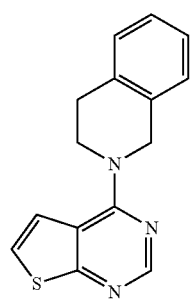 [SMILES: c1ccc2c(c1)CCN(c1ncnc3sccc13)C2]
CatalogID T0517-8250
Score 0.9574785194936402
Score_SNA 0.9123967008705844
RF
Score_LAC 0.9269003205038194
TATE

Appendix I -continued
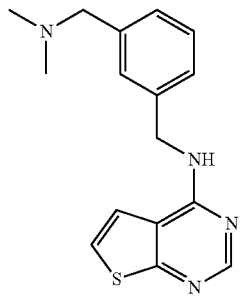 [SMILES: CN(C)Cc1cccc(CNc2ncnc3sccc23)c1]
| | |
|---|---|
| CatalogID | T6783542 |
| Score | 0.8569906585878225 |
| Score_SNA | 0.9183439213520057 |
| RF | |
| Score_LAC | 1.0325028610945488 |
| TATE | |
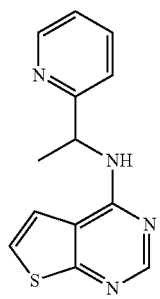
unknown chirality
N2
| | |
|---|---|
| CatalogID | T5672380 |
| Score | 0.7653019331178499 |
| Score_SNA | 0.7508314360875484 |
| RF | |
| Score_LAC | 0.5882588561328497 |
| TATE | |
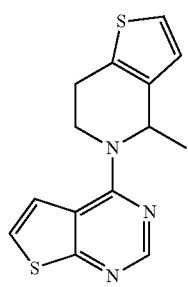
unknown chirality
N3
| | |
|---|---|
| CatalogID | T5630309 |
| Score | 0.7223424464359418 |
| Score_SNA | 0.48158494627623916 |
| RF | |
| Score_LAC | 0.6999954284930354 |
| TATE | |

Appendix I
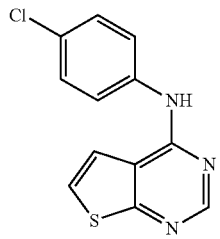 [SMILES: Clc1ccc(Nc2ncnc3sccc23)cc1]
| | |
|---|---|
| CatalogID | T5393195 |
| Score | 0.3693019544327658 |
| Score_SNA RF | NOT_TESTED |
| Score_LAC TATE | NOT_TESTED |
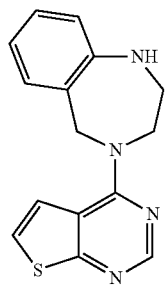 [SMILES: c1ccc2c(c1)CN(c1ncnc3sccc13)CCN2]
| | |
|---|---|
| CatalogID | T6768300 |
| Score | 0.34426794187571275 |
| Score_SNA RF | 0.3741744712882059 |
| Score_LAC TATE | 0 |
Family O
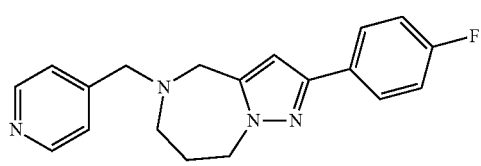 [SMILES: Fc1ccc(-c2cc3n(n2)CCCN(Cc2ccncc2)C3)cc1]
O1
| | |
|---|---|
| CatalogID | T202-1455 |
| Score | 0.9712680343150422 |
| Score_SNA RF | 0.7839449682790802 |
| Score_LAC TATE | 0.6933352118962879 |
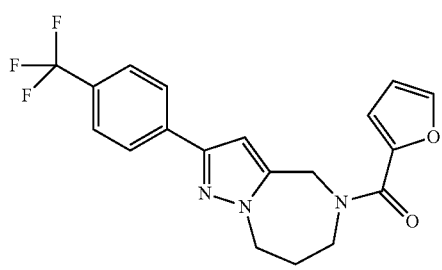 [SMILES: O=C(c1ccco1)N1CCCn2nc(-c3ccc(C(F)(F)F)cc3)cc2C1]
| | |
|---|---|
| CatalogID | T200-0370 |
| Score | 0.5618497687392737 |
| Score_SNA RF | 0.38039779657169775 |
| Score_LAC TATE | 0.2896301510809021 |

| Appendix I | |
|---|---|
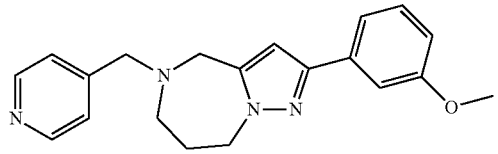 [SMILES: COc1cccc(-c2cc3n(n2)CCCN(Cc2ccncc2)C3)c1]
| | |
|---|---|
| CatalogID | T202-0973 |
| Score | 0.34101692441028175 |
| Score_SNA RF | 0.2834303332326549 |
| Score_LAC TATE | 0 |
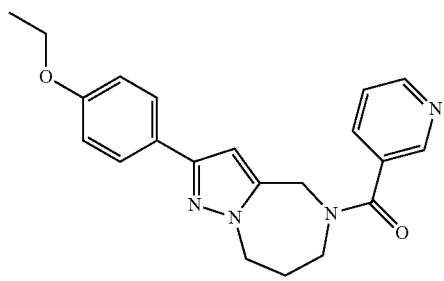 [SMILES: CCOc1ccc(-c2cc3n(n2)CCCN(C(=O)c2cccnc2)C3)cc1]
| | |
|---|---|
| CatalogID | T200-0707 |
| Score | 0.16740550045889108 |
| Score_SNA RF | NOT_TESTED |
| Score_LAC TATE | NOT_TESTED |
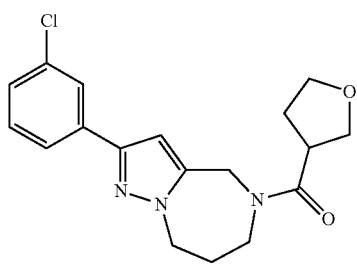
unknown chirality
| | |
|---|---|
| CatalogID | P218-0884 |
| Score | 0 |
| Score_SNA RF | NOT_TESTED |
| Score_LAC TATE | NOT_TESTED |
| Family P | |
|---|---|
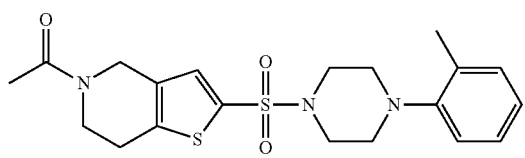 [SMILES: CC(=O)N1CCc2sc(S(=O)(=O)N3CCN(c4ccccc4C)CC3)cc2C1]
P1
| | |
|---|---|
| CatalogID | P025-0159 |
| Score | 0.9534567194540251 |
| Score_SNA RF | 0.8006744658424207 |
| Score_LAC TATE | 0.9231665502291709 |

-continued
Appendix I
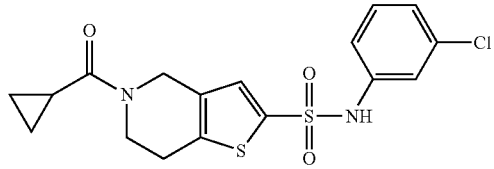 [SMILES: O=C(C1CC1)N1CCc2sc(S(=O)(=O)Nc3cccc(Cl)c3)cc2C1]
| | |
|---|---|
| CatalogID | P025-0462 |
| Score | 0.3872119888600468 |
| Score_SNA RF | NOT_TESTED |
| Score_LAC TATE | NOT_TESTED |
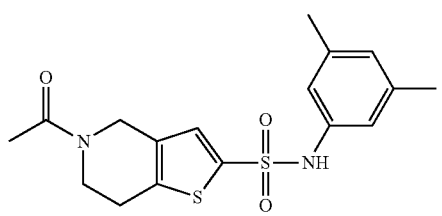 [SMILES: CC(=O)N1CCc2sc(S(=O)(=O)Nc3cc(C)cc(C)c3)cc2C1]
| | |
|---|---|
| CatalogID | P025-0080 |
| Score | 0.33093523462251484 |
| Score_SNA RF | NOT_TESTED |
| Score_LAC TATE | NOT_TESTED |
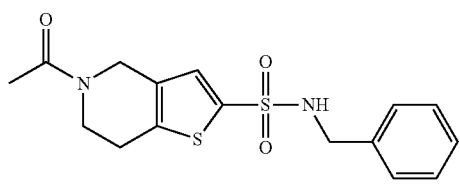 [SMILES: CC(=O)N1CCc2sc(S(=O)(=O)NCc3ccccc3)cc2C1]
| | |
|---|---|
| CatalogID | P025-0168 |
| Score | 0.14492617861885423 |
| Score_SNA RF | NOT_TESTED |
| Score_LAC TATE | NOT_TESTED |
Family Q
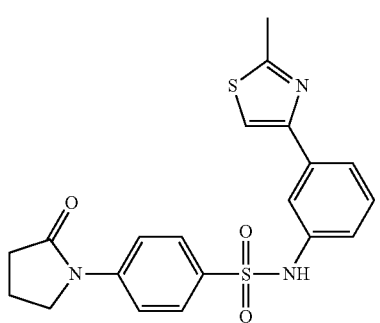 [SMILES: Cc1nc(-c2cccc(NS(=O)(=O)c3ccc(N4CCCC4=O)cc3)c2)cs1]
Q2
| | |
|---|---|
| CatalogID | T5599698 |
| Score | 0.855937067832691 |
| Score_SNA RF | 0.8856396558188464 |
| Score_LAC TATE | 0.7495521570358064 |

Appendix I
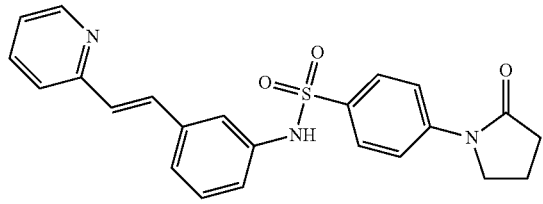 [SMILES: O=C1CCCN1c1ccc(S(=O)(=O)Nc2cccc(/C=C/c3ccccn3)c2)cc1]
Q1
| CatalogID | T5644989 |
|---|---|
| Score | 0.6796130774342963 |
| Score_SNA | 0.8385482212594828 |
| RF | |
| Score_LAC | 0.7858882841885826 |
| TATE | |
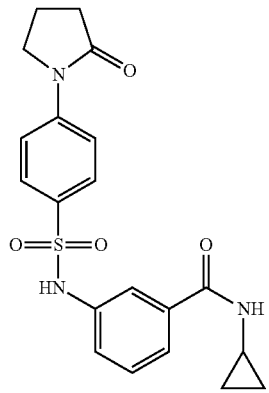 [SMILES: O=C(NC1CC1)c1cccc(NS(=O)(=O)c2ccc(N3CCCC3=O)cc2)c1]
Q3
| CatalogID | T5618591 |
|---|---|
| Score | 0.41563542866343284 |
| Score_SNA | 0.5352874527303951 |
| RF | |
| Score_LAC | 0.3601184130676996 |
| TATE | |
Family R
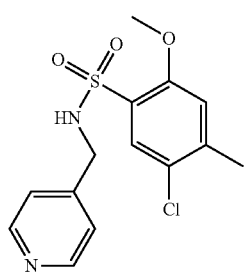 [SMILES: COc1cc(C)c(Cl)cc1S(=O)(=O)NCc1ccncc1]
R1
| CatalogID | T5580243 |
|---|---|
| Score | 0.8528253990291386 |
| Score_SNA | 0.8564967067233966 |
| RF | |
| Score_LAC | 0.7229025303296649 |
| TATE | |

-continued
Appendix I
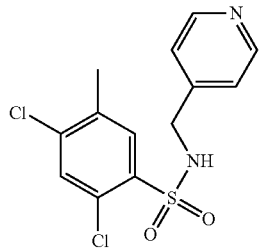 [SMILES: Cc1cc(S(=O)(=O)NCc2ccncc2)c(Cl)cc1Cl]
| | |
|---|---|
| CatalogID | T5581430 |
| Score | 0.4721766063471703 |
| Score_SNA | 0.5050374641230523 |
| RF | |
| Score_LAC | 0 |
| TATE | |
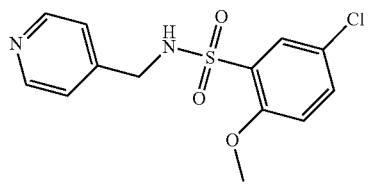 [SMILES: COc1ccc(Cl)cc1S(=O)(=O)NCc1ccncc1]
| | |
|---|---|
| CatalogID | F0376-0203 |
| Score | 0.20288513101448935 |
| Score_SNA | 0 |
| RF | |
| Score_LAC | 0 |
| TATE | |
Family S
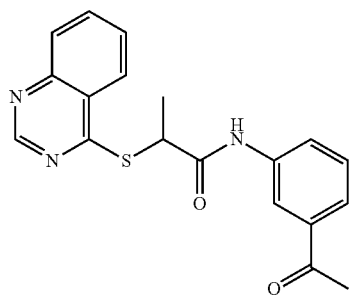
S1
unknown chirality
| | |
|---|---|
| CatalogID | T0511-9200 |
| Score | 0.8441832214748136 |
| Score_SNA | 0.48656473560837266 |
| RF | |
| Score_LAC | 0.7517887234187022 |
| TATE | |

| Appendix I |  |
|---|---|
| 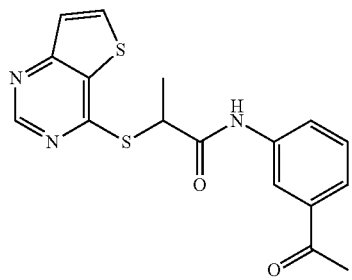<br>unknown chirality | S2 |
| CatalogID | T5627721 |
| Score | 0.7237159041769383 |
| Score_SNA | 0.7384840988075632 |
| RF | |
| Score_LAC | 0.9486502359872533 |
| TATE | |
| Family T | |
| 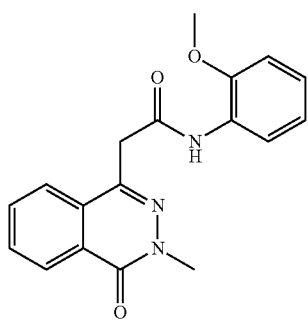 [SMILES: COc1ccccc1NC(=O)Cc1nn(C)c(=O)c2ccccc12] | T1 |
| CatalogID | K851-0113 |
| Score | 0.722280122898277 |
| Score_SNA | 0.7568885849430411 |
| RF | |
| Score_LAC | 0.9280741657657858 |
| TATE | |
| 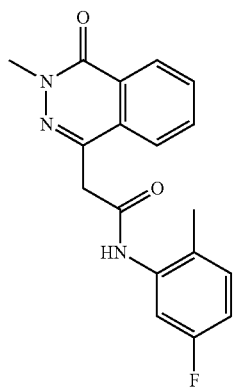 [SMILES: Cc1ccc(F)cc1NC(=O)Cc1nn(C)c(=O)c2ccccc12] | |
| CatalogID | T6302989 |
| Score | 0.4051145241844445 |
| Score_SNA | 0.407229804897944 |
| RF | |
| Score_LAC | 0 |
| TATE | |

Appendix I
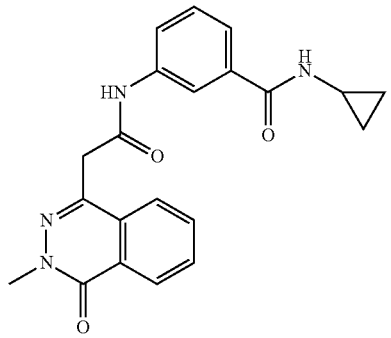 [SMILES: Cn1nc(CC(=O)Nc2cccc(C(=O)NC3CC3)c2)c2ccccc2c1=O]
| | |
|---|---|
| CatalogID | T5543110 |
| Score | 0.39099380629992164 |
| Score_SNA RF | NOT_TESTED |
| Score_LAC TATE | NOT_TESTED |
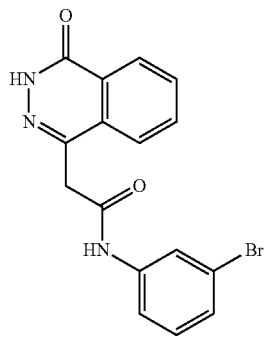 [SMILES: O=C(Cc1n[nH]c(=O)c2ccccc12)Nc1cccc(Br)c1]
| | |
|---|---|
| CatalogID | T5717474 |
| Score | 0.217305964318331 |
| Score_SNA RF | NOT_TESTED |
| Score_LAC TATE | NOT_TESTED |
Family U
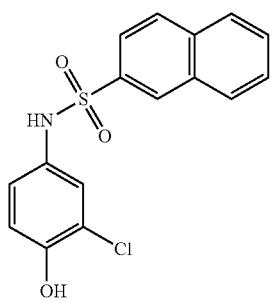 [SMILES: O=S(=O)(Nc1ccc(O)c(Cl)c1)c1ccc2ccccc2c1]
| | |
|---|---|
| CatalogID | T0517-8939 |
| Score | 0.7679530086775413 |
| Score_SNA RF | 0.6381895919510732 |
| Score_LAC TATE | 0 |

-continued
Appendix I
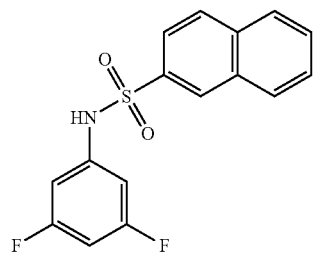 [SMILES: O=S(=O)(Nc1cc(F)cc(F)c1)c1ccc2ccccc2c1]
U1
| | |
|---|---|
| CatalogID | T5884038 |
| Score | 0.7207565908025609 |
| Score_SNA | 0.8379087709023765 |
| RF | |
| Score_LAC | 0.9262350987060564 |
| TATE | |
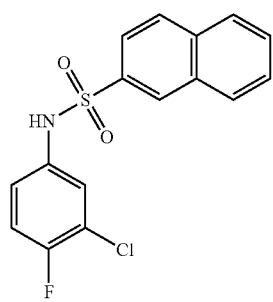 [SMILES: O=S(=O)(Nc1ccc(F)c(Cl)c1)c1ccc2ccccc2c1]
U2
| | |
|---|---|
| CatalogID | T5231424 |
| Score | 0.6726954141746788 |
| Score_SNA | 0.3706614739849921 |
| RF | |
| Score_LAC | 0.5258096899997711 |
| TATE | |
Family V
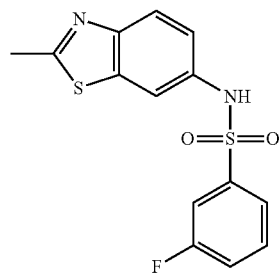 [SMILES: Cc1nc2ccc(NS(=O)(=O)c3cccc(F)c3)cc2s1]
V1
| | |
|---|---|
| CatalogID | T6937001 |
| Score | 0.8093547207837104 |
| Score_SNA | 0.855659897786533 |
| RF | |
| Score_LAC | 0.9087796548938434 |
| TATE | |

Appendix I
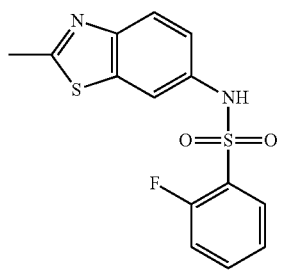 [SMILES: Cc1nc2ccc(NS(=O)(=O)c3ccccc3F)cc2s1]
V2
| | |
|---|---|
| CatalogID | T5511047 |
| Score | 0.6704889582104439 |
| Score_SNA RF | 0.5544595058134321 |
| Score_LAC TATE | 0.3824503515573746 |
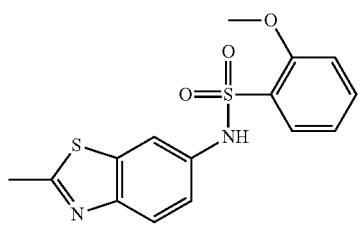 [SMILES: COc1ccccc1S(=O)(=O)Nc1ccc2nc(C)sc2c1]
| | |
|---|---|
| CatalogID | T5246417 |
| Score | 0.2408425006175835 |
| Score_SNA RF | 0.24545703685650536 |
| Score_LAC TATE | 0 |
Family W
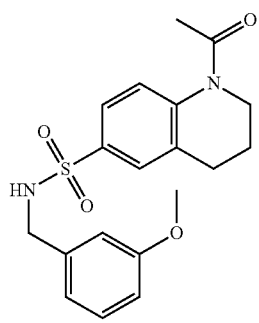 [SMILES: COc1cccc(CNS(=O)(=O)c2ccc3c(c2)CCCN3C(C)=O)c1]
W1
| | |
|---|---|
| CatalogID | T5967389 |
| Score | 0.7899374946109983 |
| Score_SNA RF | 0.2788913341775572 |
| Score_LAC TATE | 0.45168048543941974 |
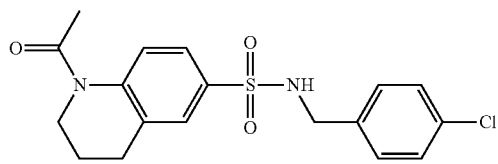 [SMILES: CC(=O)N1CCCc2cc(S(=O)(=O)NCc3ccc(Cl)cc3)ccc21]
| | |
|---|---|
| CatalogID | G855-0033 |
| Score | 0.34741470465778507 |
| Score_SNA RF | NOT_TESTED |
| Score_LAC TATE | NOT_TESTED |

-continued
Appendix I
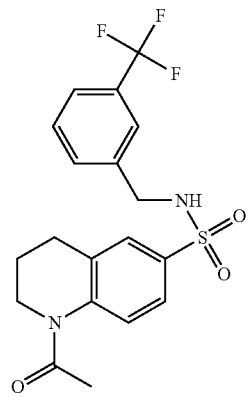 [SMILES: CC(=O)N1CCCc2cc(S(=O)(=O)NCc3cccc(C(F)(F)F)c3)ccc21]
| | |
|---|---|
| CatalogID | T6099519 |
| Score | 0.2755618623360358 |
| Score_SNA | 0.39438626320595177 |
| RF | |
| Score_LAC | 0 |
| TATE | |
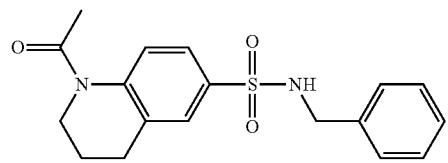 [SMILES: CC(=O)N1CCCc2cc(S(=O)(=O)NCc3ccccc3)ccc21]
| | |
|---|---|
| CatalogID | G855-0210 |
| Score | 0.20620606338380704 |
| Score_SNA | 0.31231048770176095 |
| RF | |
| Score_LAC | 0 |
| TATE | |
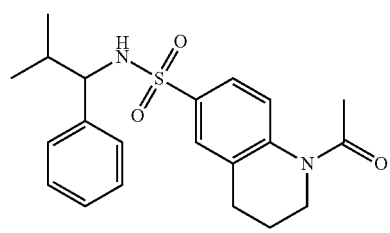 [SMILES: CC(=O)N1CCCc2cc(S(=O)(=O)NC(c3ccccc3)C(C)C)ccc21]
| | |
|---|---|
| CatalogID | T6067366 |
| Score | 0 |
| Score_SNA | NOT_TESTED |
| RF | |
| Score_LAC | NOT_TESTED |
| TATE | |

Appendix I
Family Y
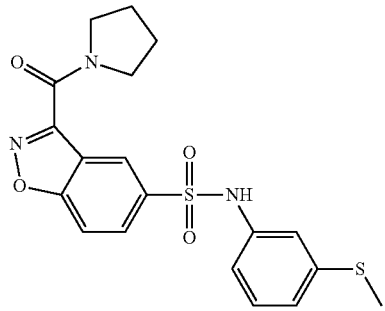 [SMILES: CSc1cccc(NS(=O)(=O)c2ccc3onc(C(=O)N4CCCC4)c3c2)c1]
Y1
| | |
|---|---|
| CatalogID | L995-0125 |
| Score | 0.8544527003879917 |
| Score_SNA RF | 0.8016477664825784 |
| Score_LAC TATE | 0.9122179865041484 |
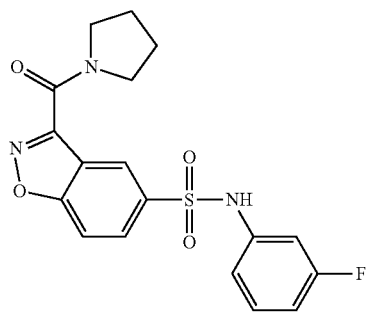 [SMILES: O=C(c1noc2ccc(S(=O)(=O)Nc3cccc(F)c3)cc12)N1CCCC1]
Y2
| | |
|---|---|
| CatalogID | L995-0058 |
| Score | 0.42257261140984437 |
| Score_SNA RF | 0.4197252825194825 |
| Score_LAC TATE | 0.4240067586981341 |
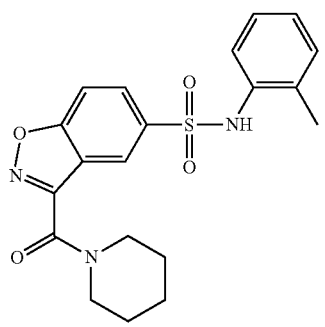 [SMILES: Cc1ccccc1NS(=O)(=O)c1ccc2onc(C(=O)N3CCCCC3)c2c1]
| | |
|---|---|
| CatalogID | L995-0405 |
| Score | 0.21346259969461018 |
| Score_SNA RF | 0.3723794417974404 |
| Score_LAC TATE | 0 |

Appendix I
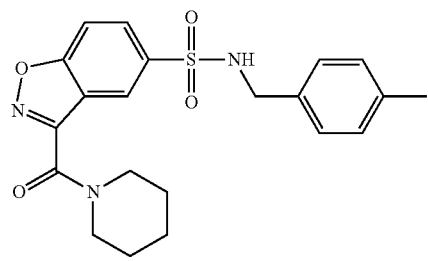 [SMILES: Cc1ccc(CNS(=O)(=O)c2ccc3onc(C(=O)N4CCCCC4)c3c2)cc1]
| | |
|---|---|
| CatalogID | L995-0386 |
| Score | 0.18817082101410132 |
| Score_SNA RF | NOT_TESTED |
| Score_LAC TATE | NOT_TESTED |
Appendix II
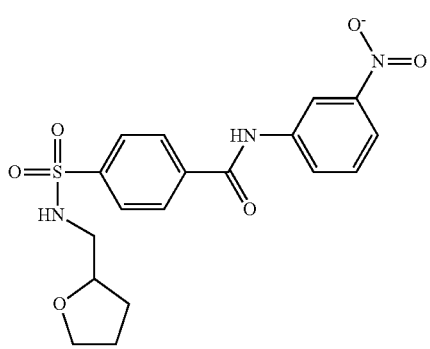
unknown chirality
| | |
|---|---|
| Catalog ID | T6010789 |
| Score Lact. | 1.31 |
| EC50 | 5.82 |
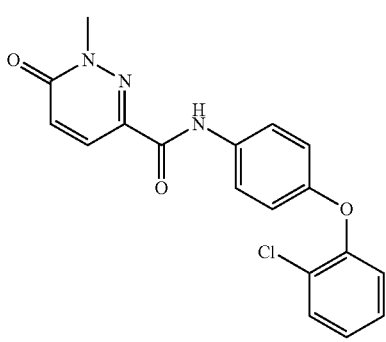 [SMILES: Cn1nc(C(=O)Nc2ccc(Oc3ccccc3Cl)cc2)ccc1=O]
| | |
|---|---|
| Catalog ID | T5813085 |
| Score Lact. | 1.01 |
| EC50 | 4.10 |
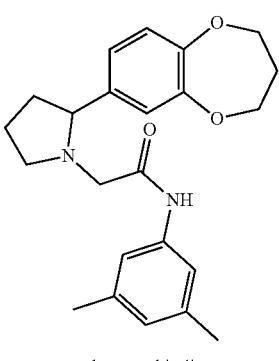
unknown chirality
| | |
|---|---|
| Catalog ID | T5993799 |
| Score Lact. | 1.14 |
| EC50 | 8.81 |
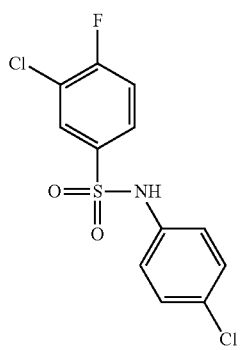 [SMILES: O=S(=O)(Nc1ccc(Cl)cc1)c1ccc(F)c(Cl)c1]
| | |
|---|---|
| Catalog ID | T6947848 |
| Score Lact. | 0.98 |
| EC50 | 5.50 |

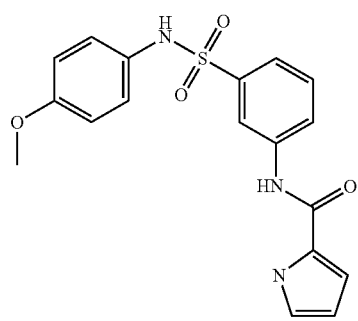 [SMILES: COc1ccc(NS(=O)(=O)c2cccc(NC(=O)c3ccc[nH]3)c2)cc1]
| Catalog ID | T0517-4117 |
|---|---|
| Score Lact. | 0.91 |
| EC50 | 5.43 |
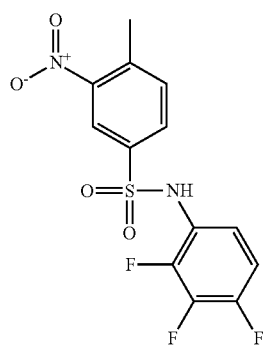 [SMILES: Cc1ccc(S(=O)(=O)Nc2ccc(F)c(F)c2F)cc1[N+](=O)[O-]]
| Catalog ID | T5729557 |
|---|---|
| Score Lact. | 0.88 |
| EC50 | 5.69 |
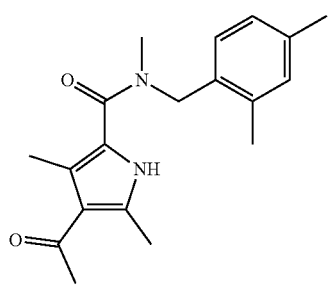 [SMILES: CC(=O)c1c(C)[nH]c(C(=O)N(C)Cc2ccc(C)cc2C)c1C]
| Catalog ID | T5705522 |
|---|---|
| Score Lact. | 0.85 |
| EC50 | 2.53 |
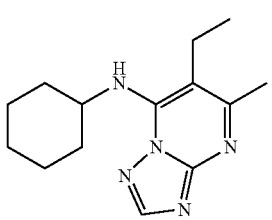 [SMILES: CCc1c(C)nc2ncnn2c1NC1CCCCC1]
| Catalog ID | Z606-8352 |
|---|---|
| Score Lact. | 0.83 |
| EC50 | 4.11 |
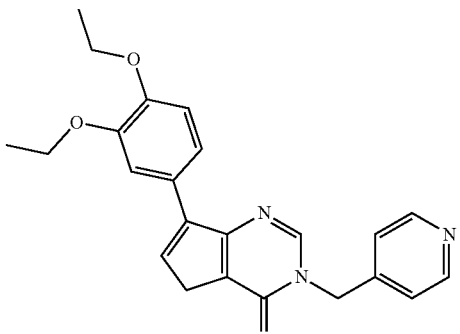
| Catalog ID | L115-0403 |
|---|---|
| Score Lact. | 0.81 |
| EC50 | 3.28 |
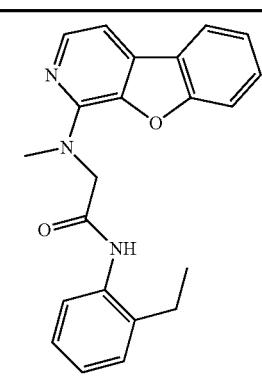
| Catalog ID | T5712071 |
|---|---|
| Score Lact. | 0.8 |
| EC50 | 1.14 |
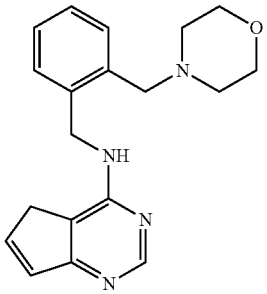 [SMILES: C1=Cc2ncnc(NCc3ccccc3CN3CCOCC3)c2C1]
| Catalog ID | T5790476 |
|---|---|
| Score Lact. | 0.79 |
| EC50 | 3.98 |
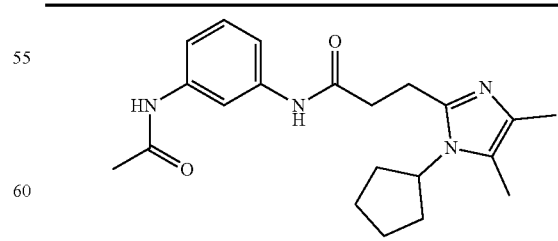
| Catalog ID | T5788339 |
|---|---|
| Score Lact. | 0.75 |
| EC50 | 3.9 |

-continued
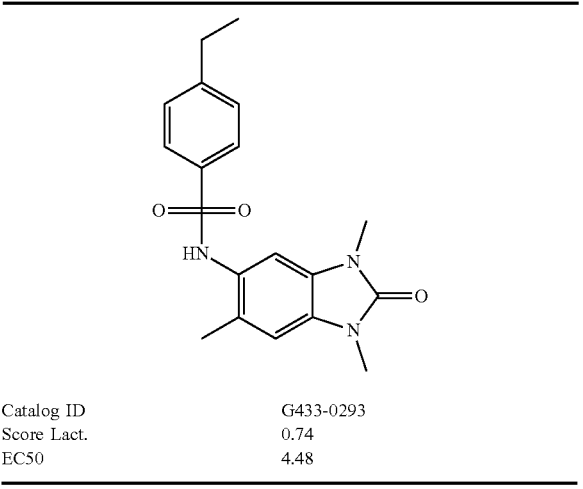
| Catalog ID | G433-0293 |
|---|---|
| Score Lact. | 0.74 |
| EC50 | 4.48 |
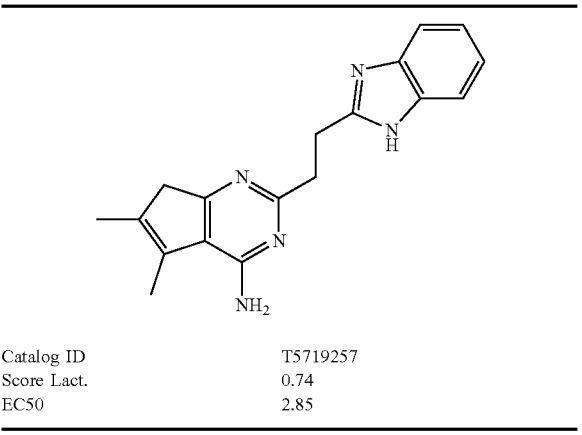
| Catalog ID | T5719257 |
|---|---|
| Score Lact. | 0.74 |
| EC50 | 2.85 |
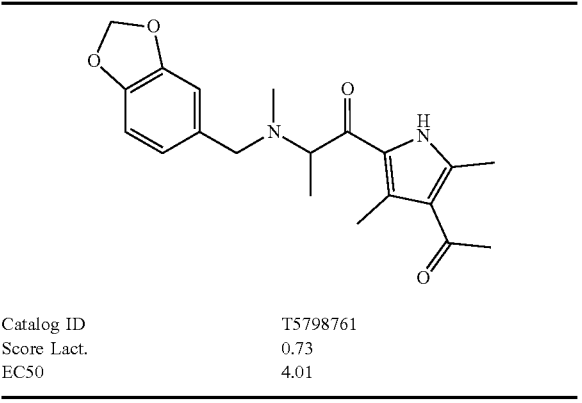
| Catalog ID | T5798761 |
|---|---|
| Score Lact. | 0.73 |
| EC50 | 4.01 |
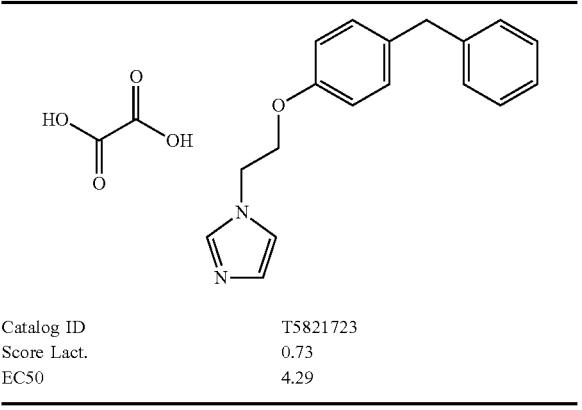
| Catalog ID | T5821723 |
|---|---|
| Score Lact. | 0.73 |
| EC50 | 4.29 |
-continued
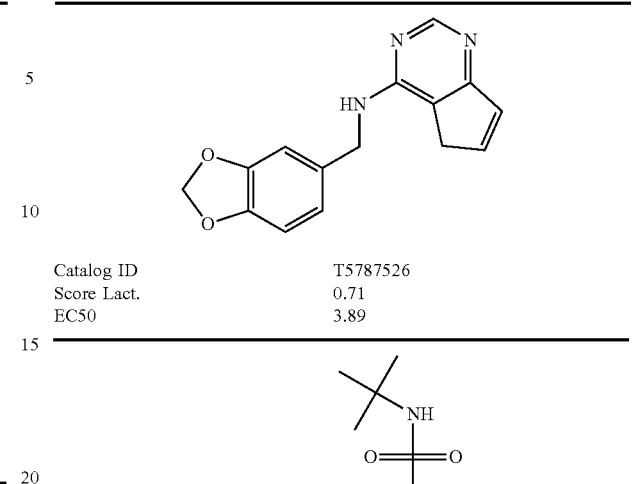
| Catalog ID | T5787526 |
|---|---|
| Score Lact. | 0.71 |
| EC50 | 3.89 |
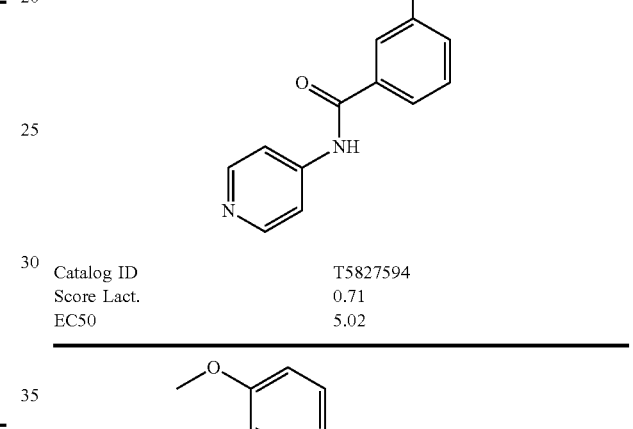
| Catalog ID | T5827594 |
|---|---|
| Score Lact. | 0.71 |
| EC50 | 5.02 |
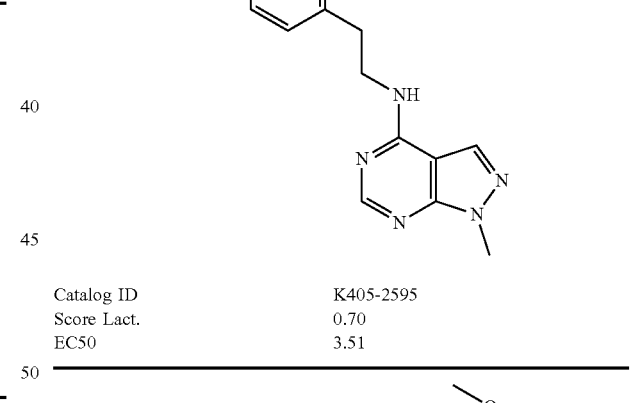
| Catalog ID | K405-2595 |
|---|---|
| Score Lact. | 0.70 |
| EC50 | 3.51 |
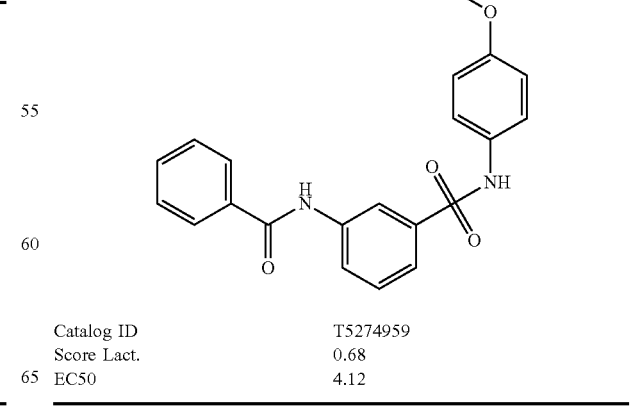
| Catalog ID | T5274959 |
|---|---|
| Score Lact. | 0.68 |
| EC50 | 4.12 |

-continued
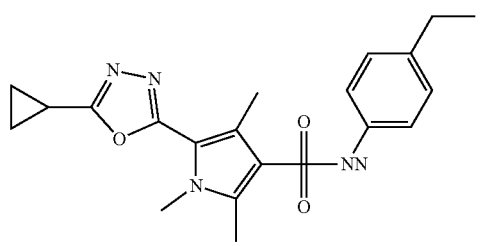
| | |
|---|---|
| Catalog ID | M950-1515 |
| Score Lact. | 0.657 |
| EC50 | 4.06 |
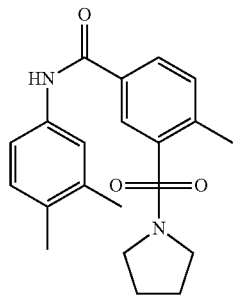
| | |
|---|---|
| Catalog ID | T5450239 |
| Score Lact. | 0.67 |
| EC50 | 4.42 |
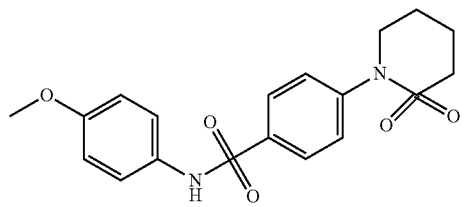
| | |
|---|---|
| Catalog ID | G508-0015 |
| Score Lact. | 0.67 |
| EC50 | 4.83 |
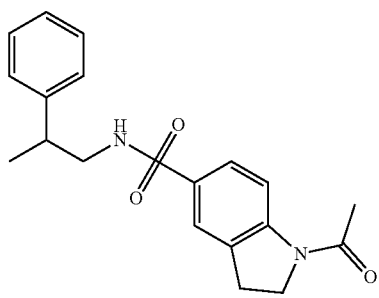
| | |
|---|---|
| Catalog ID | T5707230 |
| Score Lact. | 0.67 |
| EC50 | 4.88 |
-continued
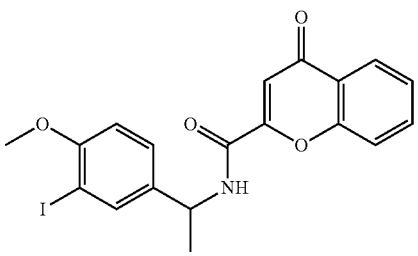 [SMILES: COc1ccc(C(C)NC(=O)c2cc(=O)c3ccccc3o2)cc1I]
| | |
|---|---|
| Catalog ID | T5710343 |
| Score Lact. | 0.67 |
| EC50 | 6.31 |
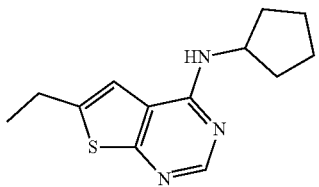 [SMILES: CCc1cc2c(NC3CCCC3)ncnc2s1]
| | |
|---|---|
| Catalog ID | 887-0183 |
| Score Lact. | 0.66 |
| EC50 | 3.94 |
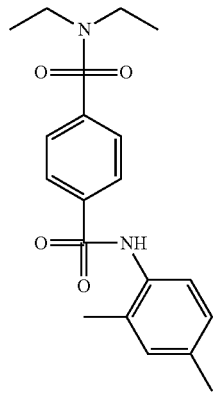
| | |
|---|---|
| Catalog ID | T5453923 |
| Score Lact. | 0.66 |
| EC50 | 5.36 |
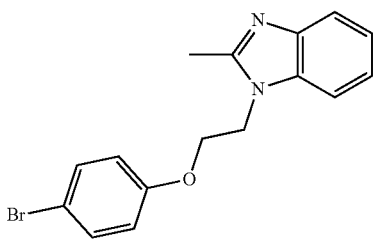 [SMILES: Cc1nc2ccccc2n1CCOc1ccc(Br)cc1]
| | |
|---|---|
| Catalog ID | T0505-4087 |
| Score Lact. | 0.64 |
| EC50 | 7.07 |

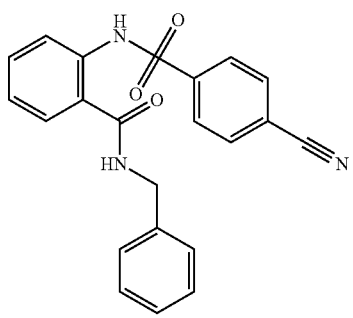
| | |
|---|---|
| Catalog ID | T5673322 |
| Score Lact. | 0.63 |
| EC50 | 7.42 |
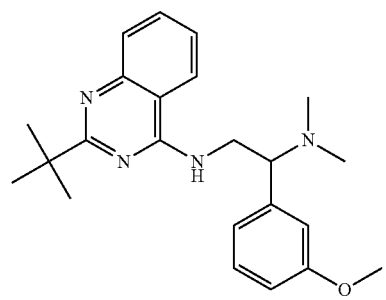 [SMILES: COc1cccc(C(CNc2nc(C(C)(C)C)nc3ccccc23)N(C)C)c1]
| | |
|---|---|
| Catalog ID | T5800607 |
| Score Lact. | 063 |
| EC50 | 5.87 |
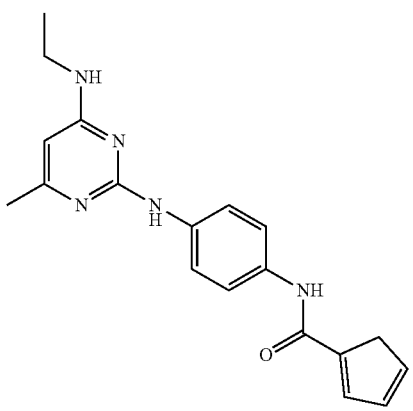 [SMILES: CCNc1cc(C)nc(Nc2ccc(NC(=O)C3=CC=CC3)cc2)n1]
| | |
|---|---|
| Catalog ID | G869-0071 |
| Score Lact. | 0.63 |
| EC50 | 4.9 |
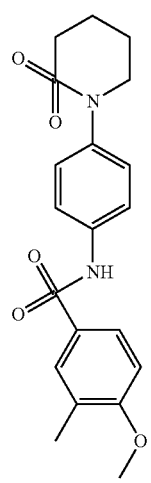
| | |
|---|---|
| Catalog ID | F2794-0128 |
| Score Lact. | 0.62 |
| EC50 | 9.85 |
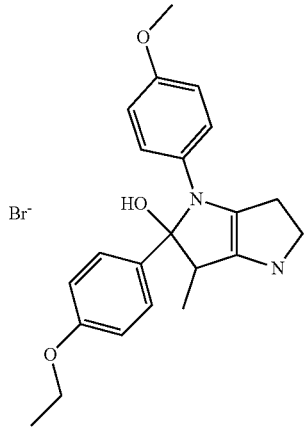 [SMILES: [Br-] ; CCOc1ccc(C2(O)C(C)C3=C(CCN3)N2c2ccc(OC)cc2)cc1]
| | |
|---|---|
| Catalog ID | T0500-6629 |
| Score Lact. | 0.61 |
| EC50 | 2.61 |
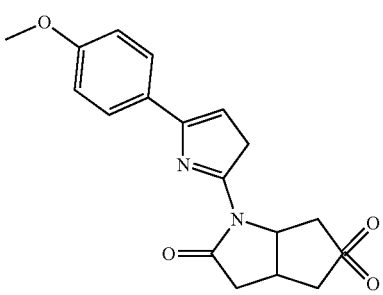
| | |
|---|---|
| Catalog ID | T5832764 |
| Score Lact. | 0.60 |
| EC50 | 4.02 |

-continued
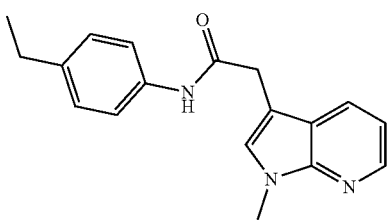 [SMILES: CCc1ccc(NC(=O)Cc2cn(C)c3ncccc23)cc1]
| Catalog ID | M508-0370 |
|---|---|
| Score Lact. | 0.60 |
| EC50 | 4.58 |
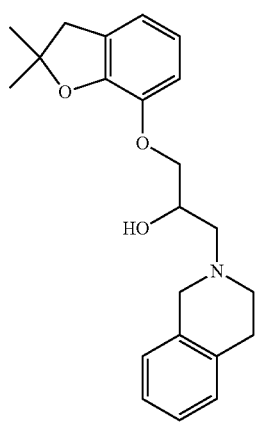 [SMILES: CC1(C)Cc2cccc(OCC(O)CN3CCc4ccccc4C3)c2O1]
| Catalog ID | T0515-1783 |
|---|---|
| Score Lact. | 0.59 |
| EC50 | 5.39 |
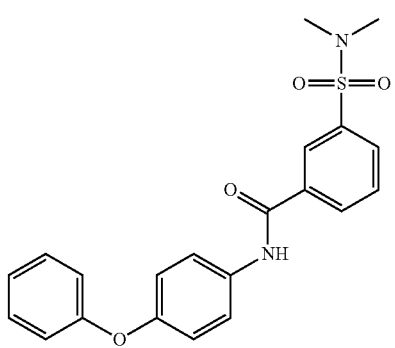 [SMILES: CN(C)S(=O)(=O)c1cccc(C(=O)Nc2ccc(Oc3ccccc3)cc2)c1]
| Catalog ID | T5393500 |
|---|---|
| Score Lact. | 0.59 |
| EC50 | 3.43 |
-continued
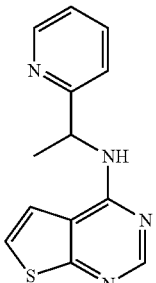
unknown chirality
| Catalog ID | T5672380 |
|---|---|
| Score Lact. | 0.58 |
| EC50 | 3.91 |
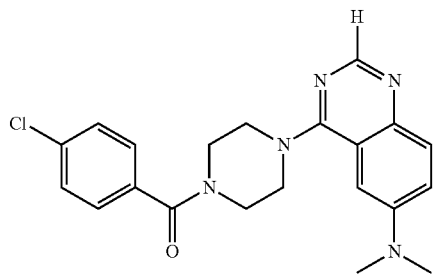 [SMILES: CN(C)c1ccc2ncnc(N3CCN(C(=O)c4ccc(Cl)cc4)CC3)c2c1]
| Catalog ID | M381-0730 |
|---|---|
| Score Lact. | 0.57 |
| EC50 | 3.19 |
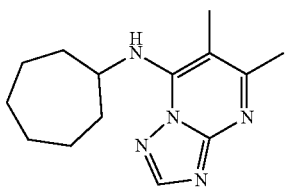 [SMILES: Cc1nc2ncnn2c(NC2CCCCCC2)c1C]
| Catalog ID | Z606-8287 |
|---|---|
| Score Lact. | 0.57 |
| EC50 | 4.29 |
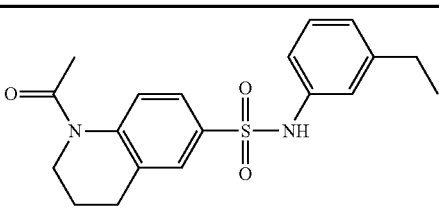
| Catalog ID | G855-0143 |
|---|---|
| Score Lact. | 0.56 |
| EC50 | 4.72 |
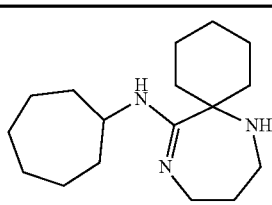
| Catalog ID | Z076-0028 |
|---|---|
| Score Lact. | 0.56 |
| EC50 | 8.01 |

-continued
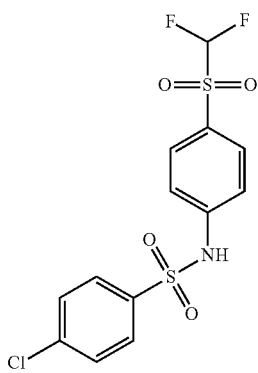 [SMILES: O=S(=O)(Nc1ccc(S(=O)(=O)C(F)F)cc1)c1ccc(Cl)cc1]
| Catalog ID | T5311200 |
|---|---|
| Score Lact. | 0.56 |
| EC50 | 6.02 |
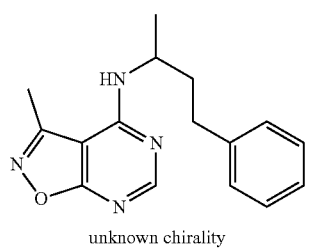 [SMILES: Cc1noc2ncnc(NC(C)CCc3ccccc3)c12]
unknown chirality
| Catalog ID | E944-0182 |
|---|---|
| Score Lact. | 0.55 |
| EC50 | 3.99 |
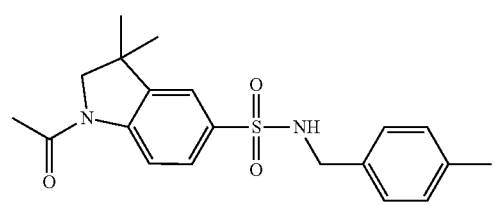 [SMILES: CC(=O)N1CC(C)(C)c2cc(S(=O)(=O)NCc3ccc(C)cc3)ccc21]
| Catalog ID | L302-0069 |
|---|---|
| Score Lact. | 0.55 |
| EC50 | 6.27 |
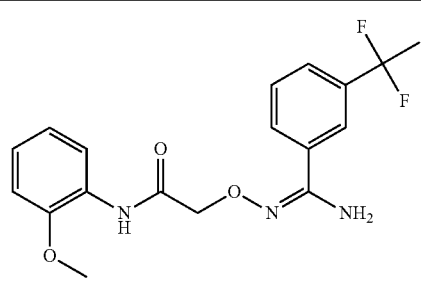
| Catalog ID | T5770640 |
|---|---|
| Score Lact. | 0.55 |
| EC50 | 4.86 |
-continued
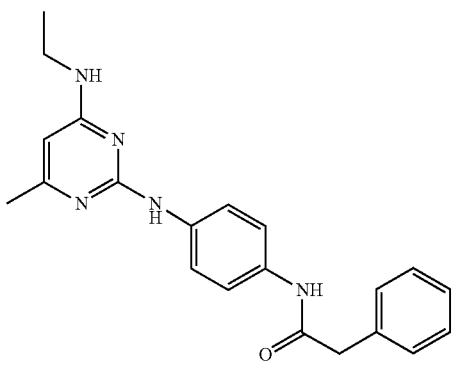 [SMILES: CCNc1cc(C)nc(Nc2ccc(NC(=O)Cc3ccccc3)cc2)n1]
| Catalog ID | G869-0064 |
|---|---|
| Score Lact. | 0.54 |
| EC50 | 4.26 |
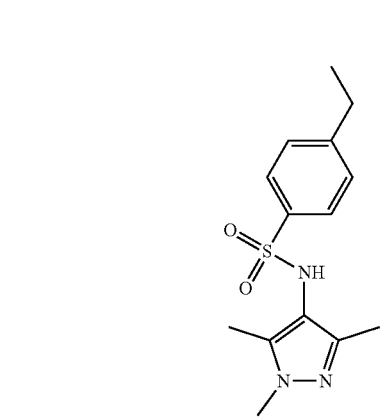
| Catalog ID | T5753165 |
|---|---|
| Score Lact. | 0.54 |
| EC50 | 6.41 |
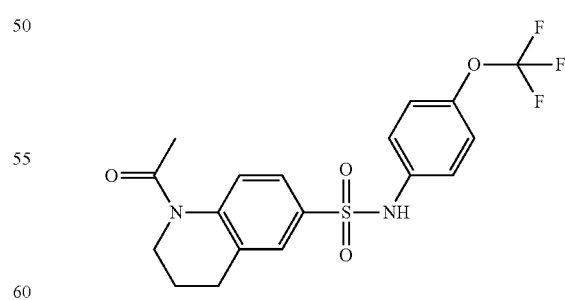
| Catalog ID | G855-0183 |
|---|---|
| Score Lact. | 0.54 |
| EC50 | 6.0 |

-continued
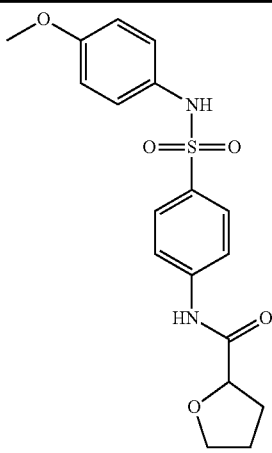
unknown chirality
| Catalog ID | T5329723 |
|---|---|
| Score Lact. | 0.53 |
| EC50 | 4.61 |
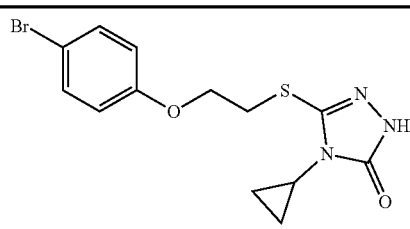
| Catalog ID | T533260 |
|---|---|
| Score Lact. | 0.53 |
| EC50 | 6.84 |
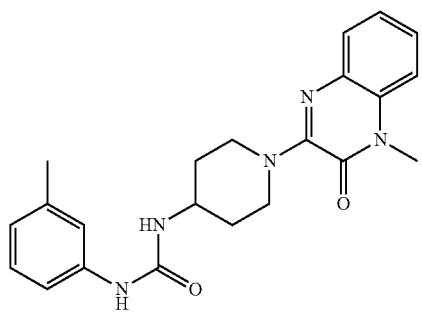 [SMILES: Cc1cccc(NC(=O)NC2CCN(c3nc4ccccc4n(C)c3=O)CC2)c1]
| Catalog ID | L932-0267 |
|---|---|
| Score Lact. | 0.53 |
| EC50 | 4.64 |
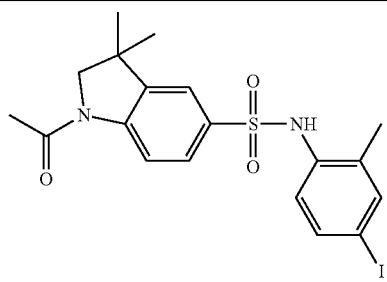
| Catalog ID | L302-0181 |
|---|---|
| Score Lact. | 0.52 |
| EC50 | 5.05 |
-continued
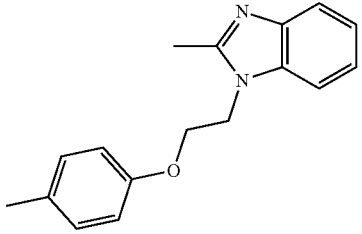 [SMILES: Cc1ccc(OCCn2c(C)nc3ccccc32)cc1]
| Catalog ID | T5444083 |
|---|---|
| Score Lact. | 0.51 |
| EC50 | 4.59 |
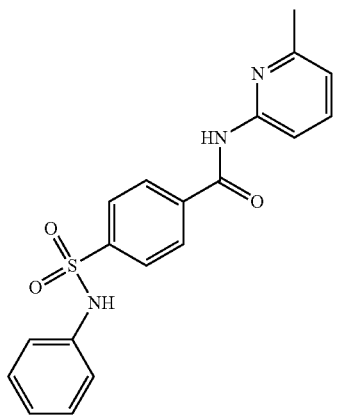 [SMILES: Cc1cccc(NC(=O)c2ccc(S(=O)(=O)Nc3ccccc3)cc2)n1]
| Catalog ID | T6125251 |
|---|---|
| Score Lact. | 0.51 |
| EC50 | 4.56 |
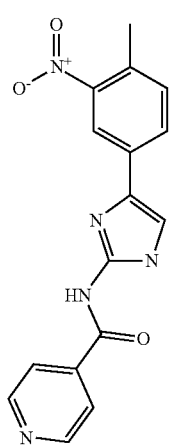 [SMILES: Cc1ccc(-c2c[nH]c(NC(=O)c3ccncc3)n2)cc1[N+](=O)[O-]]
| Catalog ID | T5694329 |
|---|---|
| Score Lact. | 0.47 |
| EC50 | 1.59 |

-continued
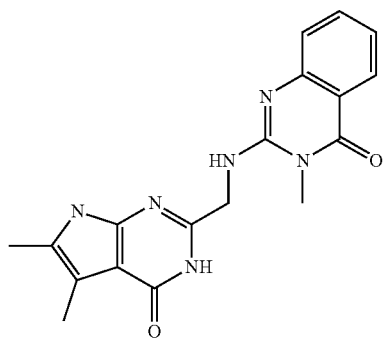 [SMILES: Cc1[nH]c2nc(CNc3nc4ccccc4c(=O)n3C)[nH]c(=O)c2c1C]
| | |
|---|---|
| Catalog ID | T0517-2783 |
| Score Lact. | 0.46 |
| EC50 | 3.84 |
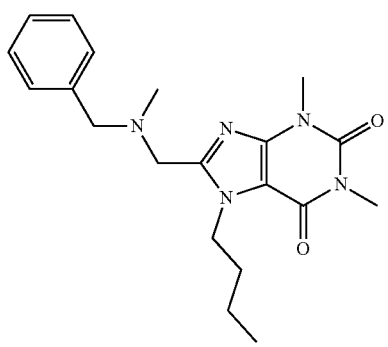 [SMILES: CCCCn1c(CN(C)Cc2ccccc2)nc2c1c(=O)n(C)c(=O)n2C]
| | |
|---|---|
| Catalog ID | T5788545 |
| Score Lact. | 0.45 |
| EC50 | 3.59 |
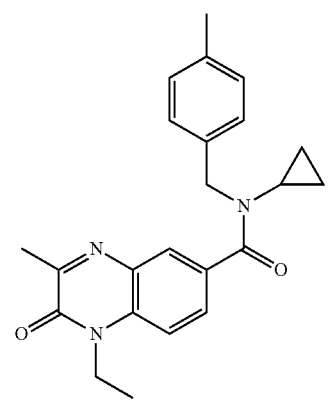 [SMILES: CCn1c(=O)c(C)nc2cc(C(=O)N(Cc3ccc(C)cc3)C3CC3)ccc21]
| | |
|---|---|
| Catalog ID | T5586091 |
| Score Lact. | 0.45 |
| EC50 | 5.36 |
-continued
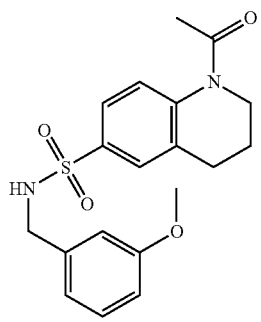
| | |
|---|---|
| Catalog ID | T5967389 |
| Score Lact. | 0.45 |
| EC50 | 9.67 |
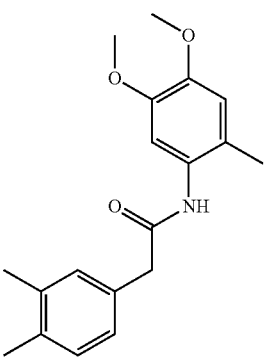
| | |
|---|---|
| Catalog ID | T5783794 |
| Score Lact. | 0.44 |
| EC50 | 6.11 |
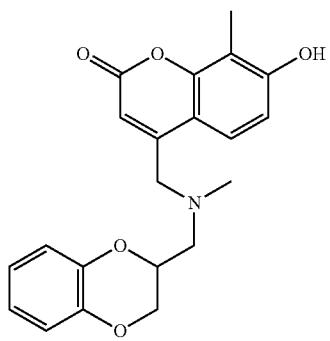 [SMILES: Cc1c(O)ccc2c(CN(C)CC3COc4ccccc4O3)cc(=O)oc12]
| | |
|---|---|
| Catalog ID | T5494352 |
| Score Lact. | 0.44 |
| EC50 | 5024 |

-continued
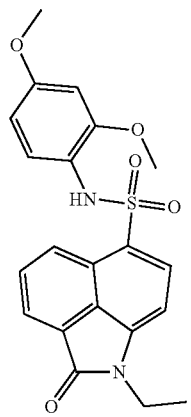 [SMILES: CCN1C(=O)c2cccc3c(S(=O)(=O)Nc4ccc(OC)cc4OC)ccc1c23]
| Catalog ID | T5477696 |
|---|---|
| Score Lact. | 0.44 |
| EC50 | 5.10 |
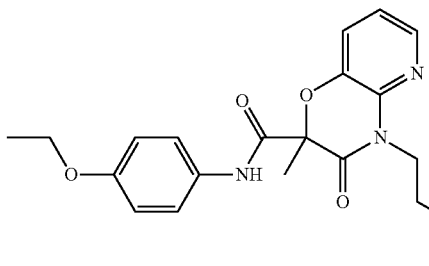
| Catalog ID | P621-1364 |
|---|---|
| Score Lact. | 0.43 |
| EC50 | 5.86 |
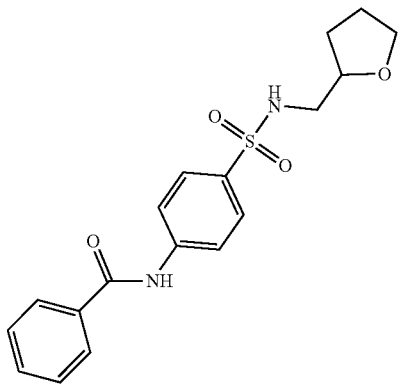 [SMILES: O=C(Nc1ccc(S(=O)(=O)NCC2CCCO2)cc1)c1ccccc1]
| Catalog ID | Y031-0361 |
|---|---|
| Score Lact. | 0.43 |
| EC50 | 8.23 |
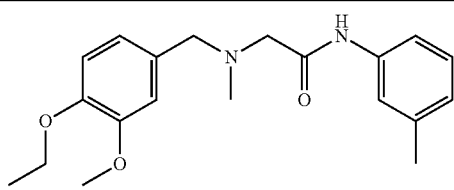
| Catalog ID | T5318833 |
|---|---|
| Score Lact. | 0.42 |
| EC50 | 5.45 |
-continued
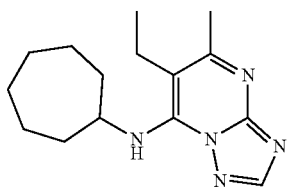 [SMILES: CCc1c(C)nc2ncnn2c1NC1CCCCCC1]
| Catalog ID | Z606-8351 |
|---|---|
| Score Lact. | 0.42 |
| EC50 | 5.0 |
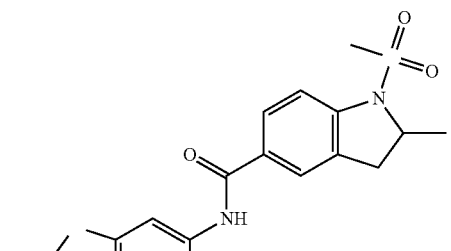
| Catalog ID | T5606387 |
|---|---|
| 0.41 | 0.38 |
| EC50 | 4.61 |
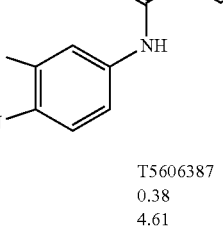
| Catalog ID | T0516-6894 |
|---|---|
| Score Lact. | 0.38 |
| EC50 | 8.21 |
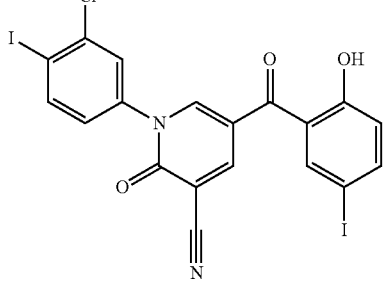
| Catalog ID | T5691896 |
|---|---|
| Score Lact. | 0.38 |
| EC50 | 5.21 |
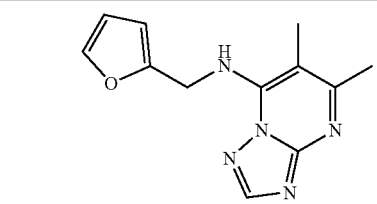 [SMILES: Cc1nc2ncnn2c(NCc2ccco2)c1C]
| Catalog ID | Z606-8298 |
|---|---|
| Score Lact. | 0.38 |
| EC50 | 4.89 |

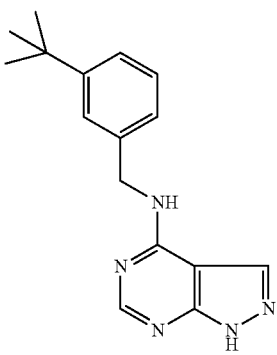 [SMILES: CC(C)(C)c1cccc(CNc2ncnc3[nH]ncc23)c1]
| | |
|---|---|
| Catalog ID | F5285-0069 |
| Score Lact. | 0.36 |
| EC50 | 6.29 |
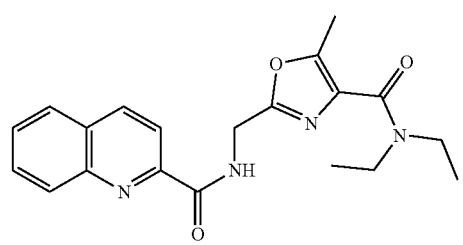 [SMILES: CCN(CC)C(=O)c1nc(CNC(=O)c2ccc3ccccc3n2)oc1C]
| | |
|---|---|
| Catalog ID | T993-1787 |
| Score Lact. | 0.36 |
| EC50 | 7.99 |
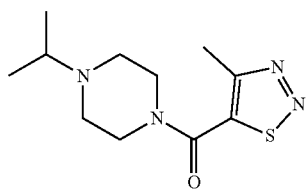 [SMILES: Cc1nnsc1C(=O)N1CCN(C(C)C)CC1]
| | |
|---|---|
| Catalog ID | Z606-5341 |
| Score Lact. | 0.36 |
| EC50 | ND |
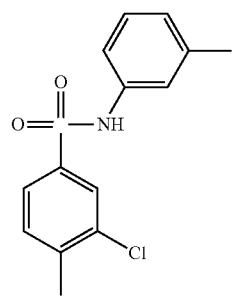
| | |
|---|---|
| Catalog ID | F3394-1364 |
| Score Lact. | 0.33 |
| EC50 | 5.87 |
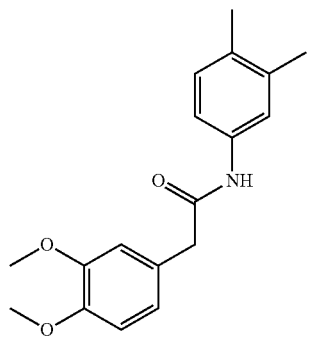
| | |
|---|---|
| Catalog ID | Y030-2832 |
| Score Lact. | 0.34 |
| EC50 | ND |
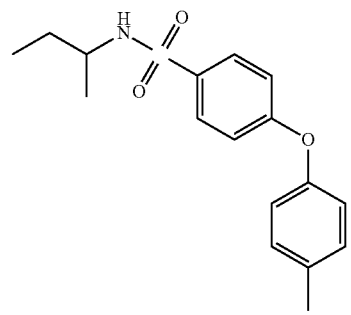
| | |
|---|---|
| Catalog ID | T5400234 |
| Score Lact. | 0.33 |
| EC50 | 4.64 |
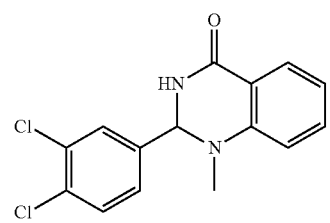 [SMILES: CN1c2ccccc2C(=O)NC1c1ccc(Cl)c(Cl)c1]
| | |
|---|---|
| Catalog ID | T5389517 |
| Score Lact. | 0.33 |
| EC50 | 5.74 |
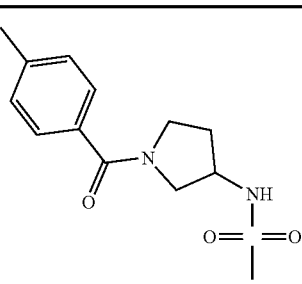
| | |
|---|---|
| Catalog ID | Z603-8037 |
| Score Lact. | 0.32 |
| EC50 | ND |

| | |
|---|---|
| Catalog ID | T0513-0213 |
| Score Lact. | 0.30 |
| EC50 | 3.99 |

| | |
|---|---|
| Catalog ID | T636-2387 |
| Score Lact. | 0.30 |
| EC50 | 6.83 |

What is claimed is:

1. A method of treating a neurological disease, wherein said neurological disease is selected from the group consisting of Amyotrophic lateral sclerosis (ALS), and a subtype thereof in a subject in need thereof, said method comprising administering to a subject in need thereof a therapeutically effective amount of a compound of Formula II:

wherein:
$R^{II'}$ is —H;
$B^{II}$ is cyclopentyl each optionally and independently substituted with one or more $R^{BII}$;
$X^{II'}$ is selected from —NR*—, piperidinyl, piperazinyl, morpholinyl, pyrrolidinyl, or imidazolidinyl, each optionally and independently substituted with one or more $R^{XII'}$;
$X^{II}$ is a C1-C10 alkylenyl wherein optionally one or more carbon atoms are each independently replaced by —O—, —C(O)—, —NR*—, piperidinyl, piperazinyl, morpholinyl, pyrrolidinyl, or imidazolidinyl, and wherein the alkylenyl or said piperidinyl, piperazinyl, morpholinyl, pyrrolidinyl or imidazolidinyl is optionally and independently substituted with one or more $R^{XII}$;
$Y^{II}$ is pyridyl, pyrimidinyl, pyridazinyl, pyrazinyl, thiophenyl, furanyl, pyrrolyl, imidazolyl, thiazolyl, pyrazolyl, triazolyl, oxazolyl, benzoxazolyl, or benzoisoxazolyl, each optionally and independently substituted with one or more $R^{YII}$;
each R* is independently-H or optionally substituted C1-C6 alkyl;
each $R^{BII}$ is independently C1-C6 alkyl, C1-C6 haloalkyl, halo, or —CN;
each $R^{XII'}$ is independently C1-C6 alkyl, C1-C6 haloalkyl, halo or —CN;
each $R^{XII}$ is independently C1-C6 alkyl, C1-C6 haloalkyl, halo, —CN, cycloalkyl, or —NR*$_2$; and
each $R^{YII}$ is independently C1-C6 alkyl, C1-C6 haloalkyl, —O(C1-C6 alkyl), halo, or —CN.

2. The method of claim 1, wherein said disease is selected from the group consisting of bulbar-onset ALS and limb-onset ALS.

3. The method of claim 1, further comprising administering a drug selected from the group consisting of riluzole and edaravone.

4. The method of claim 1, further comprising administering a non-drug treatment selected from the group consisting of invasive and non-invasive mechanical ventilation.

5. The method of claim 1, further comprising delaying disease onset in individuals at risk for disease development according to one or more predictive markers.

6. The method of claim 1 wherein the compound is selected from the following structural formulas:

T636-1937

T636-1114

T636-2425

7. The method of claim 1 wherein:
$R^{II'}$ is —H;
$B^{II}$ is cyclopentyl;
$X^{II'}$ is piperidinyl, piperazinyl, morpholinyl, pyrrolidinyl, or imidazolidinyl;
$X^{II}$ is a C1-C10 alkylenyl wherein optionally one or more carbon atoms are each independently replaced by —C(O)—, —NR*;
$Y^{II}$ is pyridyl, pyrimidinyl, pyridazinyl, pyrazinyl, thiophenyl, furanyl, pyrrolyl, imidazolyl, pyrazolyl, triazolyl, benzoxazolyl, or benzoisoxazolyl, each optionally and independently substituted with one or more $R^{YII}$;
each R* is independently-H or optionally substituted C1-C6 alkyl; and
each $R^{YII}$ is independently C1-C6 alkyl, C1-C6 haloalkyl, —O(C1-C6 alkyl), halo, or —CN.

* * * * *